(12) United States Patent
Saggar et al.

(10) Patent No.: US 7,807,684 B2
(45) Date of Patent: Oct. 5, 2010

(54) HIV REVERSE TRANSCRIPTASE INHIBITORS

(75) Inventors: Sandeep A. Saggar, Charlottesville, VA (US); John T. Sisko, Lansdale, PA (US); Thomas J. Tucker, North Wales, PA (US); Robert M. Tynebor, Hatfield, PA (US); Dai-Shi Su, Dresher, PA (US); Neville J. Anthony, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1114 days.

(21) Appl. No.: 11/487,885

(22) Filed: Jul. 17, 2006

(65) Prior Publication Data

US 2007/0021442 A1  Jan. 25, 2007

Related U.S. Application Data

(60) Provisional application No. 60/701,797, filed on Jul. 22, 2005, provisional application No. 60/727,916, filed on Oct. 18, 2005, provisional application No. 60/790,705, filed on Apr. 10, 2006.

(51) Int. Cl.
  C07D 471/02  (2006.01)
  A61K 31/47  (2006.01)

(52) U.S. Cl. .............. 514/260.1; 514/301; 514/302; 514/303; 514/359; 514/406; 514/394; 514/205; 544/205; 546/112; 546/113; 546/114; 546/117; 546/118; 548/216; 548/304.1

(58) Field of Classification Search .............. None
See application file for complete search history.

(56) References Cited

U.S. PATENT DOCUMENTS

| | | | |
|---|---|---|---|
| 3,600,437 A | 8/1971 | Marshall | |
| 4,404,018 A | 9/1983 | Stach et al. | |
| 4,443,248 A | 4/1984 | Hokama | |
| 4,599,105 A | 7/1986 | Malhotra et al. | |
| 5,164,407 A | 11/1992 | Greenlee et al. | |
| 5,389,660 A | 2/1995 | Greenlee et al. | |
| 5,648,368 A | 7/1997 | Egbertson et al. | |
| 5,665,737 A | 9/1997 | Cavalla et al. | |
| 5,710,171 A | 1/1998 | Dinsmore et al. | |
| 5,739,144 A | 4/1998 | Warrellow et al. | |
| 5,744,492 A | 4/1998 | Kohn et al. | |
| 5,994,376 A | 11/1999 | Freyne et al. | |
| 6,057,346 A | 5/2000 | Kohn et al. | |
| 6,117,886 A | 9/2000 | Timmerman et al. | |
| 6,348,032 B1 | 2/2002 | Sperl et al. | |
| 7,166,738 B2 | 1/2007 | Dunn et al. | |
| 7,208,509 B2 | 4/2007 | Dunn et al. | |
| 7,348,345 B2 | 3/2008 | Dunn et al. | |
| 7,625,949 B2 | 12/2009 | Dunn et al. | |
| 7,666,891 B2 | 2/2010 | Dunn et al. | |
| 2003/0100554 A1 | 5/2003 | Jones et al. | |
| 2004/0006114 A1 | 1/2004 | Coleman et al. | |
| 2004/0122064 A1 | 6/2004 | Chan | |
| 2004/0242654 A1 | 12/2004 | Kohno et al. | |
| 2005/0095215 A1 | 5/2005 | Popp | |
| 2005/0197340 A1 | 9/2005 | Arora et al. | |
| 2005/0203091 A1 | 9/2005 | Arora et al. | |
| 2005/0209282 A1 | 9/2005 | Wilson et al. | |
| 2005/0228000 A1 | 10/2005 | Smallheer et al. | |
| 2008/0045511 A1 | 2/2008 | Kennedy-Smith et al. | |

FOREIGN PATENT DOCUMENTS

| | | |
|---|---|---|
| CA | 1120034 | 3/1982 |
| EP | 0 003 584 A1 | 8/1979 |
| EP | 0 003 584 B1 | 8/1979 |
| EP | 0 011 802 A1 | 6/1980 |
| EP | 0 281 103 A2 | 9/1988 |
| EP | 0 537 538 A1 | 4/1993 |
| EP | 0 622 077 A1 | 11/1994 |
| EP | 1 431 267 A1 | 6/2004 |
| EP | 1 584 619 A1 | 10/2005 |
| EP | 1 208 091 B1 | 5/2006 |
| EP | 1 661 879 A1 | 5/2006 |
| JP | 56002965 A * | 1/1981 |
| WO | WO 96/37204 | 11/1996 |
| WO | WO 98/01428 | 1/1998 |

(Continued)

OTHER PUBLICATIONS

English Translation of JP56002965, Mitsui Toatsu Chemicals, Jan. 1981.*

Chintakunta, V. et al. "3-O-Substituted benzyl pyridazinone derivatives as COX inhibitors", European Journal of Medicinal Chemistry, 2002, vol. 37, pp. 339-347.

De Lucca, G. et al. "Nonsymmetric P2/P2' Cyclic Urea HIV Protease Inhibitors. Structure-Activity Relationship, Bioavailabilty, and Resistance Profile of Monoindazole-Substituted P2 Analogues", Journal of Medicinal Chemistry, 1998, vol. 41, pp. 2411-2423.

(Continued)

*Primary Examiner*—Zinna N Davis
(74) *Attorney, Agent, or Firm*—Kenneth R. Walton; Sheldon O. Heber

(57) ABSTRACT

Compounds having the structure:

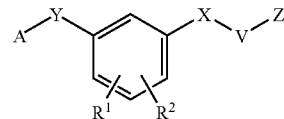

are HIV reverse transcriptase inhibitors, wherein A, X, Y, Z, $R^1$ and $R^2$ are defined herein. The compounds and their pharmaceutically acceptable salts are useful in the inhibition of HIV reverse transcriptase, the prophylaxis and treatment of infection by HIV and in the prophylaxis, delay in the onset, and treatment of AIDS. The compounds and their salts can be employed as ingredients in pharmaceutical compositions, optionally in combination with other antivirals, immunomodulators, antibiotics or vaccines.

15 Claims, No Drawings

FOREIGN PATENT DOCUMENTS

| WO | WO 00/68201 | 11/2000 |
|---|---|---|
| WO | WO 02/070470 A2 | 9/2002 |
| WO | WO 02/074726 A2 | 9/2002 |
| WO | WO 03/048134 A1 | 6/2003 |
| WO | WO 2004/019941 A1 | 3/2004 |
| WO | WO 2004/085406 A1 | 10/2004 |
| WO | WO 2004/085411 A1 | 10/2004 |
| WO | WO 2004/096807 A2 | 11/2004 |
| WO | WO 2005/099709 A2 | 10/2005 |
| WO | WO 2005/105766 A2 | 11/2005 |
| WO | WO 2006/067587 A2 | 6/2006 |
| WO | WO 2006/076706 A1 | 7/2006 |
| WO | WO 2006/077025 A2 | 7/2006 |

OTHER PUBLICATIONS

Doskotch, R. et al. "Codonocarpus Alkaloids-III The Structure of Codonocarpine", Tetrahedron, 1974, vol. 30, pp. 3229-3236.

Feit, P. et al. "Aminobenzoic Acid Diuretics. 3.1 4-Substituted 5-Sulfamylanthranilic Acid Derivatives", Journal of Medicinal Chemistry, 1972, vol. 15, pp. 79-83.

Li, X. et al. "A novel phase-switching protecting group for multi-step parallel solution phase synthesis", Organic and Biomolecular Chemistry, 2004, vol. 2, pp. 989-998.

Musser, J. et al. "N-[(Arylmethoxy)phenyl] Carboxylic Acids, Hydroxamic Acids, Tetrazoles and Sulfonyl Carboxamides. Potent Orally Active Leukotriene D4 Antagonists of Novel Structure", Journal of Medicinal Chemistry, 1990, vol. 33, pp. 240-245.

Nandihalli, U. et al. "Enantioselectivity of Protoporphyrinogen Oxidase-Inhibiting Herbicides", Pesticide Science, 1994, vol. 40, pp. 265-277.

Papot, S. et al. "Design of Selectivity Activated Anticancer Prodrugs: Elimination and Cyclization Strategies", Current Medicinal Chemistry—Anti Cancer Agents, 2002, vol. 2, pp. 155-185.

Saari, W. et al. "Cyclization-Activated Prodrugs. Basic Carbamates of 4-Hydroxyanisole", Journal of Medicinal Chemistry, 1990, vol. 33, pp. 97-101.

Santos, C. et al. "Cyclization-activated prodrugs. Synthesis, reactivity and toxicity of dipeptide esters of paracetamol", Bioorganic & Medicinal Chemistry Letters, 2005, vol. 15, pp. 1595-1598.

Wyatt, P. et al. "Benzophenone Derivatives: A Novel Series of Potent and Selective Inhibitors of Human Immunodeficiency Virus Type 1 Reverse Transcriptase", Journal of Medicinal Chemistry, 1995, vol. 38, pp. 1657-1665.

Database CHEMCATS, Accession No. 2006:3663485, XP002413978, Jan. 24, 2006.

Database CHEMCATS, Accession No. 2006:3640051, XP002413979, Jan. 24, 2006.

Database CHEMCATS, Accession No. 2006:3646612, XP002413980, Jan. 24, 2006.

Database Beilstein, Beilstein Registry No. 10083060, XP002414728, Apr. 2005.

CAPLUS Database, Accession No. 1981:46881, Abstract of Schoenowsky et al., "Nitrodiphenyl ethers, their preparation and herbicidal activity", Zeitschrift fuer Naturforschung, 1980, vol. 35B, pp. 902-908. XP002414729.

CAPLUS Datbase, Accession No. 2005:1042231, Kawamoto et al., "Preparation and heterocyclic compounds as G protein-coupled receptor kinase (GRK) inhibitors", Abstract of WO 2005/090328 (Takeda Pharmaceuticals Co., Ltd.).

Derwent Abstract No. 93-127048/16, "Fluorinated phenoxy-phenoxy-carboxylic acid derivatives", Abstract of DE 4133674-A1, 1993, (Bayer AG) (corresponds to EP 0 537 538).

Derwent Abstract No. 61653B/34, "Meta-aryloxy-phenoxy-propionic acid derivatives—useful as herbicides", Abstract of DT 2805-981, 1978, (Bayer AG) (corresponds to EP 0 003 584).

Derwent Abstract No. 2003-541543/51, "Sodium-phosphate cotransporter inhibitors comprise new and known triazole compounds", Abstract of WO 2003048134A1, 2003, (Japan Tobacco).

* cited by examiner

HIV REVERSE TRANSCRIPTASE INHIBITORS

This application claims the benefit of U.S. Provisional Application Nos. 60/701,797 (filed Jul. 22, 2005), 60/727,916 (filed Oct. 18, 2005), and 60/790,705 (filed Apr. 10, 2006), the disclosures of which are hereby incorporated by reference in their entireties.

FIELD OF THE INVENTION

The present invention is directed to certain substituted aromatic compounds and their pharmaceutically acceptable salts and their use for the inhibition of HIV reverse transcriptase, the prophylaxis and treatment of HIV infection and HIV replication, and the prophylaxis, delay in the onset of and treatment of AIDS.

BACKGROUND OF THE INVENTION

The retrovirus designated human immunodeficiency virus (HIV), particularly the strains known as HIV type-1 (HIV-1) and type-2 (HIV-2) viruses, have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz and abacavir.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

The following references are of interest as background:
WO 02/070470 (corresponding to US 2004/0122064) describes benzophenones as inhibitors of reverse transcriptase.
WO 2003/029184 (corresponding to US 2004/0242654) describes diaryl ether derivatives as immunosuppressants.
WO 96/37204 (corresponding to U.S. Pat. No. 5,710,171) describes 3-substituted phenoxy compounds as farnesyl-protein transferase inhibitors.
U.S. Pat. No. 3,600,437 discloses certain phenylalkanoic acid derivatives including certain phenoxyphenylalkanamides, phenylthiophenylalkanamides, and certain tetrazoles. The compounds are disclosed to be useful as antiinflammatory, analgesic and antipyretic agents.
U.S. Pat. No. 5,665,737 discloses certain cycloalkyloxyphenylalkylbenzoxazole compounds including 7-bromo-5-chloro-2-[2-[3-(cyclopentyloxy)-4-methoxyphenyl]ethyl]benzoxazole. The compounds are disclosed to be effective in the mediation or inhibition of PDE IV.
U.S. Pat. No. 5,994,376 discloses certain cycloalkyloxyphenylalkyl-2H-imidazolone compounds including 1-[2-[3-(cyclopentyloxy)-4-methoxyphenyl]ethyl]-1,3-dihydro-2H-imidazol-2-one. The compounds are disclosed as useful for treating disease states related to abnormal enzymic or catalytic activity of PDE IV.
U.S. Pat. No. 6,057,346 discloses the inhibition of retroviral LTR promoters by a class of calcium response modifiers that includes certain imidazolylalkyl- and triazolylalkyl-substituted diaryl compounds in which the aryl moieties are linked by O, S, SO$_2$, or another linking group.
U.S. Pat. No. 6,348,032 B1 discloses inhibition of neoplastic cells with a genus of certain benzimidzole derivatives including certain (phenyloxyphenyl)alkylbenzimidazoles.
Other references disclosing linked diaryl compounds of interest include EP 622077 A1; US 2005/0095215 A1; and Feit et al., J. Med. Chem. 1972, 15: 79-83.
The compounds described in this invention represent a novel structural class of non-nucleoside reverse transcriptase inhibitors.

SUMMARY OF THE INVENTION

The present invention is directed to certain substituted aromatic compounds and their use in the inhibition of HIV reverse transcriptase, the prophylaxis of infection by HIV, the treatment of infection by HIV, and the prophylaxis, treatment, and delay in the onset of AIDS and/or ARC. More particularly, the present invention includes compounds of Formula I and pharmaceutically acceptable salts thereof:

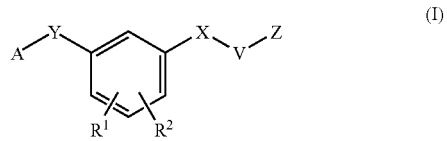

wherein:
R$^1$ and R$^2$ are independently selected from the group consisting of:
a) H,
b) C$_{1-6}$ alkyl,
c) C$_{3-6}$ cycloalkyl,
d) C$_{1-3}$ fluoroalkyl,
e) NO$_2$,
f) halogen, g) $OR^3$,
h) $O(CH_2)_sOR^3$,
i) $CO_2R^3$,
j) $(CO)NR^3R^4$,
k) $O(CO)NR^3R^4$,
l) $N(R^3)(CO)NR^3R^4$,
m) $N(R^3)(CO)R^4$,
n) $N(R^3)(CO)OR^3$,
o) $SO_2NR^3R^4$,
p) $N(R^3)SO_2R^4$,
q) $S(O)_mR^3$,
r) CN,
s) $NR^3R^4$,
t) $N(R^3)(CO)NR^3R^4$, and
u) $O(CO)R^3$;

A is aryl, $C_{3-7}$ cycloalkyl, or heterocyclyl;
V is $—C(R^5R^6)—$;
X is selected from the group consisting of —O—, —NH—, and —$C(R^5R^6)$—;
Y is selected from the group consisting of —O—, —$C(R^5R^6)$—, and —$S(O)_m$—;
Z is selected from the group consisting of —$C(O)NR^7R^8$, —$C(O)R^9$, and $R^{10}$;
$R^5$ and $R^6$ are independently selected from the group consisting of hydrogen, $C_{1-6}$ alkyl, $C_{1-3}$ fluoroalkyl, and $OR^3$;
$R^7$ is selected from the group consisting of hydrogen, $C_{1-6}$ alkyl, and $C_{1-3}$ fluoroalkyl;
$R^8$ is selected from the group consisting of:
  a) aryl,
  b) $C_{3-6}$ cycloalkyl,
  c) $C_{1-6}$ alkyl,
  d) $C_{1-3}$ fluoroalkyl, and
  e) heterocyclyl;
$R^9$ is selected from the group consisting of:

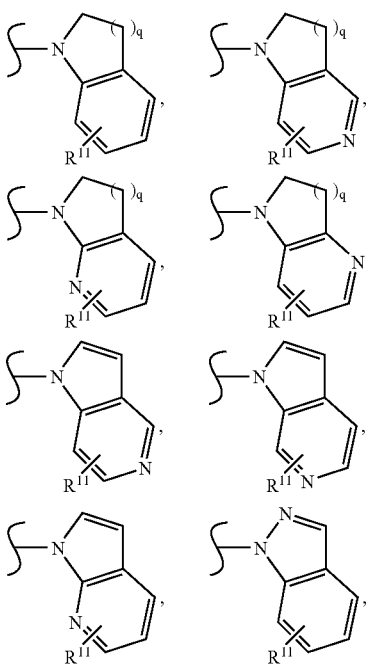

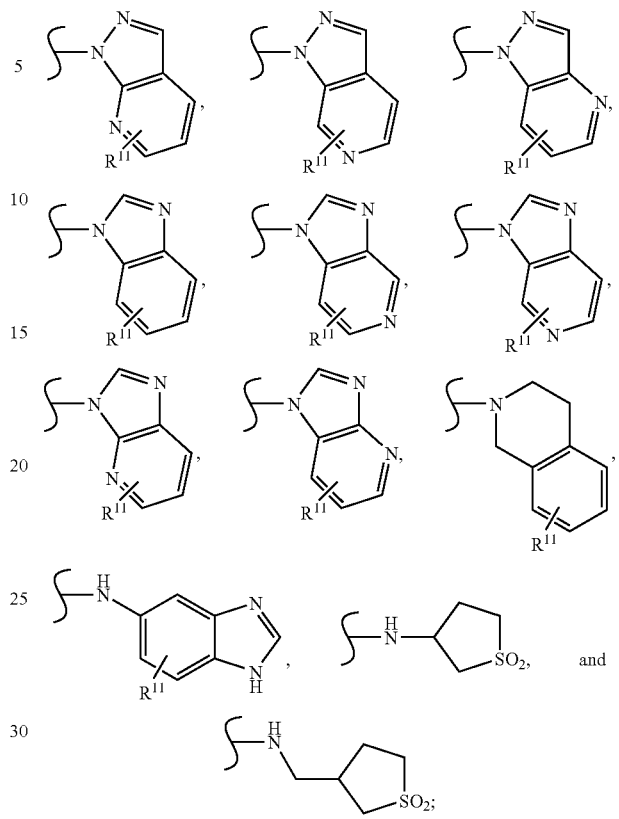

$R^{10}$ is a heterocyclyl selected from the group consisting of:

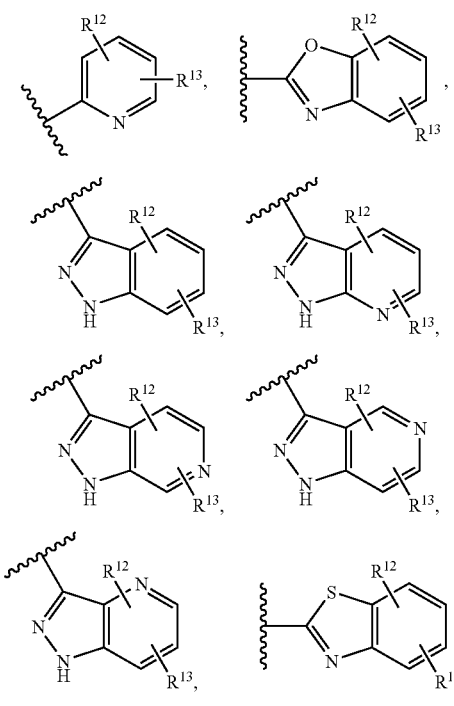

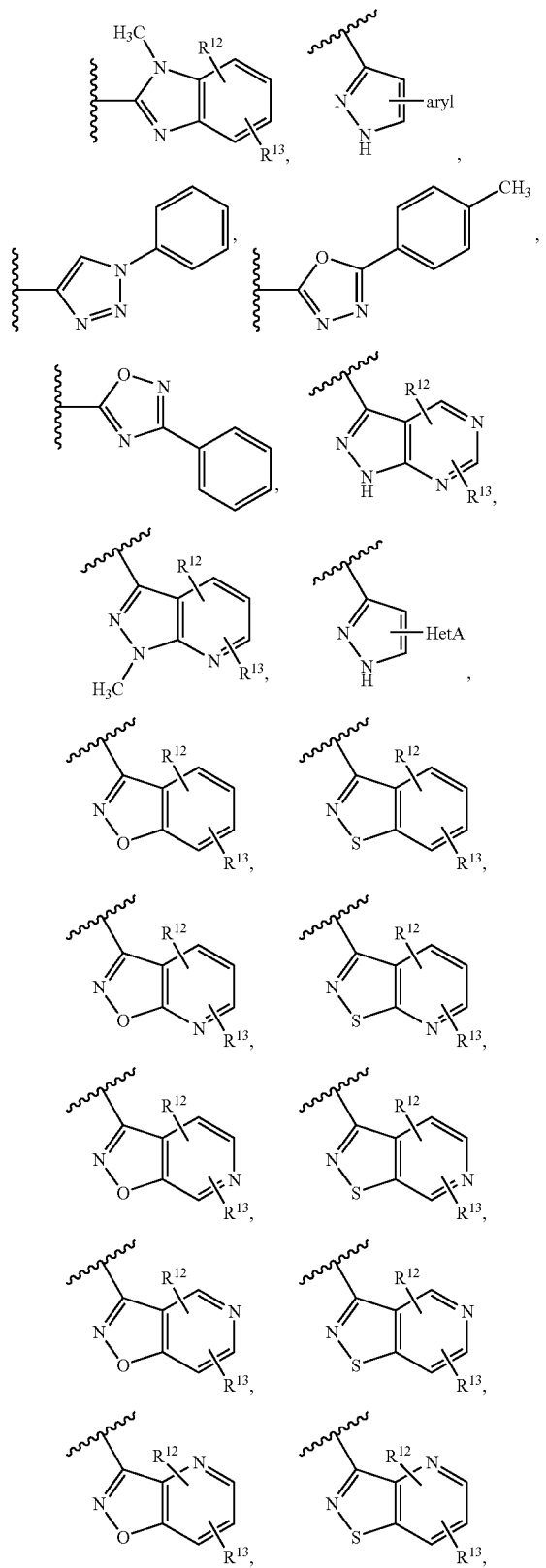
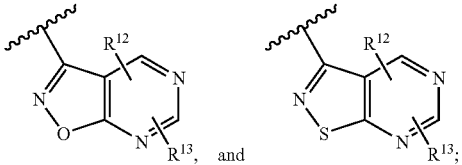

$R^{11}$ is selected from the group consisting of hydrogen, halogen, $NO_2$, CN, $OR^3$, $O(CH_2)_sOR^3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl, $C_{1-3}$ fluoroalkyl, and $NR^3R^4$;

$R^3$ and $R^4$ are independently selected from the group consisting of hydrogen, $C_{1-6}$ alkyl, $C_{1-3}$ fluoroalkyl, and $C_{3-6}$ cycloalkyl;

or, alternatively and optionally, when $R^3$ and $R^4$ are in an $NR^3R^4$ group, then:

(A) one of $R^3$ and $R^4$ is selected from the group consisting of hydrogen, $C_{1-6}$ alkyl, $C_{1-3}$ fluoroalkyl, and $C_{3-6}$ cycloalkyl, and the other of $R^3$ and $R^4$ is $C_{1-6}$ alkyl substituted with O—$C_{1-6}$ alkyl, $C(O)R^A$, $CO_2R^A$, $C(O)N(R^A)R^B$, $SR^A$, $S(O)R^A$, $SO_2R^A$, or $SO_2N(R^A)R^B$; or (B) $R^3$ and $R^4$ together with the nitrogen atom to which they are both attached form (i) a 4- to 7-membered, saturated or unsaturated monocyclic ring optionally containing 1 or 2 heteroatoms in addition to the nitrogen attached to $R^3$ and $R^4$ selected from N, O, and S, where the S is optionally oxidized to S(O) or $S(O)_2$, or (ii) a 7- to 12-membered bicyclic ring system wherein each ring in (ii) is independent of, fused to, or bridged with the other ring and each ring is saturated or unsaturated, and wherein the bicyclic ring system optionally contains from 1 to 3 heteroatoms in addition to the nitrogen attached to $R^3$ and $R^4$ selected from N, O, and S, where the S is optionally oxidized to S(O) or $S(O)_2$, and wherein the monocyclic ring or the bicyclic ring system is optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, or $SO_2N(R^A)R^B$, (4) O—$C_{1-6}$ alkyl, (5) O—$C_{1-6}$ haloalkyl, (6) OH, (7) oxo, (8) halogen, (9) CN, (10) $NO_2$, (11) $N(R^A)R^B$, (12) $C(O)N(R^A)R^B$, (13) $C(O)R^A$, (14) $C(O)$—$C_{1-6}$ haloalkyl, (15) $C(O)OR^A$, (16) $OC(O)N(R^A)R^B$, (17) $SR^A$, (18) $S(O)R^A$, (19) $S(O)_2R^A$, (20) $S(O)_2N(R^A)R^B$, (21) $N(R^A)COR^B$, or (22) $N(R^A)SO_2R^B$ and wherein each $R^A$ is independently H or $C_{1-6}$ alkyl, and each $R^B$ is independently H or $C_{1-6}$ alkyl;

$R^{12}$ and $R^{13}$ are independently selected from the group consisting of hydrogen, halogen, oxo, $NO_2$, CN, $OR^3$, $O(CH_2)_tCF_3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl, $C_{1-3}$ fluoroalkyl, $C_{3-6}$ cycloalkyl, and $NR^3R^4$;

HetA is heteroaryl selected from the group consisting of pyridinyl, pyrimidinyl, and pyrazinyl;

s is 1-5;

q is 1-3;

t is 2-3;

v is 1-2; and m, in each instance in which it appears, is independently selected from 0-2;

and provided that:
(A) when X is —C(R⁵R⁶)— and Z is R¹⁰, then neither R¹ nor R² is OR³; or
(B) when A is unsubstituted phenyl, Y is O or S, X is —C(R⁵R⁶)—, and Z is —C(O)NR⁷R⁸, then R⁸ is not $C_{1-6}$ alkyl.

Other embodiments, aspects and features of the present invention are either further described in or will be apparent from the ensuing description, examples and appended claims.

DETAILED DESCRIPTION OF THE DISCLOSURE

The compounds of Formula I above, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. Based upon the testing of representative compounds of the invention in the assay set forth in Example 56 below, it is known that compounds of Formula I inhibit the RNA-dependent DNA polymerase activity of HIV-1 reverse transcriptase. Certain of the compounds of the present invention can also exhibit activity against drug resistant forms of HIV (e.g., mutant strains of HIV in which reverse transcriptase has a mutation at lysine 103→asparagine (K103N) and/or tyrosine 181→cysteine (Y181C)), and thus can exhibit decreased cross-resistance against currently approved antiviral therapies.

An embodiment of the present invention (alternatively referred to herein as "Embodiment E1") is a compound of Formula I as set forth above, or a pharmaceutically acceptable salt thereof, wherein:

R¹⁰ is selected from the group consisting of:

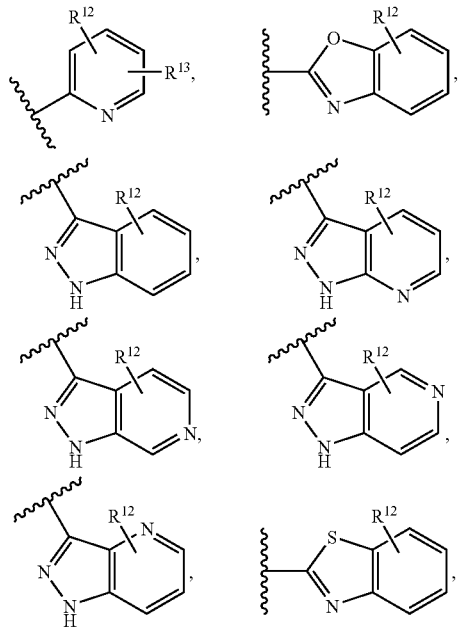

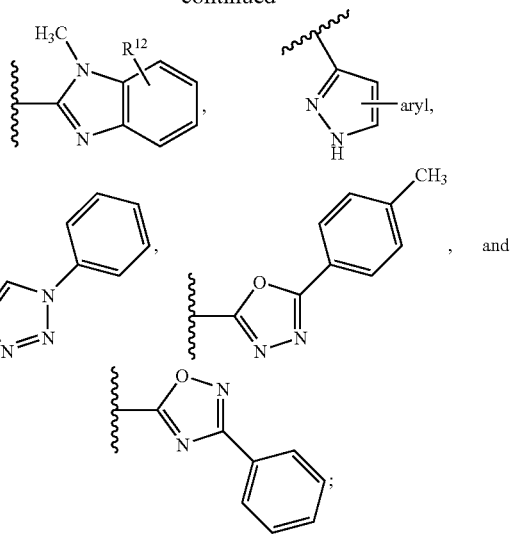

and all other variables and provisos are as originally defined above (i.e., as defined in the Summary of the Invention).

Another embodiment of the present invention (Embodiment E2) is a compound of Formula I, or a pharmaceutically acceptable salt thereof, wherein:
X is selected from the group consisting of —O— and —NH—;
Y is selected from the group consisting of —O—, —CH₂—, and —S(O)$_m$—;
R³ and R⁴ are independently selected from the group consisting of hydrogen, $C_{1-6}$ alkyl, and $C_{1-3}$ fluoroalkyl;
R⁵ and R⁶ are independently selected from the group consisting of hydrogen and $C_{1-6}$ alkyl;
R¹⁰ is as defined in Embodiment E1;
R¹¹ is selected from the group consisting of hydrogen, halogen, NO₂, CN, OR³, O(CH₂)$_t$OR³, CO₂R³, CONR³R⁴, O(CH₂)$_t$NR³R⁴, O(CH₂)$_v$COR³, S(O)$_m$R³, SO₂NR³R⁴, and $C_{1-6}$ alkyl;
R¹² and R¹³ are independently selected from the group consisting of hydrogen, halogen, oxo, NO₂, CN, OR³, O(CH₂)$_t$CF₃, CO₂R³, CONR³R⁴, O(CH₂)$_t$NR³R⁴, O(CH₂)$_v$COR³, S(O)$_m$R³, SO₂NR³R⁴, $C_{1-6}$ alkyl and $C_{1-3}$ fluoroalkyl;

and all other variables are as originally defined above.

Another embodiment of the present invention (Embodiment E3) is a compound of Formula I, or a pharmaceutically acceptable salt thereof, wherein all of the variables and provisos are as originally defined or as defined in Embodiment E1 or Embodiment E2, except that in the definition of

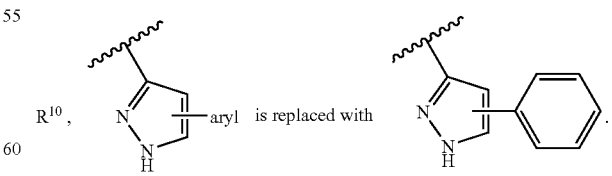

Another embodiment of the present invention (Embodiment E4) is a compound of Formula I, or a pharmaceutically acceptable salt thereof, wherein:
X is selected from the group consisting of —O—, —NH—, and —CH₂—;

Y is selected from the group consisting of —O—, —CH$_2$—, and —S(O)$_m$—;

R$^{10}$ is as originally defined or as defined in Embodiment E1 or Embodiment E3;

and all other variables are as originally defined or as defined in Embodiment E2;

and provided that:
(A) when X is —CH$_2$— and Z is R$^{10}$, then neither R$^1$ nor R$^2$ is OR$^3$; or
(B) when A is unsubstituted phenyl, Y is O or S, X is —CH$_2$—, and Z is —C(O)NR$^7$R$^8$, then R$^8$ is not C$_{1-6}$ alkyl.

Another embodiment of the present invention (Embodiment E5) includes compounds of Formula Ia:

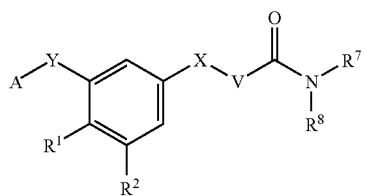

(Ia)

and pharmaceutically acceptable salts thereof, wherein all variables are as originally defined for Formula I; and provided that when A is unsubstituted phenyl, Y is O or S, and X is —C(R$^5$R$^6$)—, then R$^8$ is not C$_{1-6}$ alkyl.

A class of the preceding embodiment (Class C1) includes compounds of Formula Ia and pharmaceutically acceptable salts thereof, wherein:

X is selected from the group consisting of —O—, —NH—, and —CH$_2$—;

Y is selected from the group consisting of —O—, —CH$_2$—, and —S(O)$_m$—;

and all other variables are as defined in Embodiment E5;

and provided that when A is unsubstituted phenyl, Y is O or S, and X is —CH$_2$—, then R$^8$ is not C$_{1-6}$ alkyl.

Another class of the preceding embodiment (Class C2) includes compounds of Formula Ia and pharmaceutically acceptable salts thereof, wherein:

X is selected from the group consisting of —O— and —NH—;

Y is selected from the group consisting of —O—, —CH$_2$—, and —S(O)$_m$—;

R$^3$ and R$^4$ are independently selected from the group consisting of hydrogen, C$_{1-6}$ alkyl, and C$_{1-3}$ fluoroalkyl;

R$^5$ and R$^6$ are independently selected from the group consisting of hydrogen and C$_{1-6}$ alkyl;

and all other variables are as defined in Embodiment E5.

Another embodiment of the present invention (Embodiment E6) includes compounds of Formula Ia, and pharmaceutically acceptable salts thereof, wherein:

R$^1$ and R$^2$ are independently selected from the group consisting of:
a) H,
b) C$_{1-6}$ alkyl,
c) C$_{3-6}$ cycloalkyl,
d) C$_{1-3}$ fluoroalkyl,
e) halogen,
f) OR$^3$,
g) S(O)$_m$R$^3$,
h) CN, and
i) NR$^3$R$^4$;

R$^7$ is H, —CH$_2$CH$_3$, or —CH$_3$;
R$^8$ is aryl or heterocyclyl;

V is —CH$_2$— or —CH(CH$_3$)—;

and all other variables are as defined in Embodiment E5.

Another embodiment of the present invention (Embodiment E7) is a compound of Formula Ia, or a pharmaceutically acceptable salt thereof, wherein:

X is —O— or —NH—;

R$^3$ and R$^4$ are independently selected from the group consisting of hydrogen, C$_{1-6}$ alkyl, and C$_{1-3}$ fluoroalkyl;

and all other variables are as defined in Embodiment E6.

A class of the preceding embodiment (Class C3) includes compounds of Formula Ia and pharmaceutically acceptable salts thereof, wherein:

Y is selected from the group consisting of —O—, —CH$_2$—, and —S(O)$_m$—;

and all other variables are as defined in Embodiment E7.

A preferred embodiment of the present invention (Embodiment E8) includes compounds of the Formula Ia, and pharmaceutically acceptable salts thereof, wherein R$^1$ and R$^2$ are independently selected from the group consisting of hydrogen, C$_{1-6}$ alkyl, and halogen; R$^7$ is H, —CH$_2$CH$_3$, or —CH$_3$; R$^8$ is selected from the group consisting of:

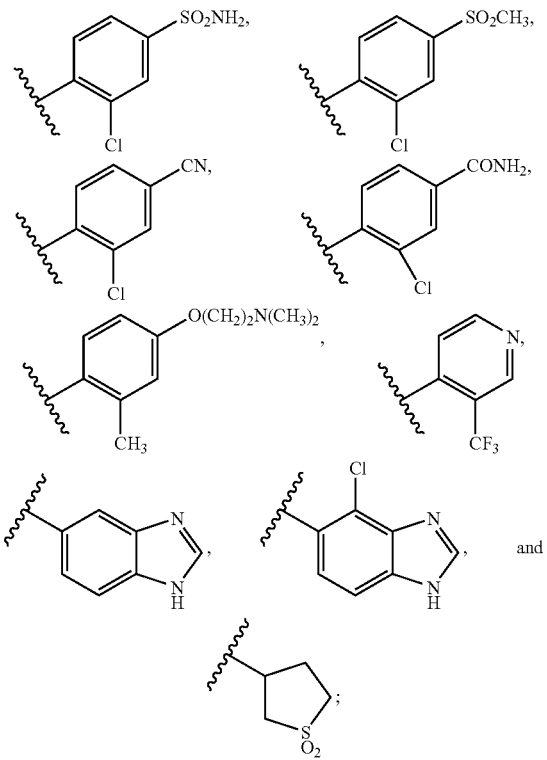

A is selected from the group consisting of:

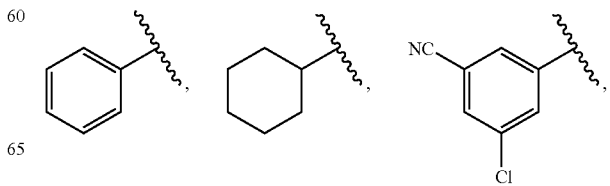

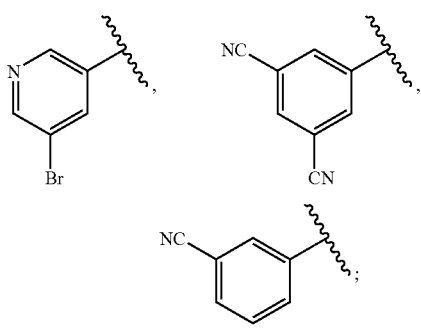
V is —CH₂— or —CH(CH₃)—;
X is —O— or —NH—; and
Y is —O— or —CH₂—.
Specific examples of compounds of Formula Ia, and pharmaceutically acceptable salts thereof, include
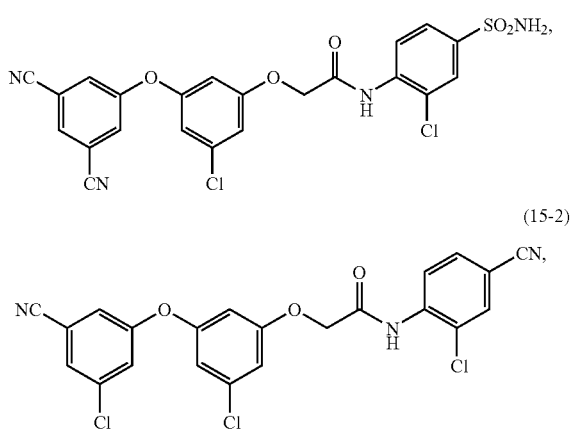

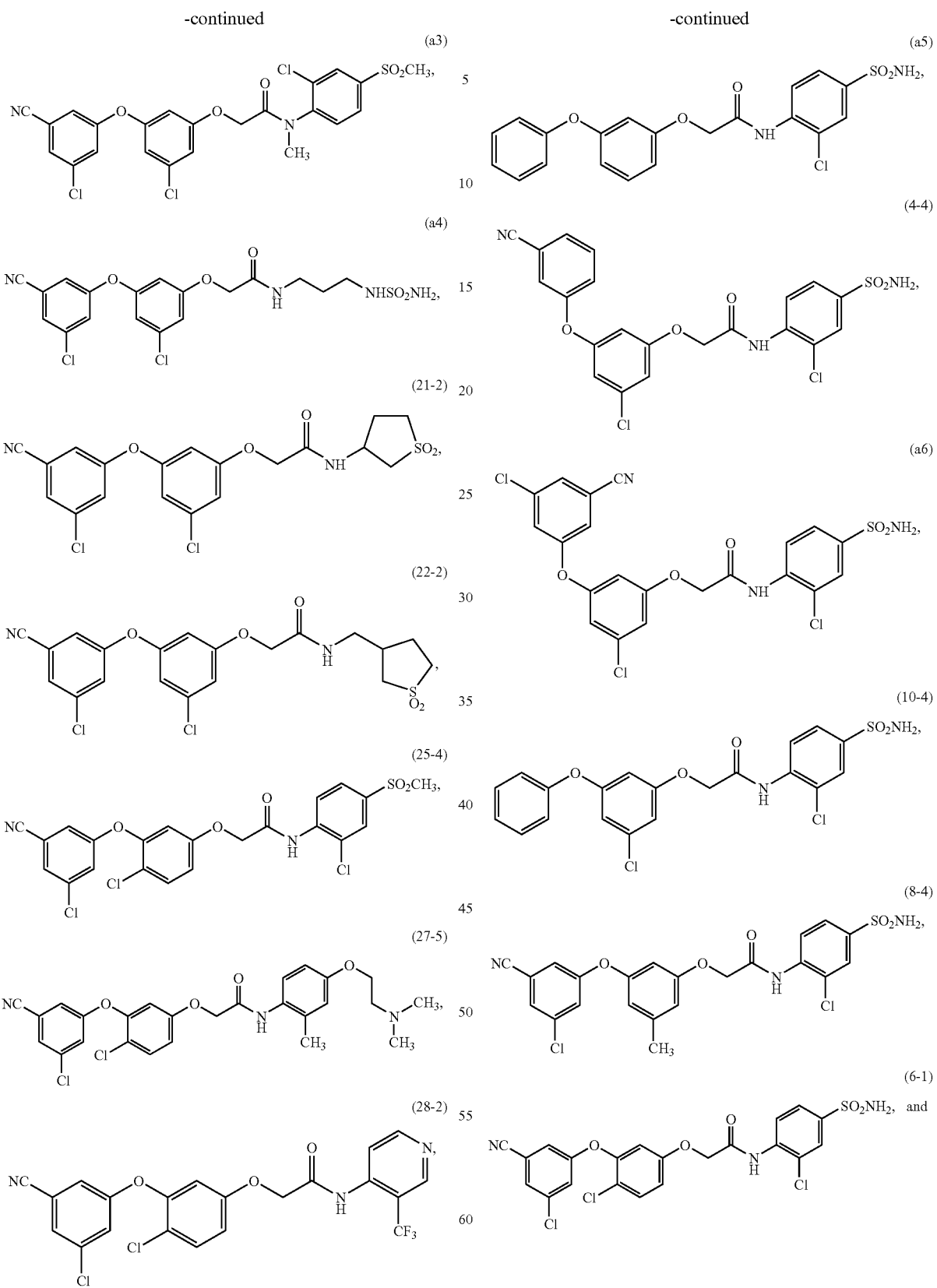

-continued (12-2)

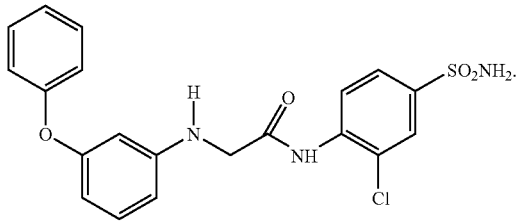

The compounds represented by the structures shown above have the following names:
(14-5) N-[4-(aminosulfonyl)-2-chlorophenyl]-2-(3-benzylphenoxy)acetamide,
(1-2) N-[4-(aminosulfonyl)-2-chlorophenyl]-2-(3-phenoxyphenoxy)acetamide,
(2-1) N-[4-(aminosulfonyl)-2-chlorophenyl]-2-[3-chloro-5-(3-chloro-5-cyanophenoxy)phenoxy]acetamide,
(13-4) N-[4-(aminosulfonyl)-2-chlorophenyl]-2-{3-[(5-bromopyridin-3-yl)oxy]-5-chlorophenoxy}acetamide,
(11-4) N-[4-(aminosulfonyl)-2-chlorophenyl]-2-[3-chloro-5-(3,5-dicyanophenoxy)phenoxy]acetamide,
(15-2) 2-[3-chloro-5-(3-chloro-5-cyanophenoxy)phenoxy]-N-(2-chloro-4-cyanophenyl)acetamide,
(5-6) 2-[3-chloro-5-(3-chloro-5-cyanophenoxy)phenoxy]-N-[2-chloro-4-(methylsulfonyl)phenyl]acetamide,
(17-3) 3-chloro-4-({[3-chloro-5-(3-chloro-5-cyanophenoxy)phenoxy]acetyl}amino)benzamiide,
(19-2) N-(1H-benzimidazol-5-yl)-2-[3-chloro-5-(3-chloro-5-cyanophenoxy)phenoxy]acetamide,
(24-3) N-(4-chloro-1H-benzimidazol-5-yl)-2-[3-chloro-5-(3-chloro-5-cyanophenoxy)phenoxy]acetamide,
(21-2) 2-[3-chloro-5-(3-chloro-5-cyanophenoxy)phenoxy]-N-(1,1-dioxidotetrahydrothien-3-yl)acetamide
(22-2) 2-[3-chloro-5-(3-chloro-5-cyanophenoxy)phenoxy]-N-[(1,1-dioxidotetrahydrothien-3-yl)methyl]acetamide,
(25-4) 2-[4-chloro-3-(3-chloro-5-cyanophenoxy)phenoxy]-N-[2-chloro-4-(methylsulfonyl)phenyl]acetamide,
(27-5) 2-[4-chloro-3-(3-chloro-5-cyanophenoxy)phenoxy]-N-{4-[2-(dimethylamino)ethoxy]-2-methylphenyl}acetamide,
(28-2) 2-[4-chloro-3-(3-chloro-5-cyanophenoxy)phenoxy]-N-[3-(trifluoromethyl)pyridin-4-yl]acetamide,
(4-4) N-[4-(aminosulfonyl)-2-chlorophenyl]-2-[3-chloro-5-(3-cyanophenoxy)phenoxy]acetamide,
(10-4) N-[4-(aminosulfonyl)-2-chlorophenyl]-2-(3-chloro-5-phenoxyphenoxy)acetamide,
(8-4) N-[4-(aminosulfonyl)-2-chlorophenyl]-2-[3-(3-chloro-5-cyanophenoxy)-5-methylphenoxy]acetamide,
(6-1) N-[4-(aminosulfonyl)-2-chlorophenyl]-2-[4-chloro-3-(3-chloro-5-cyanophenoxy)phenoxy]acetamide,
(12-2) N$^1$-[4-(aminosulfonyl)-2-chlorophenyl]-N$^2$-(3-phenoxyphenyl)glycinamide,
(a1) N-[4-(aminosulfonyl)-2-chlorophenyl]-2-(3-phenoxyphenoxy)propanamide,
(a2) 2-[3-chloro-5-(3-chloro-5-cyanophenoxy)phenoxy]-N-[2-chloro-4-(methylsulfonyl)phenyl]-N-ethylacetamide,
(a3) 2-[3-chloro-5-(3-chloro-5-cyanophenoxy)phenoxy]-N-[2-chloro-4-(methylsulfonyl)phenyl]-N-methylacetamide,
(a4) N-{3-[(aminosulfonyl)amino]propyl}-2-[3-chloro-5-(3-chloro-5-cyanophenoxy)phenoxy]acetamide,
(a5) N-[4-(aminosulfonyl)-2-chlorophenyl]-2-(3-phenoxyphenoxy)acetamide, and
(a6) N-[4-(aminosulfonyl)-2-chlorophenyl]-2-[3-chloro-5-(3-chloro-5-cyanophenoxy)phenoxy]acetamide.

Each of the foregoing compounds individually, and the pharmaceutically acceptable salts thereof, is an aspect of the present invention.

An embodiment of the present invention (Embodiment E9) includes compounds of Formula Ib:

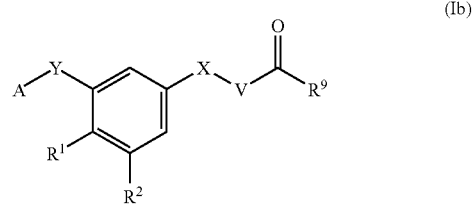

(Ib)

and pharmaceutically acceptable salts thereof, wherein all variables are as originally defined for Formula I.

Another embodiment of the present invention (Embodiment E10) is a compound of Formula Ib, or a pharmaceutically acceptable salt thereof, wherein:
X is selected from the group consisting of —O—, —NH—, and —CH$_2$—;
Y is selected from the group consisting of —O—, —CH$_2$—, and —S(O)$_m$—;
and all other variables are as defined in Embodiment E9.

Another embodiment of the present invention (Embodiment E11) is a compound of Formula Ib, or a pharmaceutically acceptable salt thereof, wherein:
X is —O— or —NH—;
Y is selected from the group consisting of —O—, —CH$_2$—, and —S(O)$_m$—;
R$^3$ and R$^4$ are independently selected from the group consisting of hydrogen, C$_{1-6}$ alkyl, and C$_{1-3}$ fluoroalkyl;
R$^5$ and R$^6$ are independently selected from the group consisting of hydrogen and C$_{1-6}$ alkyl;
R$^{11}$ is selected from the group consisting of hydrogen, halogen, NO$_2$, CN, OR$^3$, O(CH$_2$)$_t$OR$^3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, and C$_{1-6}$ alkyl;

and all other variables are as defined in Embodiment E9.

A preferred embodiment of the present invention (Embodiment E12) includes compounds of the Formula Ib, and pharmaceutically acceptable salts thereof, wherein R$^1$ and R$^2$ are independently selected from the group consisting of hydrogen or halogen;
A is aryl;
R$^9$ is selected from the group consisting of:

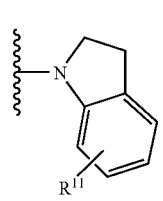 and 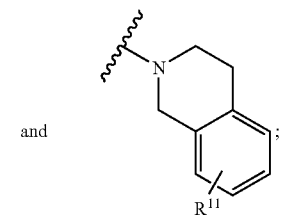;

V is —C(R$^5$R$^6$)—;
X is —O— or —NH—;

Y is selected from the group consisting of —O—, —CH$_2$—, and —S(O)$_m$—;

R$^5$ and R$^6$ are independently selected from the group consisting of hydrogen and C$_{1-6}$ alkyl; and all other variables are as defined in Embodiment E9.

A class of the preceding embodiment (Class C4) includes compounds of Formula Ib and pharmaceutically acceptable salts thereof, wherein:

R$^{11}$ is selected from the group consisting of hydrogen, halogen, NO$_2$, CN, OR$^3$, O(CH$_2$)$_t$OR$^3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, and C$_{1-6}$ alkyl; and R$^3$ and R$^4$ are independently selected from the group consisting of hydrogen, C$_{1-6}$ alkyl, and C$_{1-3}$ fluoroalkyl;

and all other variables are as defined in Embodiment E12.

A more preferred embodiment of the present invention (Embodiment E13) includes compounds of the Formula Ib, and pharmaceutically acceptable salts thereof, wherein V is —CH$_2$—;
X is —O—;
Y is —O—; and all other variables are as defined in Embodiment E12.

A class of the preceding embodiment (Class C5) includes compounds of Formula Ib and pharmaceutically acceptable salts thereof, wherein:

R$^{11}$ is selected from the group consisting of hydrogen, halogen, NO$_2$, CN, OR$^3$, O(CH$_2$)$_t$OR$^3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, and C$_{1-6}$ alkyl; and R$^3$ and R$^4$ are independently selected from the group consisting of hydrogen, C$_{1-6}$ alkyl, and C$_{1-3}$ fluoroalkyl;

and all other variables are as defined in Embodiment E13.

Specific examples of compounds of Formula Ib, and pharmaceutically acceptable salts thereof, include

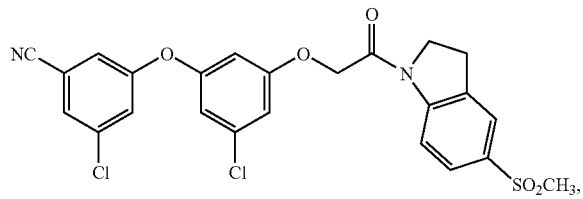

(20-2)

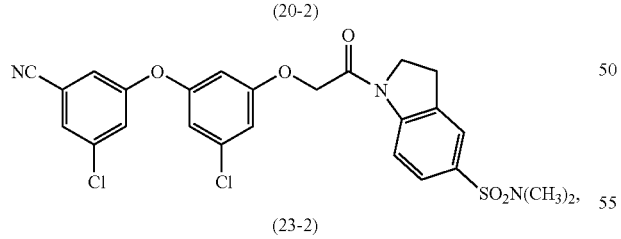

(23-2)

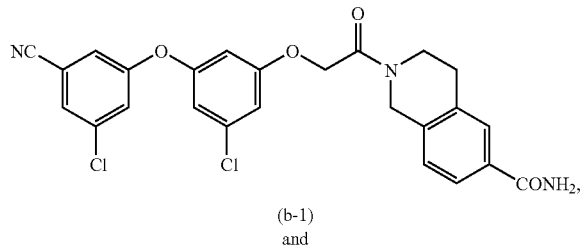

(b-1)
and

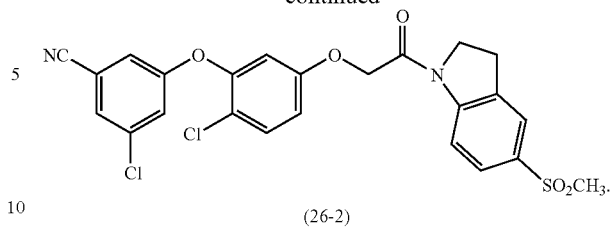

(26-2)

The compounds represented by the structures shown above have the following names:

(20-2) 3-chloro-5-(3-chloro-5-{2-[5-(methylsulfonyl)-2,3-dihydro-1H-indol-1-yl]-2-oxoethoxy}phenoxy)benzonitrile, (23-2) 1-{[3-chloro-5-(3-chloro-5-cyanophenoxy)phenoxy]acetyl}-N,N-dimethylindoline-5-sulfonamide, (26-2) 3-chloro-5-(2-chloro-5-{2-[5-(methylsulfonyl)-2,3-dihydro-1H-indol-1-yl]-2-oxoethoxy}phenoxy)benzonitrile, and (b1) 2-{[3-chloro-5-(3-chloro-5-cyanophenoxy)phenoxy]acetyl}-1,2,3,4-tetrahydroisoquinoline-6-carboxamide.

Each of the foregoing compounds individually, and the pharmaceutically acceptable salts thereof, is an aspect of the present invention.

An embodiment of the present invention (Embodiment E14) includes compounds of Formula Ic and pharmaceutically acceptable salts thereof:

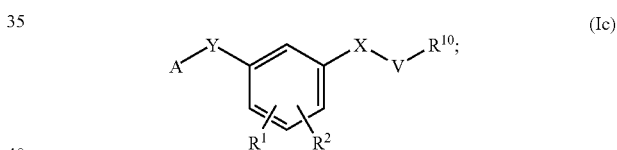

(Ic)

wherein all variables are as originally defined for Formula I or as defined in any one of Embodiments E1 to E4; and provided that when X is —C(R$^5$R$^6$)— (or an aspect thereof such as —CH$_2$—), then neither R$^1$ nor R$^2$ is OR$^3$.

An embodiment of the present invention (Embodiment E15) includes compounds of Formula Ic-1 and pharmaceutically acceptable salts thereof:

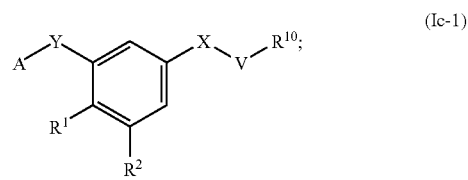

(Ic-1)

wherein all variables are as originally defined for Formula I or as defined in any one of Embodiments E1 to E4; and provided that when X is —C(R$^5$R$^6$)— (or an aspect thereof such as —CH$_2$—), then neither R$^1$ nor R$^2$ is OR$^3$.

An embodiment of the present invention (Embodiment E16) includes compounds of Formula Ic-2 and pharmaceutically acceptable salts thereof:

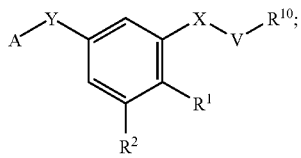

(Ic-2)

wherein all variables are as originally defined for Formula I or as defined in any one of Embodiments E1 to E4; and provided that (i) when X is —C($R^5R^6$)—, then neither $R^1$ nor $R^2$ is $OR^3$, and (ii) $R^1$ is other than H.

Another embodiment of the present invention (Embodiment E17) is a compound of Formula Ic, or a pharmaceutically acceptable salt thereof, wherein:
X is selected from the group consisting of —O—, —NH—, and —$CH_2$—;
Y is selected from the group consisting of —O—, —$CH_2$—, and —S(O)$_m$—;
and all other variables are as defined in Embodiment E14;

and provided that when X is —$CH_2$—, then neither $R^1$ nor $R^2$ is $OR^3$. A sub-embodiment is a compound of Formula Ic-1, or a pharmaceutically acceptable salt thereof, wherein all variables are as defined in Embodiment E17; and provided that when X is —$CH_2$—, then neither $R^1$ nor $R^2$ is $OR^3$. Another sub-embodiment is a compound of Formula Ic-2, or a pharmaceutically acceptable salt thereof, wherein all variables are as defined in Embodiment E17; and provided that (i) when X is —C($R^5R^6$)—, then neither $R^1$ nor $R^2$ is $OR^3$, and (ii) $R^1$ is other than H.

Another embodiment of the present invention (Embodiment E18) is a compound of Formula Ic, or a pharmaceutically acceptable salt thereof, wherein:
X is selected from the group consisting of —O— and —NH—;
Y is selected from the group consisting of —O—, —$CH_2$—, and —S(O)$_m$—;
$R^3$ and $R^4$ are independently selected from the group consisting of hydrogen, $C_{1-6}$ alkyl, and $C_{1-3}$ fluoroalkyl;
$R^5$ and $R^6$ are independently selected from the group consisting of hydrogen and $C_{1-6}$ alkyl;
$R^{10}$ is as originally defined or as defined in either Embodiment E1 or Embodiment E3;
$R^{12}$ and $R^{13}$ are independently selected from the group consisting of hydrogen, halogen, oxo, $NO_2$, CN, $OR^3$, $O(CH_2)_t$$CF_3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl and $C_{1-3}$ fluoroalkyl;

and all other variables are as originally defined for Formula I. A sub-embodiment is a compound of Formula Ic-1, or a pharmaceutically acceptable salt thereof, wherein all variables are as defined in Embodiment E18. Another sub-embodiment is a compound of Formula Ic-2, or a pharmaceutically acceptable salt thereof, wherein all variables are as defined in Embodiment E18; and provided that $R^1$ is other than H.

A class of the preceding embodiment (Class C6) includes compounds of Formula Ic-1 and pharmaceutically acceptable salts thereof, wherein $R^{10}$ is as defined in Embodiment E1; and all other variables are as defined in Embodiment E18.

A preferred embodiment of the present invention (Embodiment E19) includes compounds of Formula Ic, and pharmaceutically acceptable salts thereof, wherein:

$R^1$ and $R^2$ are independently selected from the group consisting of hydrogen, halogen, and $C_{1-6}$ alkyl;
A is aryl;
$R^{10}$ is selected from the group consisting of:

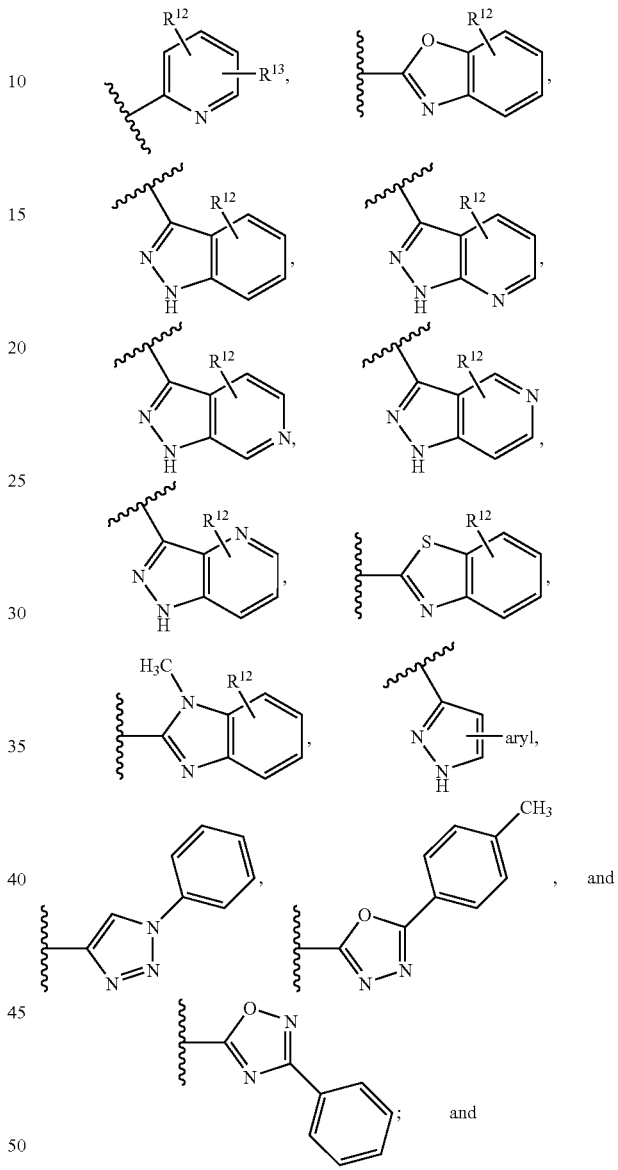

$R^{12}$ and $R^{13}$ are independently selected from the group consisting of hydrogen, halogen, oxo, $NO_2$, CN, $OR^3$, $O(CH_2)_t$$CF_3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl, $C_{1-3}$ fluoroalkyl, and $NR^3R^4$;

and all other variables are as originally defined for Formula I. A sub-embodiment is a compound of Formula Ic-1, or a pharmaceutically acceptable salt thereof, wherein all variables are as defined in Embodiment E19. Another sub-embodiment is a compound of Formula Ic-2, or a pharmaceutically acceptable salt thereof, wherein all variables are as defined in Embodiment E19; and provided that $R^1$ is halogen or $C_{1-6}$ alkyl.

A preferred embodiment of the present invention (Embodiment E20) includes compounds of the Formula Ic, and pharmaceutically acceptable salts thereof, wherein:

$R^5$ and $R^6$ are independently selected from the group consisting of hydrogen and $C_{1-6}$ alkyl;

$R^{12}$ and $R^{13}$ are independently selected from the group consisting of hydrogen, halogen, oxo, $NO_2$, CN, $OR^3$, $O(CH_2)_t CF_3$, $CO_2R^3$, $CONR^3R^4$, $O(CH_2)_t NR^3R^4$, $O(CH_2)_v COR^3$, $S(O)_m R^3$, $SO_2NR^3R^4$, $C_{1-6}$ alkyl, and $C_{1-3}$ fluoroalkyl;

$R^3$ and $R^4$ are independently selected from the group consisting of hydrogen, $C_{1-6}$ alkyl, and $C_{1-3}$ fluoroalkyl; and $R^1$, $R^2$, A and $R^{10}$ are each as defined in Embodiment E19. A sub-embodiment is a compound of Formula Ic-1, or a pharmaceutically acceptable salt thereof, wherein all variables are as defined in Embodiment E20. Another sub-embodiment is a compound of Formula Ic-2, or a pharmaceutically acceptable salt thereof, wherein all variables are as defined in Embodiment E20; and provided that $R^1$ is halogen or $C_{1-6}$ alkyl.

A class of the preceding embodiment (Class C7) includes compounds of Formula Ic and pharmaceutically acceptable salts thereof, wherein X is —O— or —NH—; Y is selected from the group consisting of —O—, —CH$_2$—, and —S(O)$_m$—; and all other variables are as defined in Embodiment E20. A first sub-class of Class C7 (SC7-1) includes compounds of Formula Ic-1 and pharmaceutically acceptable salts thereof, wherein all variables are as defined in Class C7. A second sub-class of Class C7 (SC7-2) includes compounds of Formula Ic-2 and pharmaceutically acceptable salts thereof, wherein all variables are as defined in Class C7; and provided that $R^1$ is halogen or $C_{1-6}$ alkyl.

Another class of the preceding embodiment (Class C8) includes compounds of Formula Ic and pharmaceutically acceptable salts thereof, wherein V is —CH$_2$—; X is —O—; Y is —O—; and all other variables are as defined in Embodiment E20. A first sub-class of Class C8 (SC8-1) includes compounds of Formula Ic-1, and pharmaceutically acceptable salts thereof, wherein all variables are as defined in Class C8. A second sub-class of Class C8 (SC8-2) includes compounds of Formula Ic-2 and pharmaceutically acceptable salts thereof, wherein all variables are as defined in Class C8; and provided that $R^1$ is halogen or $C_{1-6}$ alkyl.

A more preferred embodiment of the present invention (Embodiment E21) includes compounds of Formula Ic, and pharmaceutically acceptable salts thereof, wherein:

V is —CH$_2$—;
X is —O—;
Y is —O—;
$R^{10}$ is selected from the group consisting of:

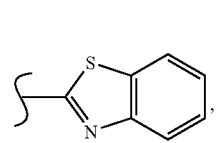, ,

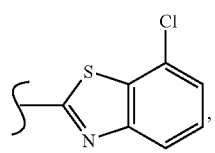, 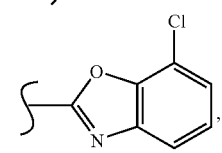,

-continued

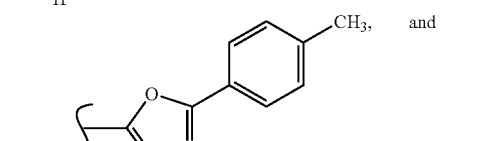

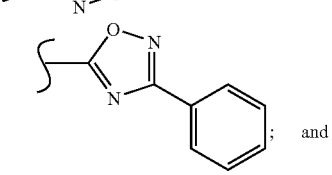; and $R^1$, $R^2$, and A are each as defined in Embodiment E20. A sub-embodiment is a compound of Formula Ic-1, or a pharmaceutically acceptable salt thereof, wherein all variables are as defined in Embodiment E21. Another sub-embodiment is a compound of Formula Ic-2, or a pharmaceutically acceptable salt thereof, wherein all variables are as defined in Embodiment E21; and provided that $R^1$ is halogen or $C_{1-6}$ alkyl.

A class of the preceding embodiment (Class C9) includes compounds of Formula Ic-1 and pharmaceutically acceptable salts thereof wherein $R^{10}$ is selected from the group consisting of:

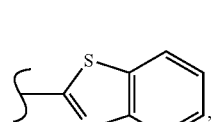, 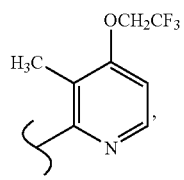,

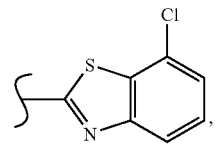, 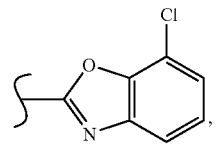,

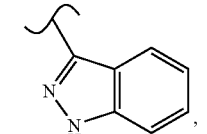, 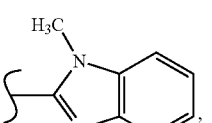,

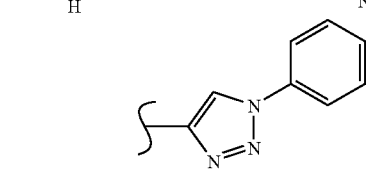,

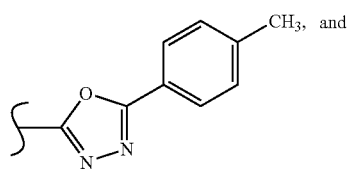
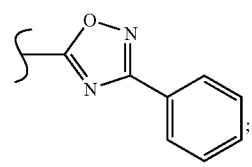
and all other variables are as defined in the preceding embodiment (E21).
Specific examples of compounds of Formula Ic, and pharmaceutically acceptable salts thereof, include
(3-2)
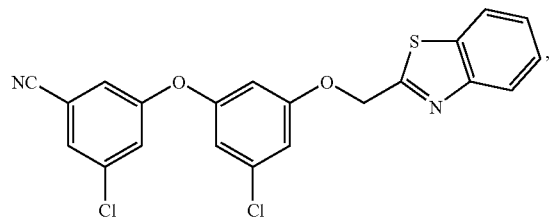
(c1)
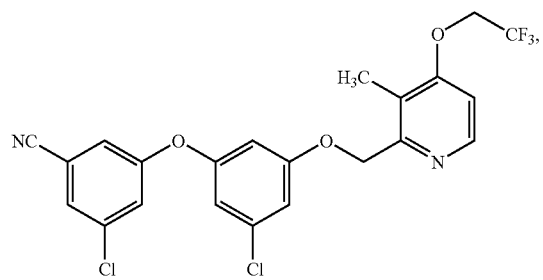
(9-1)
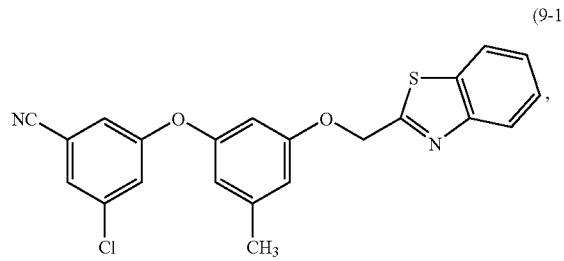
(7-1)
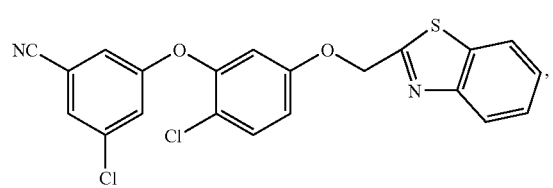
(16-6)
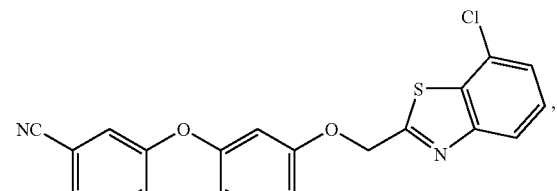
(18-1)
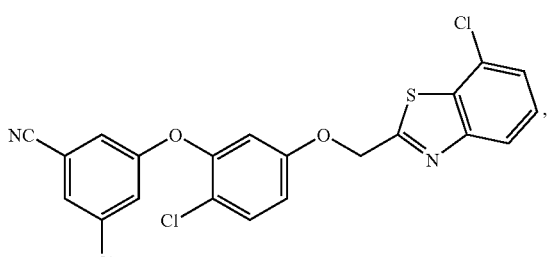
(29-2)
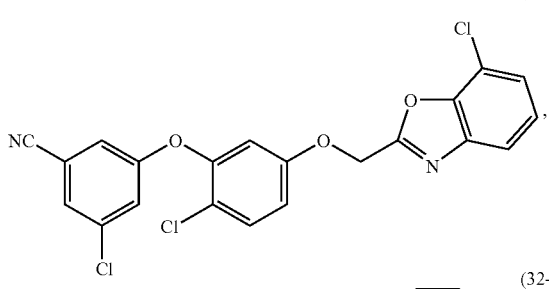
(32-6)
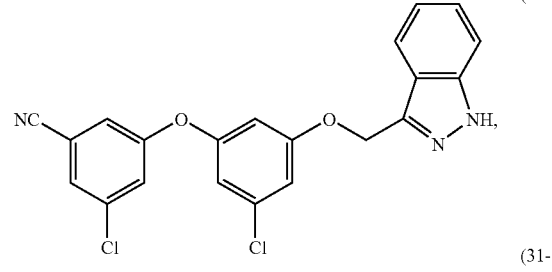
(31-2)
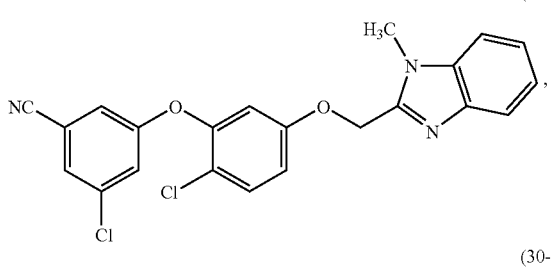
(30-2)
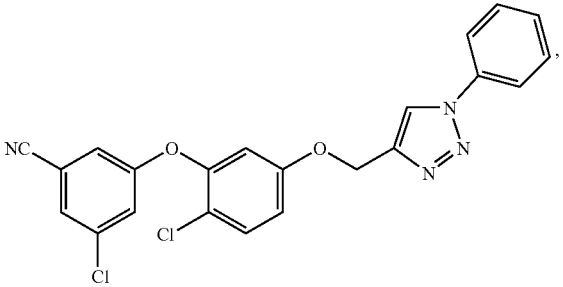

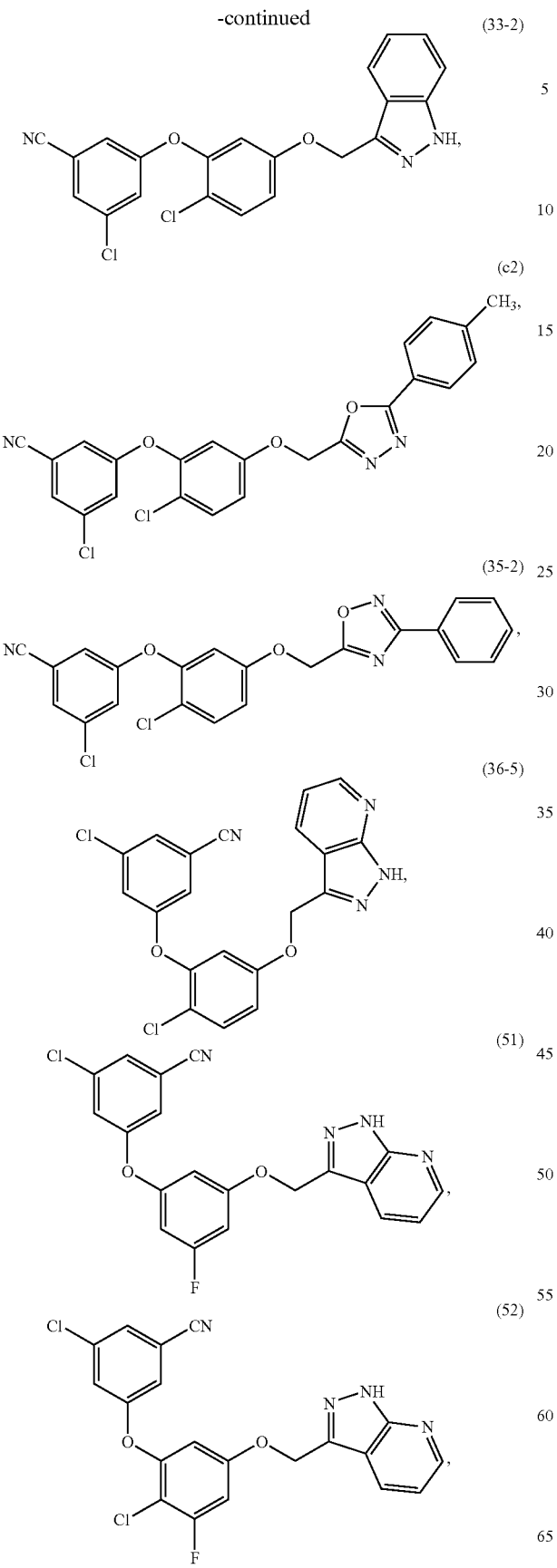
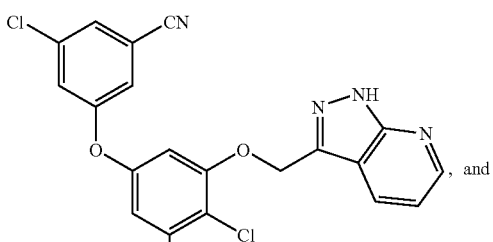

The compounds represented by the structures shown above have the following names:

(3-2) 3-[3-(1,3-benzothiazol-2-ylmethoxy)-5-chlorophenoxy]-5-chlorobenzonitrile,
(9-1) 3-[3-(1,3-benzothiazol-2-ylmethoxy)-5-methylphenoxy]-5-chlorobenzonitrile,
(7-1) 3-[5-(1,3-benzothiazol-2-ylmethoxy)-2-chlorophenoxy]-5-chlorobenzonitrile,
(16-6) 3-chloro-5-{3-chloro-5-[(7-chloro-1,3-benzothiazol-2-yl)methoxy]phenoxy}benzonitrile,
(18-1) 3-chloro-5-{2-chloro-5-[(7-chloro-1,3-benzothiazol-2-yl)methoxy]phenoxy}benzonitrile,
(29-2) 3-chloro-5-{2-chloro-5-[(7-chloro-1,3-benzoxazol-2-yl)methoxy]phenoxy}benzonitrile,
(32-6) 3-chloro-5-[3-chloro-5-(1H-indazol-3-ylmethoxy)phenoxy]benzonitrile,
(31-2) 3-chloro-5-{2-chloro-5-[(1-methyl-1H-benzimidazol-2-yl)methoxy]phenoxy}benzonitrile,
(30-2) 3-chloro-5-{2-chloro-5-[(1-phenyl-1H-1,2,3-triazol-4-yl)methoxy]phenoxy}benzonitrile,
(33-2) 3-chloro-5-[2-chloro-5-(1H-indazol-3-ylmethoxy)phenoxy]benzonitrile,
(35-2) 3-chloro-5-{2-chloro-5-[(3-phenyl-1,2,4-oxadiazol-5-yl)methoxy]phenoxy}benzonitrile,
(36-5) 3-chloro-5-[2-chloro-5-(1H-pyrazolo[3,4-b]pyridin-3-ylmethoxy)phenoxy]benzonitrile,
(c1) 3-chloro-5-(3-chloro-5-{[3-methyl-4-(2,2,2-trifluoroethoxy)pyridin-2-yl]methoxy}phenoxy)-benzonitrile,
(c2) 3-chloro-5-(2-chloro-5-{[5-(4-methylphenyl)-1,3,4-oxadiazol-2-yl]methoxy}phenoxy)benzonitrile,
(51) 3-{5-[(1H-pyrazolo[3,4-b]pyridin-3-yl)methoxy]-3-fluorophenoxy}-5-chlorobenzonitrile),
(52) 3-{5-[(1H-pyrazolo[3,4-b]pyridin-3-yl)methoxy]-2-chloro-3-fluorophenoxy}-5-chlorobenzonitrile,
(53) 3-{5-[(1H-pyrazolo[3,4-b]pyridin-3-yl)methoxy]-4-chloro-3-fluorophenoxy}-5-chlorobenzonitrile, and
(54) 3-{5-[(7-oxo-1H-pyrazolo[3,4-b]pyridin-3-yl)methoxy]-4-chloro-3-fluorophenoxy}-5-chlorobenzonitrile.

Each of the foregoing compounds individually, and the pharmaceutically acceptable salts thereof, is an aspect of the present invention.

Another embodiment of the present invention (Embodiment E22) is a compound of Formula Ic, or a pharmaceutically acceptable salt thereof, wherein:

$R^1$ and $R^2$ are each independently selected from the group consisting of hydrogen, halogen, and $C_{1-4}$ alkyl;

A is phenyl optionally substituted with from 1 to 3 substituents each of which is independently halogen, $C_{1-4}$ alkyl, or CN;

V is —$CH_2$—;
X is —O—;
Y is —O—;

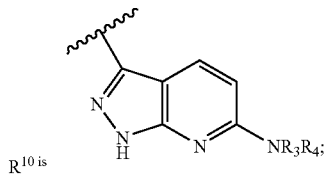

$R^{10}$ is one of $R^3$ and $R^4$ is H, $C_{1-4}$ alkyl, or $C_{3-6}$ cycloalkyl, and the other of $R^3$ and $R^4$ is H, $C_{1-4}$ alkyl, or $C_{1-4}$ alkyl substituted with O—$C_{1-4}$ alkyl, $C(O)R^A$, $CO_2R^A$, $C(O)N(R^A)R^B$, or $SO_2R^A$;

or alternatively $R^3$ and $R^4$ together with the nitrogen atom to which they are both attached form a 4- to 7-membered, saturated monocyclic ring optionally containing 1 heteroatom in addition to the nitrogen attached to $R^3$ and $R^4$ selected from N, O, and S, where the S is optionally oxidized to S(O) or $S(O)_2$, wherein the monocyclic ring is optionally substituted with 1 or 2 substituents each of which is independently: (1) $C_{1-4}$ alkyl, (2) $CF_3$, (3) $(CH_2)_{1-2}T$ wherein T is OH, O—$C_{1-4}$ alkyl, $OCF_3$, $N(R^A)R^B$, $C(O)N(R^A)R^B$, $C(O)R^A$, $CO_2R^A$, or $SO_2R^A$, (4) O—$C_{1-4}$ alkyl, (5) $OCF_3$, (6) OH, (7) oxo, (8) halogen, (9) $C(O)N(R^A)R^B$, (10) $C(O)R^A$, (11) $C(O)$—$CF_3$, (12) $C(O)OR^A$, or (13) $S(O)_2R^A$;

each $R^A$ is independently H or $C_{1-4}$ alkyl, and each $R^B$ is independently H or $C_{1-4}$ alkyl. A sub-embodiment is a compound of Formula Ic-1, or a pharmaceutically acceptable salt thereof, wherein all variables are as defined in Embodiment E22. Another sub-embodiment is a compound of Formula Ic-2, or a pharmaceutically acceptable salt thereof, wherein all variables are as defined in Embodiment E22; and provided that $R^1$ is halogen or $C_{1-4}$ alkyl.

Another embodiment of the present invention (Embodiment E23) is a compound of Formula Ic, or a pharmaceutically acceptable salt thereof, selected from the group consisting of:

3-{5-[(6-amino-1H-pyrazolo[3,4-b]pyridin-3-yl)methoxy]-2-chlorophenoxy}-5-chlorobenzonitrile,
3-chloro-5-(2-chloro-5-{[6-methylamino)-1H-pyrazolo[3,4-b]-pyridin-3-yl]methoxy}phenoxy)benzonitrile,
3-chloro-5-(2-chloro-5-{[6-dimethylamino)-1H-pyrazolo[3,4-b]-pyridin-3-yl]methoxy}phenoxy)benzonitrile,
3-chloro-5-[2-chloro-5-({6-[(2-methoxyethyl)(methyl)amino]-1H-pyrazolo[3,4-b]-pyridin-3-yl}methoxy)phenoxy)benzonitrile,
3-chloro-5-(2-chloro-5-[(6-morpholin-4-yl-1H-pyrazolo[3,4-b]-pyridin-3-yl]methoxy]phenoxy)benzonitrile,
N2-(3-{[4-chloro-3-(3-chloro-5-cyanophenoxy)phenoxy]methyl}-1H-pyrazolo[3,4-b]pyridin-6-yl)-N2-methylglycinamide,
3-chloro-5-(2-chloro-5-{[6-(3-methoxyazetidin-1-yl)-1H-pyrazolo[3,4-b]-pyridin-3-yl]methoxy}phenoxy)benzonitrile,
3-chloro-5-(2-chloro-5-{[6-(azetidin-1-yl)-1H-pyrazolo[3,4-b]-pyridin-3-yl]methoxy}phenoxy)benzonitrile,
3-chloro-5-{2-chloro-5-[(6-piperazin-1-yl-1H-pyrazolo[3,4-b]-pyridin-3-yl]methoxy]phenoxy}benzonitrile,
3-(5-{[6-(3-aminopyrrolidin-1-yl)-1H-pyrazolo[3,4-b]-pyridin-3-yl]methoxy}-2-chlorophenoxy)-5-chlorobenzonitrile,
3-[5-({6-[3-(aminomethyl)azetidin-1-yl]-1H-pyrazolo[3,4-b]-pyridin-3-yl}methoxy)-2-chlorophenoxy]-5-chlorobenzonitrile,
3-(5-{[6-(3-aminoazetidin-1-yl)-1H-pyrazolo[3,4-b]-pyridin-3-yl]methoxy}-2-chlorophenoxy)-5-chlorobenzonitrile,
3-{5-[(6-amino-1H-pyrazolo[3,4-b]pyridin-3-yl)methoxy]-2-chloro-3-fluorophenoxy}-5-chlorobenzonitrile,
3-{5-[(6-amino-1H-pyrazolo[3,4-b]pyridin-3-yl)methoxy]-3-fluorophenoxy}-5-chlorobenzonitrile, and
3-{5-[(6-amino-1H-pyrazolo[3,4-b]pyridin-3-yl)methoxy]-4-chloro-3-fluorophenoxy}-5-chlorobenzonitrile.

Each of the foregoing compounds individually, and the pharmaceutically acceptable salts thereof, is an aspect of the present invention.

Another embodiment of the present invention (Embodiment E24) is a compound of Formula Ic, or a pharmaceutically acceptable salt thereof, wherein:

$R^1$ and $R^2$ are each independently selected from the group consisting of hydrogen, halogen, and $C_{1-4}$ alkyl;

A is phenyl optionally substituted with from 1 to 3 substituents each of which is independently halogen, $C_{1-4}$ alkyl, or CN;

V is —$CH_2$—;
X is —$CH_2$—;
Y is —O—; and

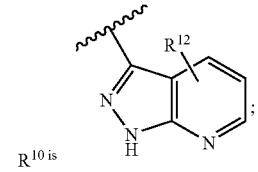

$R^{10}$ is and provided that when the compound is a compound of Formula Ic-2, then $R^1$ is halogen or $C_{1-4}$ alkyl. A sub-embodiment is a compound of Formula Ic-1, or a pharmaceutically acceptable salt thereof, wherein all variables are as defined in Embodiment E24. Another sub-embodiment is a compound of Formula Ic-2, or a pharmaceutically acceptable salt thereof, wherein all variables are as defined in Embodiment E24; and provided that $R^1$ is halogen or $C_{1-4}$ alkyl.

Another embodiment of the present invention (E25) is a compound of Formula Ic-1, or a pharmaceutically acceptable salt thereof, wherein the compound is 3-chloro-5-{2-chloro-5-[2-(1H-pyrazolo[3,4-b]pyridin-3-yl)ethyl]phenoxy}benzonitrile.

A class of compounds of the present invention (Class C10) includes compounds of Formula I and their pharmaceutically acceptable salts, wherein all of the variables and provisos are as originally defined above, except that A is aryl optionally substituted with from 1 to 3 substituents each of which is independently halo, $C_1$-$C_6$ alkyl, $CF_3$, $NH_2$, —$NH(C_1$-$C_6$ alkyl), —$N(C_1$-$C_6$ alkyl)$_2$, —$NO_2$, —CN, —OH, —O—($C_1$-$C_6$ alkyl), $C_3$-$C_6$ cycloalkyl, $C_2$-$C_6$ alkenyl, $C_2$-$C_6$ alkynyl, —$S(O)_{0-2}(C_1$-$C_6$ alkyl), —($C_1$-$C_6$ alkylene)-$S(O)_{0-2}(C_1$-$C_6$ alkyl), —$NHC(O)(C_1$-$C_6$ alkyl), —$C(=NH)NH_2$, —$O(C_1$-

$C_6$ alkylene)$CF_3$, —C(O)($C_1$-$C_6$ alkyl), —C(O)H, —OC(O)($C_1$-$C_6$ alkyl), —($C_1$-$C_6$ alkylene)O($C_1$-$C_6$ alkyl), —C(O)$NH_2$, —C(O)NH($C_1$-$C_6$ alkyl), —C(O)N($C_1$-$C_6$ alkyl)$_2$, —C(O)$_2$H, —C(O)$_2$($C_1$-$C_6$ alkyl), —($C_1$-$C_6$ alkylene)C(O)$_{1-2}$($C_1$-$C_6$ alkyl), —NHC(O)O—($C_1$-$C_6$ alkyl), —NH($C_1$-$C_6$ alkyl)NHC(O)NH($C_1$-$C_6$ alkyl), —NHSO$_2$NH$_2$, —NH($C_1$-$C_6$ alkyl)NHSO$_2$($C_1$-$C_6$ alkyl), —NHSO$_2$($C_1$-$C_6$ alkyl), —($C_1$-$C_6$ alkyl)NHSO$_2$($C_1$-$C_6$ alkyl), phenyl, or benzyl.

A sub-class of Class C10 (SC10) includes compounds of Formula I and their pharmaceutically acceptable salts, wherein all of the variables are as originally defined for Class C10, except that A is phenyl or naphthyl, wherein the phenyl or naphthyl is optionally substituted with from 1 to 3 substituents each of which is independently Cl, Br, F, $CH_3$, $CF_3$, $NH_2$, —NH($CH_3$), —N($CH_3$)$_2$, —CN, —OH, —OCH$_3$, cyclohexyl, ethenyl, ethynyl, —SCH$_3$, —S(O)$_2$CH$_3$, —(CH$_2$)$_{1-2}$—SCH$_3$, —(CH$_2$)$_{1-2}$—S(O)$_2$CH$_3$, —NHC(O)CH$_3$, —O(CH$_2$)$_{1-2}$CF$_3$, —C(O)CH$_3$, —OC(O)CH$_3$, —(CH$_2$)$_{1-2}$OCH$_3$, —C(O)NH$_2$, —C(O)NHCH$_3$, —C(O)N(CH$_{32}$, —C(O)$_2$H, —C(O)$_2$CH$_3$, —(CH$_2$)$_{1-2}$C(O)$_2$CH$_3$, —NHC(O)OCH$_3$, —NH(CH$_3$)NHC(O)NH(CH$_3$), phenyl, or benzyl.

Other classes of the present invention are compounds of Formula I and their pharmaceutically acceptable salts, wherein all of the variables (and applicable provisos) are as defined in Embodiments E1 to E7 and E9 to E21 respectively, except that A is an optionally substituted aryl as defined in Class C10. Other sub-classes of the present invention are compounds of Formula I and their pharmaceutically acceptable salts, wherein all of the variables (and applicable provisos) are as defined in Embodiments E1 to E7 and E9 to E21 respectively, except that A is an optionally substituted phenyl or optionally substituted naphthyl as defined in sub-class SC10.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —CH$_2$C(O)— groups (keto forms) may undergo tautomerism to form hydroxyl —CH═C(OH)— groups (enol forms). Both keto and enol forms are included within the scope of the present invention.

In addition compounds with carbon-carbon double bonds may occur in Z- and E-forms with all isomeric forms of the compounds being included in the present invention.

Another embodiment of the present invention is a compound of Formula I, or a pharmaceutically acceptable salt thereof, as originally defined or as defined in any of the foregoing embodiments, sub-embodiments, aspects, classes, or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. A compound or salt of 100% purity is one which is free of detectable impurities as determined by one or more standard methods of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Abbreviations employed herein include the following: AIDS=acquired immunodeficiency syndrome; BOC (or Boc)=t-butyloxycarbonyl; DCM=dichloromethane; dGTP=deoxyguanosine triphosphate; DIEA=diisopropylethylamine; DMAP=dimethylaminopyridine; DMF=dimethylformamide; DMSO=dimethyl sulfoxide; dNTP=deoxynucleoside triphosphate; EDC=1-ethyl-3-(3-dimethylaminopropyl carbodiimide hydrochloride; EGTA=ethylene glycol bis(2-aminoethyl ether)-N,N,N',N'-tetraacetic acid; EtOAc=ethyl acetate; HOBT=1-hydroxybenzotriazole hydrate; HRMS=high resolution mass spectroscopy; LC=liquid chromatography; MeOH=methanol; MTBE=methyl t-butyl ether; NBS=N-bromosuccinimide; NMP=N-methylpyrrolidinone; NMR=nuclear magnetic resonance; TBAF=tetrabutylammonium fluoride; TEA=triethylamine; Tf=trifluoromethanesulfonic (triflic); TFA=trifluoroacetic acid; THF=tetrahydrofuran; TMS=trimethylsilyl; UV=ultraviolet.

Other embodiments of the present invention include the following:

(a) A pharmaceutical composition comprising an effective amount of Compound I, or a pharmaceutically acceptable salt thereof, and a pharmaceutically acceptable carrier.

(b) A pharmaceutical composition which comprises the product prepared by combining (e.g., mixing) an effective amount of Compound I, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors other than a compound of Formula I, and HIV integrase inhibitors.

(e) A pharmaceutical combination which is (i) a compound of Formula I, or a pharmaceutically acceptable salt thereof, and (ii) an anti HIV agent selected from the group consisting of HIV antiviral agents, immunomodulators, and anti-infective agents; wherein the compound of Formula I and the anti-HIV agent are each employed in an amount that renders the combination effective for inhibiting HIV reverse transcriptase, for treating or prophylaxis of infection by HIV, or for treating, prophylaxis of, or delaying the onset of AIDS.

(f) The combination of (e), wherein the anti-HIV agent is an antiviral selected from the group consisting of HIV protease inhibitors, HIV reverse transcriptase inhibitors other than a compound of Formula I, and HIV integrase inhibitors.

Additional embodiments of the invention include the pharmaceutical compositions and combinations set forth in (a)-(f) above, wherein the compound of the present invention employed therein is a compound defined in one of the embodiments, sub-embodiments, aspects, classes, or sub-classes described above. In all of these embodiments, sub-embodiments, aspects, classes and sub-classes, the compound can optionally be used in the form of a pharmaceutically acceptable salt.

The present invention also includes a method (alternatively referred to herein as "Method M" of the present invention) for inhibiting HIV reverse transcriptase, for treating or prophylaxis of HIV infection, or for treating, prophylaxis of, or delaying the onset of AIDS, which comprises administering to a subject in need thereof an effective amount of a compound of Formula I', or a pharmaceutically acceptable salt thereof, wherein Formula I' is:

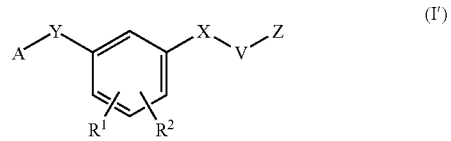

(I')

wherein $R^1$, $R^2$, A, V, X and Y and the variables defined therein (i.e., $R^3$, $R^4$, $R^5$, $R^6$, $R^7$, $R^8$, $R^9$, $R^{11}$, $R^{12}$, $R^{13}$, $R^A$, $R^B$, HetA and the integers s, q, t, v and m) have the same definitions as originally set forth above for compounds of Formula I;

Z is selected from the group consisting of —C(O)NR$^7$R$^8$, —C(O)R$^9$, and R$^{10}$; and R$^{10}$ is heterocyclyl.

The definition of Formula I' is similar to but broader in scope than that of Formula I set forth above; i.e., (i) R$^{10}$ as defined in Formula I' is heterocyclyl, whereas R$^{10}$ in the definition of Formula I is restricted to certain heterocyclic groups, and (ii) the definition of Formula I' does not include provisos A and B. Compounds within the scope of Formula I' but not embraced by Formula I are also reverse transcriptase inhibitors.

An embodiment of Method M (alternatively referred to as "Embodiment M1") is Method M as just described, wherein the compound of Formula I', or a pharmaceutically acceptable salt thereof, is defined as follows:

X is selected from the group consisting of —O—, —NH—, and —CH$_2$—;

Y is selected from the group consisting of —O—, —CH$_2$—, and —S(O)$_m$—;

and all other variables are as defined above in Formula I' in Method M as originally set forth.

Another embodiment of Method M (Embodiment M2) is Method M as just described, wherein the compound of Formula I', or a pharmaceutically acceptable salt thereof, is defined as follows:

X is selected from the group consisting of —O— and —NH—;

Y is selected from the group consisting of —O—, —CH$_2$—, and —S(O)$_m$—;

R$^{11}$ is selected from the group consisting of hydrogen, halogen, oxo, NO$_2$, CN, OR$^3$, O(CH$_2$)$_t$OR$^3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, and C$_{1-6}$ alkyl;

R$^3$ and R$^4$ are independently selected from the group consisting of hydrogen, C$_{1-6}$ alkyl, and C$_{1-3}$ fluoroalkyl;

R$^5$ and R$^6$ are independently selected from the group consisting of hydrogen and C$_{1-6}$ alkyl; and all other variables are as defined above in Formula I' in Method M as originally set forth.

Another embodiment of the present invention (Embodiment M3) is Method M as originally described, wherein the administered compound is a compound of Formula Ia', or a pharmaceutically acceptable salt thereof:

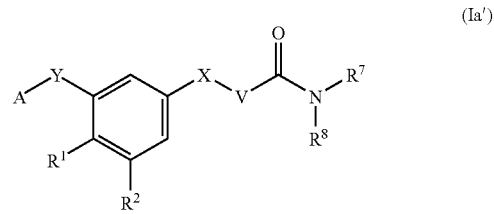

(Ia')

wherein all variables are as defined above in Formula I' in Method M as originally described or as defined in either Embodiment M1 or Embodiment M2.

Another embodiment of the present invention (Embodiment M4) is Method M as originally described, wherein the administered compound is a compound of Formula Ib', or a pharmaceutically acceptable salt thereof:

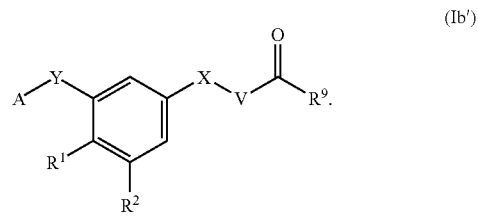

(Ib')

wherein all variables are as defined above in Formula I' in Method M as originally described or as defined in either Embodiment M1 or Embodiment M2.

Another embodiment of the present invention (Embodiment M5) is Method M as originally described, wherein the administered compound is a compound of Formula Ic', or a pharmaceutically acceptable salt thereof:

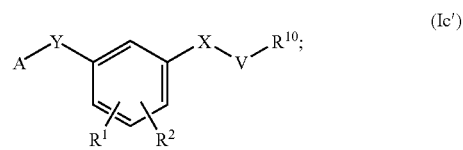

(Ic')

wherein all variables are as defined above in Formula I' in Method M as originally described or as defined in either Embodiment M1 or Embodiment M2.

Another embodiment of the present invention (Embodiment M6) is Method M as originally described, wherein the administered compound is a compound of Formula Ic'-1, or a pharmaceutically acceptable salt thereof:

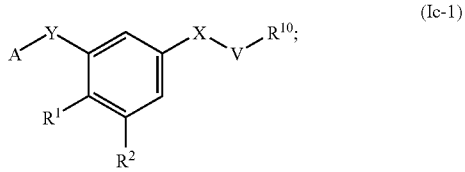

wherein all variables are as defined above in Formula I' in Method M as originally described or as defined in either Embodiment M1 or Embodiment M2.

Another embodiment of the present invention (Embodiment M7) is Method M as originally described, wherein the administered compound is a compound of Formula Ic'-2, or a pharmaceutically acceptable salt thereof:

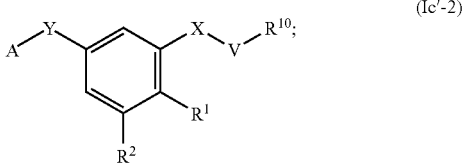

wherein all variables are as defined above in Formula I' in Method M as originally described or as defined in either Embodiment M1 or Embodiment M2.

Other embodiments of the method of the present invention include those in which the compound of Formula I' administered to the subject is the compound of Formula I, or a pharmaceutically acceptable salt thereof, as originally defined above in the Summary of the Invention or as defined in the compound embodiments, sub-embodiments, aspects, classes and sub-classes set forth above.

The present invention also includes a compound of Formula I', or a pharmaceutically acceptable salt thereof, (i) for use in, (ii) for use as a medicament for, or (iii) for use in the preparation of a medicament for: (a) inhibiting HIV reverse transcriptase, (b) treating or prophylaxis of infection by HIV, or (c) treating, prophylaxis of, or delaying the onset of AIDS. In these uses, the compound of Formula I' is as originally set forth and defined above. In these uses, the compounds of Formula I' can optionally be employed in combination with one or more anti-HIV agents selected from HIV antiviral agents, anti-infective agents, and immunomodulators. Embodiments of the uses of the present invention include those in which the compound of Formula I' is as defined in the embodiments set forth above.

Still other embodiments of the present invention include the following:

(a') A pharmaceutical composition comprising an effective amount of Compound I', or a pharmaceutically acceptable salt thereof; an effective amount of an anti-HIV agent selected from the group consisting of HIV antiviral agents, immunomodulators, and anti-infective agents; and a pharmaceutically acceptable carrier.

(b') The pharmaceutical composition of (a'), wherein the anti-HIV agent is an antiviral selected from the group consisting of HIV protease inhibitors, HIV reverse transcriptase inhibitors other than a compound of Formula I', and HIV integrase inhibitors.

(c') A pharmaceutical combination which is (i) a compound of Formula I', or a pharmaceutically acceptable salt thereof, and (ii) an anti-HIV agent selected from the group consisting of HIV antiviral agents, immunomodulators, and anti-infective agents; wherein the compound of Formula I' and the anti-HIV agent are each employed in an amount that renders the combination effective for inhibiting HIV reverse transcriptase, for treating or prophylaxis of infection by HIV, or for treating, prophylaxis of, or delaying the onset of AIDS.

(d') The combination of (c'), wherein the anti-HIV agent is an antiviral selected from the group consisting of HIV protease inhibitors, HIV reverse transcriptase inhibitors other than a compound of Formula I', and HIV integrase inhibitors.

Additional embodiments of the invention include the pharmaceutical compositions and combinations set forth in (a')-(d') above, wherein the compound of the present invention employed therein is a compound defined in one of the embodiments of Formula I' as described above. In all of these embodiments, the compound can optionally be used in the form of a pharmaceutically acceptable salt.

The present invention also includes prodrugs of the compounds of Formula I'. The term "prodrug" refers to a derivative of a compound of Formula I', or a pharmaceutically acceptable salt thereof, which is converted in vivo into Compound I'. Prodrugs of compounds of Formula I' can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). The prodrug can be, for example, a derivative of a hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

An embodiment of the present invention (alternatively referred to as "Embodiment PD1") is a prodrug of a compound of Formula I as originally defined above.

Another embodiment of the present invention (Embodiment PD2) is a compound of Formula I-P:

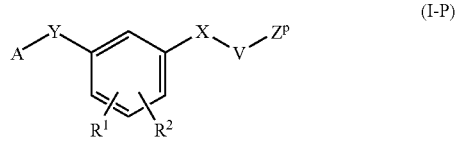

wherein:
R$^1$ and R$^2$ are independently selected from the group consisting of:
a) H,
b) C$_{1-6}$ alkyl,
c) C$_{3-6}$ cycloalkyl, d) $C_{1-3}$ fluoroalkyl,
e) $NO_2$,
f) halogen,
g) $OR^3$,
h) $O(CH_2)_sOR^3$,
i) $CO_2R^3$,
j) $(CO)NR^3R^4$,
k) $O(CO)NR^3R^4$,
l) $N(R^3)(CO)NR^3R^4$,
m) $N(R^3)(CO)R^4$,
n) $N(R^3)(CO)OR^3$,
o) $SO_2NR^3R^4$,
p) $N(R^3)SO_2R^4$,
q) $S(O)_mR^3$,
r) CN,
s) $NR^3R^4$,
t) $N(R^3)(CO)NR^3R^4$, and
u) $O(CO)R^3$;

A is aryl, $C_{3-7}$ cycloalkyl, or heterocyclyl;
V is $—C(R^5R^6)—$;
X is selected from the group consisting of $—O—$, $—NH—$, and $—C(R^5R^6)—$;
Y is selected from the group consisting of $—O—$, $—C(R^5R^6)—$, and $—S(O)_m—$;
$Z^P$ is $R^{10}*$;
$R^5$ and $R^6$ are independently selected from the group consisting of hydrogen, $C_{1-6}$ alkyl, $C_{1-3}$ fluoroalkyl, and $OR^3$;
$R^{10}*$ is a heterocycle selected from the group consisting of:

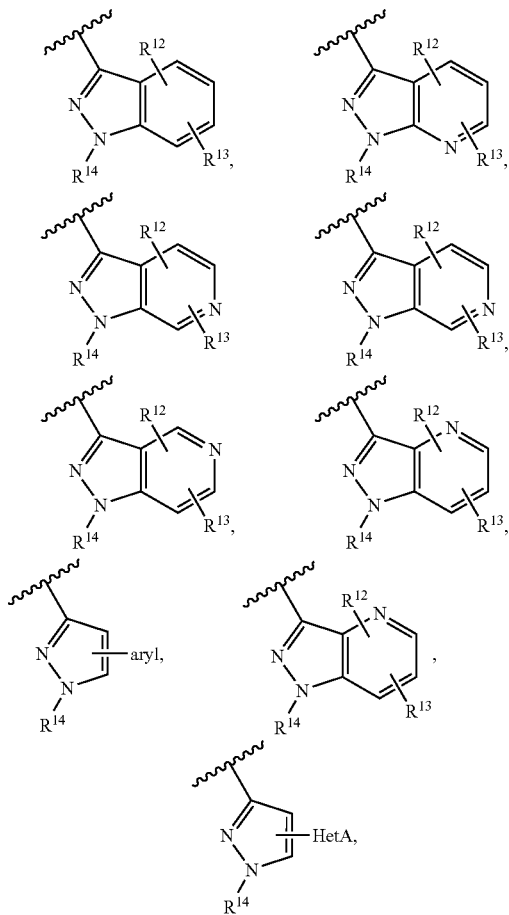

$R^{12}$ and $R^{13}$ are independently selected from the group consisting of hydrogen, halogen, oxo, $NO_2$, CN, $OR^3$, $O(CH_2)_tCF_3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl, $C_{1-3}$ fluoroalkyl, $C_{3-6}$ cycloalkyl, and $NR^3R^4$;
$R^3$ and $R^4$ are independently selected from the group consisting of hydrogen, $C_{1-6}$ alkyl, $C_{1-3}$ fluoroalkyl, and $C_{3-6}$ cycloalkyl;
or, alternatively and optionally, when $R^3$ and $R^4$ are in an $NR^3R^4$ group, then:
(A) one of $R^3$ and $R^4$ is selected from the group consisting of hydrogen, $C_{1-6}$ alkyl, $C_{1-3}$ fluoroalkyl, and $C_{3-6}$ cycloalkyl, and the other of $R^3$ and $R^4$ is $C_{1-6}$ alkyl substituted with $O—C_{1-6}$ alkyl, $C(O)R^A$, $CO_2R^A$, $C(O)N(R^A)R^B$, $SR^A$, $S(O)R^A$, $SO_2R^A$, or $SO_2N(R^A)R^B$; or
(B) $R^3$ and $R^4$ together with the nitrogen atom to which they are both attached form
  (i) a 4- to 7-membered, saturated or unsaturated monocyclic ring optionally containing 1 or 2 heteroatoms in addition to the nitrogen attached to $R^3$ and $R^4$ selected from N, O, and S, where the S is optionally oxidized to $S(O)$ or $S(O)_2$, or
  (ii) a 7- to 12-membered bicyclic ring system wherein each ring in (ii) is independent of, fused to, or bridged with the other ring and each ring is saturated or unsaturated, and wherein the bicyclic ring system optionally contains from 1 to 3 heteroatoms in addition to the nitrogen attached to $R^3$ and $R^4$ selected from N, O, and S, where the S is optionally oxidized to $S(O)$ or $S(O)_2$, and
  wherein the monocyclic ring or the bicyclic ring system is optionally substituted with from 1 to 3 substituents each of which is independently: (1) $C_{1-6}$ alkyl, (2) $C_{1-6}$ haloalkyl, (3) $C_{1-6}$ alkyl substituted with OH, $O—C_{1-6}$ alkyl, $O—C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, or $SO_2N(R^A)R^B$, (4) $O—C_{1-6}$ alkyl, (5) $O—C_{1-6}$ haloalkyl, (6) OH, (7) oxo, (8) halogen, (9) CN, (10) $NO_2$, (11) $N(R^A)R^B$, (12) $C(O)N(R^A)R^B$, (13) $C(O)R^A$, (14) $C(O)—C_{1-6}$ haloalkyl, (15) $C(O)OR^A$, (16) $OC(O)N(R^A)R^B$, (17) $SR^A$, (18) $S(O)R^A$, (19) $S(O)_2R^A$, (20) $S(O)_2N(R^A)R^B$, (21) $N(R^A)COR^B$, or (22) $N(R^A)SO_2R^B$ and
  wherein each $R^A$ is independently H or $C_{1-6}$ alkyl, and each $R^B$ is independently H or $C_{1-6}$ alkyl;
HetA is heteroaryl selected from the group consisting of pyridinyl, pyrimidinyl, and pyrazinyl;
$R^{14}$ is $PO(OH)O^-.M^+$; $PO(O^-)_2.2M^+$; $PO(O^-)_2.M^{+2}$; or an acid salt of:

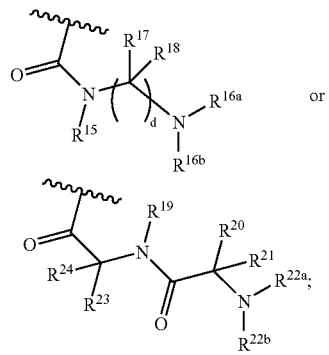

M⁺ is a pharmaceutically acceptable monovalent counterion;
M⁺² is a pharmaceutically acceptable divalent counterion;
$R^{15}$ is H, $C_{1-6}$ alkyl, $(CH_2)_{2-3}CF_3$, AryA, or HetB;
$R^{16a}$ and $R^{16b}$ are each independently H, $C_{1-6}$ alkyl, $(CH_2)_{2-3}CF_3$, AryA, or HetB;
each $R^{17}$ is independently H or $C_{1-6}$ alkyl;
each $R^{18}$ is independently H or $C_{1-6}$ alkyl;
alternatively, $R^{15}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{15}$ is attached, wherein the optional heteroatom is selected from N, O and S, where the S is optionally oxidized to S(O) or $S(O)_2$;
alternatively, $R^{16a}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{16a}$ is attached, wherein the optional heteroatom is selected from N, O and S, where the S is optionally oxidized to S(O) or $S(O)_2$;
alternatively, an $R^{17}$ together with the $R^{18}$ attached to the same carbon atom form a 5- or 6-membered, saturated monocyclic ring optionally containing a heteroatom, wherein the optional heteroatom is selected from N, O and S, where the S is optionally oxidized to S(O) or $S(O)_2$;
$R^{19}$ is H or $C_{1-6}$ alkyl;
$R^{20}$ is H or $C_{1-6}$ alkyl;
$R^{21}$ is H or $C_{1-6}$ alkyl;
$R^{22a}$ and $R^{22b}$ are each independently H, $C_{1-6}$ alkyl, $(CH_2)_{2-3}CF_3$, AryA, or HetB;
$R^{23}$ is H or $C_{1-6}$ alkyl;
$R^{24}$ is H or $C_{1-6}$ alkyl;
alternatively, $R^{19}$ together with $R^{23}$ or $R^{24}$ and the atoms to which each is attached form a 5- to 7-membered, saturated or unsaturated monocyclic ring optionally containing a heteroatom in addition to the N atom to which $R^{19}$ is attached, wherein the optional heteroatom is selected from N, O and S, where the S is optionally oxidized to S(O) or $S(O)_2$;
alternatively, $R^{20}$ and $R^{21}$ together with the carbon atom to which both are attached form a 5- or 6-membered, saturated monocyclic ring optionally containing a heteroatom, wherein the optional heteroatom is selected from N, O and S, where the S is optionally oxidized to S(O) or $S(O)_2$;
alternatively, $R^{22a}$ together with an $R^{20}$ or $R^{21}$ and the atoms to which each is attached form a 5- to 7-membered, saturated or unsaturated monocyclic ring optionally containing a heteroatom in addition to the N atom to which $R^{22a}$ is attached, wherein the optional heteroatom is selected from N, O and S, where the S is optionally oxidized to S(O) or $S(O)_2$;
alternatively, $R^{23}$ and $R^{24}$ together with the carbon atom to which both are attached form a 5- or 6-membered, saturated monocyclic ring optionally containing a heteroatom, wherein the optional heteroatom is selected from N, O and S, where the S is optionally oxidized to S(O) or $S(O)_2$;
wherein the monocyclic ring formed by combining $R^{15}$ together with an $R^{17}$ or $R^{18}$, the monocyclic ring formed by combining $R^{16a}$ together with an $R^{17}$ or $R^{18}$, the monocyclic ring formed by combining $R^{17}$ together with an $R^{18}$, the monocyclic ring formed by combining $R^{19}$ together with an $R^{23}$ or $R^{24}$, the monocyclic ring formed by combining $R^{20}$ together with an $R^{21}$, the monocyclic ring formed by combining $R^{22a}$ together with an $R^{20}$ or $R^{21}$, and the monocyclic ring formed by combining $R^{23}$ together with an $R^{24}$, are each independently and optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, or $SO_2N(R^A)R^B$, (4) O—$C_{1-6}$ alkyl, (5) O—$C_{1-6}$ haloalkyl, (6) OH, (7) oxo, (8) halogen, (9) CN, (10) $NO_2$, (11) $N(R^A)R^B$, (12) $C(O)N(R^A)R^B$, (13) $C(O)R^A$, (14) C(O)—$C_{1-6}$ haloalkyl, (15) $C(O)OR^A$, (16) $OC(O)N(R^A)R^B$, (17) $SR^A$, (18) $S(O)R^A$, (19) $S(O)_2R^A$, (20) $S(O)_2N(R^A)R^B$, (21) $N(R^A)COR^B$, or (22) $N(R^A)SO_2R^B$;

AryA is aryl;
HetB is heteroaryl;
d is 2-4;
s is 1-5;
t is 2-3;
v is 1-2; and
m, in each instance in which it appears, is independently selected from 0-2.

In the definition of the monocyclic ring formed by combining $R^{15}$ together with an $R^{17}$ or $R^{18}$, the phrase "any carbons in a chain therebetween" refers to the carbon chain $[C(R^{17})R^{18})]_{2-4}$. If the ring is formed by combining $R^{15}$ with the $R^{17}$ or $R^{18}$ on the adjacent carbon, there are no carbons therebetween as exemplified by structure A below, wherein the arrow symbolizes the joining of $R^{15}$ and $R^{17}$ to form a ring. If the ring is formed by combining $R^{15}$ with the $R^{17}$ or $R^{18}$ on a non-adjacent carbon, there is at least one carbon therebetween as exemplified by structure B below. Analogous considerations apply with respect to the monocyclic ring formed by combining $R^{16a}$ together with an $R^{17}$ or $R^{18}$.

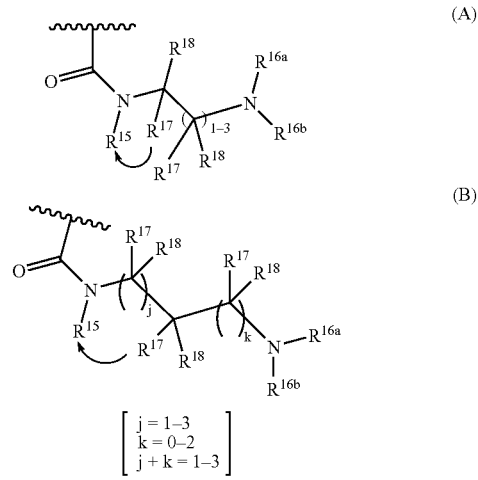

Another embodiment of the present invention (Embodiment PD3) is a compound of Formula I-P, wherein:
$R^{14}$ is $PO(OH)O^-.M^+$; $PO(O^-)_2.2M^+$; $PO(O^-)_2.M^{+2}$; or an acid salt of:

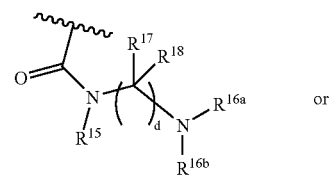

-continued

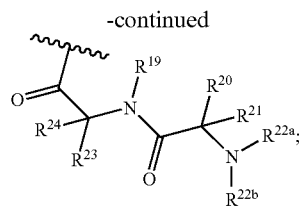

M⁺ is a pharmaceutically acceptable monovalent counterion;
M⁺² is a pharmaceutically acceptable divalent counterion;
$R^{15}$ is H, $C_{1-6}$ alkyl, $(CH_2)_{2-3}CF_3$, AryA, or HetB;
$R^{16a}$ and $R^{16b}$ are each independently H, $C_{1-6}$ alkyl, $(CH_2)_{2-3}CF_3$, AryA, or HetB;
each $R^{17}$ is independently H or $C_{1-6}$ alkyl;
each $R^{18}$ is independently H or $C_{1-6}$ alkyl;
alternatively, an $R^{17}$ together with the $R^{18}$ attached to the same carbon atom form a 5- or 6-membered, saturated monocyclic ring optionally containing a heteroatom, wherein the optional heteroatom is selected from N, O and S, where the S is optionally oxidized to S(O) or S(O)₂;
$R^{19}$ is H or $C_{1-6}$ alkyl;
$R^{20}$ is H or $C_{1-6}$ alkyl;
$R^{21}$ is H or $C_{1-6}$ alkyl;
$R^{22a}$ and $R^{22b}$ are each independently H, $C_{1-6}$ alkyl, $(CH_2)_{2-3}CF_3$, AryA, or HetB;
$R^{23}$ is H or $C_{1-6}$ alkyl;
$R^{24}$ is H or $C_{1-6}$ alkyl;
AryA is phenyl, wherein the phenyl is optionally substituted with from 1 to 3 substituents each of which is independently Cl, Br, F, $CH_3$, $CF_3$, $NH_2$, —NH($CH_3$), —N($CH_3$)₂, —CN, —OH, —$OCH_3$, cyclohexyl, ethenyl, ethynyl, —$SCH_3$, —S(O)₂$CH_3$, —$(CH_2)_{1-2}$—$SCH_3$, —$(CH_2)_{1-2}$—S(O)₂$CH_3$, —NHC(O)$CH_3$, —O$(CH_2)_{1-2}CF_3$, —C(O)$CH_3$, —OC(O)$CH_3$, —$(CH_2)_{1-2}OCH_3$, —C(O)$NH_2$, —C(O)$NHCH_3$, —C(O)N($CH_3$)₂, —C(O)₂H, —C(O)₂$CH_3$, —$(CH_2)_{1-2}C(O)_2CH_3$, —NHC(O)$OCH_3$, —NH($CH_3$)NHC(O)NH($CH_3$), phenyl, or benzyl;
HetB is a 5- or 6-membered heteroaromatic ring containing from 1 to 3 heteroatoms selected from N, O and S, wherein the heteroaromatic ring is optionally substituted with from 1 to 3 substituents each of which is independently Cl, Br, F, $CH_3$, $CF_3$, $NH_2$, —NH($CH_3$), —N($CH_3$)₂, —CN, —OH, —$OCH_3$, cyclohexyl, ethenyl, ethynyl, —$SCH_3$, —S(O)₂$CH_3$, —$(CH_2)_{1-2}$—$SCH_3$, —$(CH_2)_{1-2}$—S(O)₂$CH_3$, —NHC(O)$CH_3$, —O$(CH_2)_{1-2}CF_3$, —C(O)$CH_3$, —OC(O)$CH_3$, —$(CH_2)_{1-2}OCH_3$, —C(O)$NH_2$, —C(O)$NHCH_3$, —C(O)N($CH_3$)₂, —C(O)₂H, —C(O)₂$CH_3$, —$(CH_2)_{1-2}C(O)_2CH_3$, —NHC(O)$OCH_3$, —NH($CH_3$)NHC(O)NH($CH_3$), phenyl, or benzyl; and all other variables are as defined in Embodiment PD2.

Another embodiment of the present invention (Embodiment PD4) is a compound of Formula I-P, wherein:
$R^{14}$ is PO(OH)O⁻.M⁺; PO(O⁻)₂.2M⁺; PO(O⁻)₂.M⁺²; or an acid salt of:

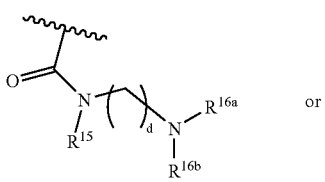

M⁺ is a pharmaceutically acceptable monovalent counterion;
M⁺² is a pharmaceutically acceptable divalent counterion;
$R^{15}$ is H or $C_{1-4}$ alkyl;
$R^{16a}$ and $R^{16b}$ are each independently H or $C_{1-4}$ alkyl;
$R^{19}$ is H or $C_{1-4}$ alkyl;
$R^{20}$ is H or $C_{1-4}$ alkyl;
$R^{22a}$ and $R^{22b}$ are each independently H or $C_{1-4}$ alkyl;

and all other variables are as defined in Embodiment PD2.
Another embodiment of the present invention (Embodiment PD5) is a compound of Formula I-P:
V is —$CH_2$—;
X is —O—;
Y is —O—;
$R^1$ and $R^2$ are each independently selected from the group consisting of hydrogen, halogen, and $C_{1-4}$ alkyl;
A is phenyl optionally substituted with from 1 to 3 substituents each of which is independently halogen, $C_{1-4}$ alkyl, or CN;
$R^{10*}$ is:

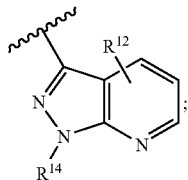

$R^{12}$ is selected from the group consisting of hydrogen, halogen, oxo, $NO_2$, CN, $OR^3$, $O(CH_2)_tCF_3$, $CO_2R^3$, $CONR^3R^4$, $O(CH_2)_tNR^3R^4$, $O(CH_2)_vCOR^3$, $S(O)_mR^3$, $SO_2NR^3R^4$, $C_{1-6}$ alkyl, $C_{1-3}$ fluoroalkyl, and $NR^3R^4$.
$R^{14}$ is PO(OH)O⁻.M⁺; PO(O⁻)₂.2M⁺; PO(O⁻)₂.M⁺²; or an acid salt of:

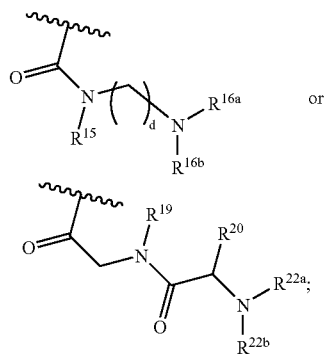

M⁺ is a pharmaceutically acceptable monovalent counterion;
M⁺² is a pharmaceutically acceptable divalent counterion;
$R^{15}$ is H or $C_{1-4}$ alkyl;
$R^{16a}$ and $R^{16b}$ are each independently H or $C_{1-4}$ alkyl;

$R^{19}$ is H or $C_{1-4}$ alkyl;
$R^{20}$ is H or $C_{1-4}$ alkyl;
$R^{22a}$ and $R^{22b}$ are each independently H or $C_{1-4}$ alkyl;
and all other variables are as defined in Embodiment PD2.

Another embodiment of the present invention (Embodiment PD6) is a compound of Formula I-P, wherein:
$R^{14}$ is an acid salt of:

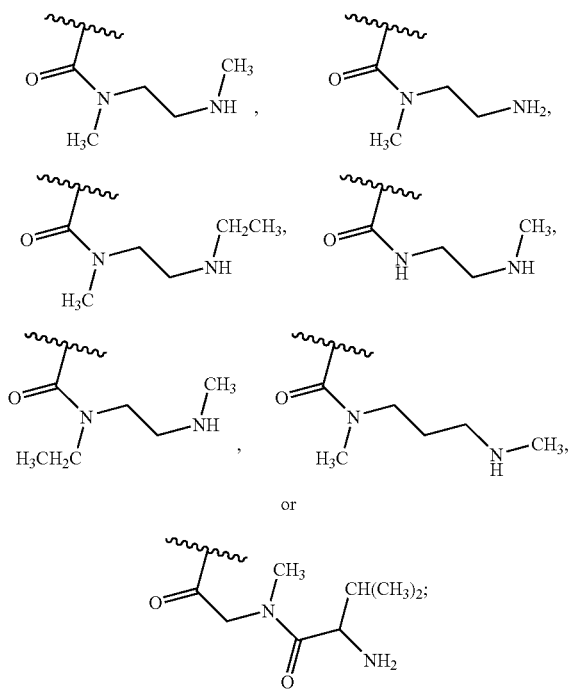

and all other variables are as defined in Embodiment PD5.

A class of the preceding embodiment (Class C11) includes compounds of Formula I-P, wherein the acid salt in the definition of $R^{14}$ is a hydrochloride salt; and all other variables are as defined in Embodiment PD6.

Pharmaceutically acceptable monovalent counterions ($M^+$) suitable for use in the prodrugs of the invention described in Embodiments PD2 to PD5 include $NH_4^+$, alkali metal cations (e.g., $Na^+$ or $K^+$), and cations from alkylamines, hydroxyalkylamines (e.g., tris(hydroxymethyl)methylamine), choline, lysine, arginine, histidine, and N-methyl-D-glucamine. Suitable divalent counterions ($M^{+2}$) include the cations of alkaline earth metals such as $Mg^{+2}$ and $Ca^{+2}$. Additional pharmaceutically acceptable salts of basic drugs (pharmaceutically acceptable monovalent and divalent counterions) are described in P. L. Gould, *Int. J. Pharm.* 1986, vol. 33 pp. 201-217 and S. M. Berge et al., *J. Pharm. Sci.*, 1977, vol. 66, pp. 1-19.

Acid salts suitable for use in the prodrugs of the invention described in Embodiments PD2 to PD6 include the salts of organic and inorganic acids. Suitable salts of inorganic acids include the salts of hydrochloric acid, sulfuric acid, alkali metal bisulfates (e.g., $KHSO_4$), and the like. Suitable salts of organic acids include the salts of carboxylic acids and sulfonic acids, such as alkylcarboxylic acids (e.g., acetic acid, propanoic acid, butyric acid, etc.), fluoroalkylcarboxlic acids (e.g., trifluoroacetic acid), arylcarboxylic acids (benzoic acid), alkylsuflonic acids (e.g., ethylsulfonic acid), fluoroalkylsulfonic acids (e.g., trifluoromethylsulfonic acid), and arylsulfonic acids (e.g., benzenesulfonic acid or toluenesulfonic acid).

While not wishing to be bound by any particular theory, it is believed that the compounds set forth in Embodiments PD2 to PD6 act as prodrugs, wherein the compound is relatively stable at low pH (e.g., pH=1 to 3) but will convert by hydrolysis or cyclization to its free base at physiological pH (e.g., a pH of greater than about 7), thereby releasing the active substance in vivo. This reaction is exemplified as follows for a hydrochloride salt:

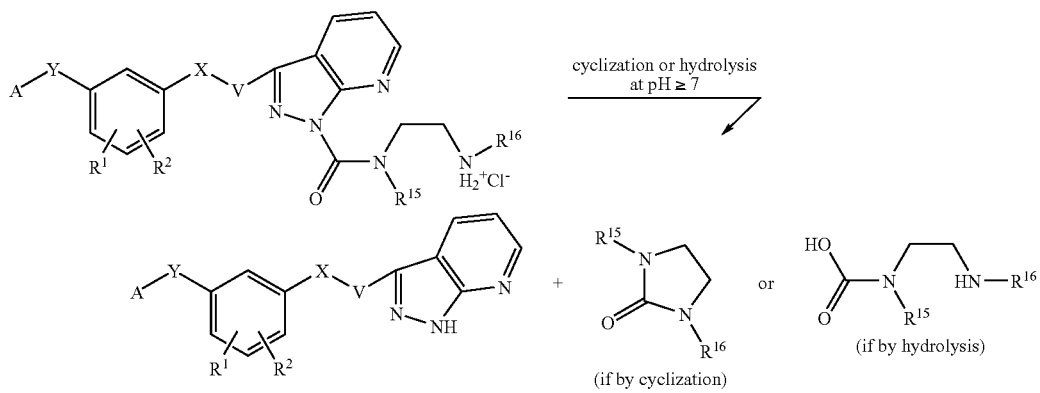

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkylene" refers to both branched- and straight-chain saturated aliphatic hydrocarbon groups, including all isomers, having the specified number of carbons, and having two terminal end chain attachments (i.e., the alkylene is divalent). For illustration, the term "unsubstituted A-$C_4$ alkylene-B" includes A-$CH_2$—$CH_2$—$CH_2$—$CH_2$—B, A-CH[CH($CH_3$)$_2$]—B, A-C($CH_3$)($CH_2CH_3$)—B, A-CH($CH_2CH_2CH_3$)—B, A-CH($CH_3$)CH($CH_3$)—B, A-C($CH_3$)$_2$$CH_2$)—B, and A-$CH_2$C($CH_3$)$_2$—B. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$", and the term "ethenyl" can be represented by "—$CHCH_2$" or "—$CH=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers, all of the butenyl isomers (e.g., 1-butenyl, 2-butenyl, 3-butenyl, 2,2-dimethylethenyl, and 2-methyl-1-propenyl), 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetylene (or ethyne) is represented, for example, by "CHCH" or alternatively, by "HC≡CH", and the term "ethynyl" can be represented by "—CCH" or "—C≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers, all of the butynyl isomers, 1-propynyl, 2-propynyl, and ethynyl (or acetylenyl). Similar terms such as "$C_{2-3}$ alkynyl" have an analogous meaning.

Unless otherwise specifically noted as only "unsubstituted" or only "substituted", alkyl, alkylene, alkoxy, alkenyl and alkynyl groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), —NHSO$_2$NH$_2$, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. If $C_0$ necessarily results in an open valence, then it is assumed the valence is satisfied by an H. For example, ($C_0$-$C_6$ alkyl)OC(O)— becomes HOC(O)— for $C_0$. Similarly, when an integer defining the presence of a certain number of atoms in a group is equal to zero, it means that the atoms adjacent thereto are connected directly by a bond. For example, in the structure

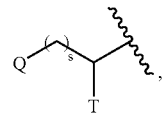

wherein s is an integer equal to zero, 1 or 2, the structure is

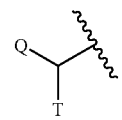

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-3}$ fluoroalkyl" has an analogous meaning where the halogen substituents are restricted to fluoro, and where the number of fluoro atoms can be, for example one to seven, depending on the number of carbon atoms. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, or bridged with, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

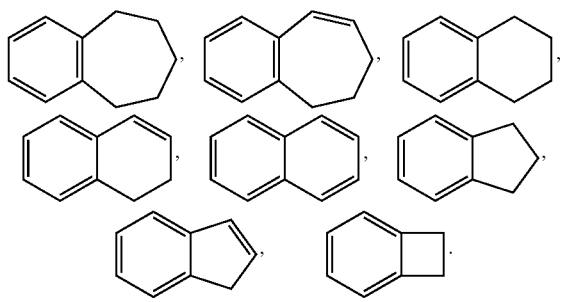

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, or bridged with, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_{3-8}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Thus, a substituted cycloalkyl, substituted aryl, or substituted heterocycle can be a cycloalkyl (e.g., cyclopentyl or cyclohexyl), an aryl (e.g., phenyl or naphthyl), or a heterocycle (e.g., a heteroaryl) as defined herein substituted with from 1 to 3 substituents each of which is independently halo, $C_1$-$C_6$ alkyl, $CF_3$, $NH_2$, —NH($C_1$-$C_6$ alkyl), —N($C_1$-$C_6$ alkyl)$_2$, —NO$_2$, oxo, —CN, —OH, —O—($C_1$-$C_6$ alkyl), $C_3$-$C_6$ cycloalkyl, $C_2$-$C_6$ alkenyl, $C_2$-$C_6$ alkynyl, —S(O)$_{0-2}$($C_1$-$C_6$ alkyl), —($C_1$-$C_6$ alkylene)-S(O)$_{0-2}$($C_1$-$C_6$ alkyl), —NHC(O)($C_1$-$C_6$ alkyl), —C(=NH)NH$_2$, —O($C_1$-$C_6$ alkylene)CF$_3$, —C(O)($C_1$-$C_6$ alkyl), —C(O)H, —OC(O)($C_1$-$C_6$ alkyl), —($C_1$-$C_6$ alkylene)O($C_1$-$C_6$ alkyl), —C(O)NH$_2$, —C(O)NH($C_1$-$C_6$ alkyl), —C(O)N($C_1$-$C_6$ alkyl)$_2$, —C(O)$_2$H, —C(O)$_2$($C_1$-$C_6$ alkyl), —($C_1$-$C_6$ alkylene)C(O)$_{1-2}$($C_1$-$C_6$ alkyl), —NHC(O)O—($C_1$-$C_6$ alkyl), —NH($C_1$-$C_6$ alkyl) NHC(O)NH($C_1$-$C_6$ alkyl), —NHSO$_2$NH$_2$, —NH($C_1$-$C_6$ alkyl)NHSO$_2$($C_1$-$C_6$ alkyl), —NHSO$_2$($C_1$-$C_6$ alkyl), —($C_1$-$C_6$ alkyl)NHSO$_2$($C_1$-$C_6$ alkyl), phenyl, or benzyl.

As another example, a substituted cycloalkyl, substituted aryl, or substituted heterocycle can be a cycloalkyl (e.g., cyclopentyl or cyclohexyl), an aryl (e.g., phenyl or naphthyl), or a heterocycle (e.g., a heteroaryl) as defined herein substituted with from 1 to 3 substituents each of which is independently Cl, Br, F, $CH_3$, $CF_3$, $NH_2$, —NH($CH_3$), —N($CH_3$)$_2$, oxo, —CN, —OH, —OCH$_3$, cyclohexyl, ethenyl, ethynyl, —SCH$_3$, —S(O)$_2$CH$_3$, —(CH$_2$)$_{1-2}$—SCH$_3$, —(CH$_2$)$_{1-2}$—S(O)$_2$CH$_3$, —NHC(O)CH$_3$, —O(CH$_2$)$_{1-2}$CF$_3$, —C(O)CH$_3$, —OC(O)CH$_3$, —(CH$_2$)$_{1-2}$OCH$_3$, —C(O)NH$_2$, —C(O)NHCH$_3$, —C(O)N(CH$_3$)$_2$, —C(O)$_2$H, —C(O)$_2$CH$_3$, —(CH$_2$)$_{1-2}$C(O)$_2$CH$_3$, —NHC(O)OCH$_3$, —NH(CH$_3$)NHC(O)NH(CH$_3$), phenyl, or benzyl.

Preferred sets of substituents for substituted cycloalkyl, substituted aryl, or substituted heterocycle are those set forth in the three preceding paragraphs, wherein at most 1 of the up to 3 substituents is or contains aryl (e.g., phenyl), heteroaryl, or heterocyclyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 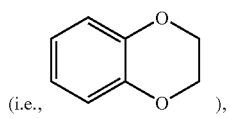), imidazo(2,1-b)(1,3)thiazole, (i.e., 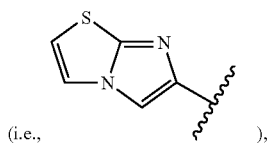), and benzo-1,3-dioxolyl (i.e., 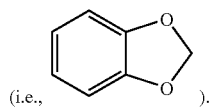).

In certain contexts herein,

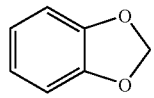

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic C6 carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 3 substituents" is intended to include as aspects thereof, an aryl or heteroaryl optionally substituted with 1 to 3 substituents, 1 to 2 substituents, 2 to 3 substituents, 1 substituent, 2 substituents, and 3 substituents.

When any variable occurs more than one time in any constituent or in any formula depicting and describing compounds of the invention, its definition on each occurrence is independent of its definition at every other occurrence. Thus, for example, when V, X and Y are all —C(R$^5$R$^6$)— (see Formula I, e.g.), they may be the same or different. More particularly, in one embodiment —C(R$^5$R$^6$)— can be selected from —CH$_2$—, —CH(CH$_3$)—, and —C(CH$_3$)$_2$—, in which case there are several possible combinations of V, X and Y, including but not limited to V=X=Y=—CH$_2$—; V=—CH$_2$—, X=—CH(CH$_3$)—, Y=—CH$_2$—; V=—CH$_2$—, X=—CH$_2$—, Y=—CH(CH$_3$)—; V=—CH(CH$_3$)—, X=—CH$_2$—, Y=—CH$_2$—; V=—CH$_2$—, X=—CH$_2$—, Y=—C(CH$_3$)$_2$—; V=—CH(CH$_3$)—, X=—CH$_2$—, Y=—C(CH$_3$)$_2$—; and so forth.

Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed. The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g., a solvent or water) trapped within.

The symbol " " or " " at the end of a bond refers to the point of attachment of a functional group or other chemical moiety to the rest of the molecule of which it is a part.

In compounds of the invention having pyridyl N-oxide moieties, the pyridyl-N-oxide portion is structurally depicted using conventional representations such as

which have equivalent meanings.

For variable definitions containing terms having repeated terms, e.g., (CR$^i$R$^j$)$_r$, where r is the integer 2, R$^i$ is a defined variable, and R$^j$ is a defined variable, the value of R$^i$ may differ in each instance in which it occurs, and the value of R$^j$ may differ in each instance in which it occurs. For example, if R$^i$ and R$^j$ are independently selected from the group consisting of methyl, ethyl, propyl and butyl, then (CR$^i$R$^j$)$_2$ can be

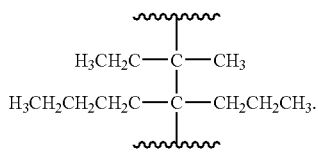

Pharmaceutically acceptable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I and of Formula I'.

The method of the present invention involves the use of compounds of Formula I or Formula I' in the inhibition of HIV reverse transcriptase, the prophylaxis or treatment of infection by human immunodeficiency virus (HIV) and the prophylaxis, treatment or the delay in the onset of consequent pathological conditions such as AIDS. Prophylaxis of AIDS, treating AIDS, delaying the onset of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery. As another example, the present invention can also be employed to prevent transmission of HIV from a pregnant female infected with HIV to her unborn child or from an HIV-infected female who is nursing (i.e., breast feeding) a child to the child via administration of an effective amount of a compound of Formula I or of Formula I', or a pharmaceutically acceptable salt thereof.

The compounds of Formula I and Formula I' can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain of the compounds employed in the present invention carry an acidic moiety (e.g., —COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of Formula I or Formula I' mean providing the compound or a prodrug of the compound to the individual in need of treatment or prophylaxis. When a compound of the invention or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV reverse transcriptase and thereby elicit the response being sought (i.e., an "inhibition effective amount"). When the active compound (i.e., active ingredient) is administered as the salt, references to the amount of active ingredient are to the free form (i.e., the non-salt form) of the compound.

In the method of the present invention (i.e., inhibiting HIV reverse transcriptase, treating or prophylaxis of HIV infection or treating, prophylaxis of, or delaying the onset of AIDS), the compounds of Formula I and Formula I', optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid-filled capsules can also be employed for oral administration of the compounds of the invention; e.g., a liquid-filled capsule (hard gelatin) containing up to about 8 mg of the compound of Example 36 in Cremophor EL:Labrasol:Tween 80 1:1:1, wherein Cremophor EL (BASF, Parsipanny, N.J.) is a derivative of castor oil and ethylene oxide; Labrasol (Gattefosse Corporation, Westwood, N.J.) consists of caprylocaproyl macrogol-8 glycerides; and Tween 80 is polyoxyethylene sorbitan monooleate. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18th edition, edited by A. R. Gennaro, Mack Publishing Co., 1990 and in *Remington—The Science and Practice of Pharmacy*, 21st edition, Lippincott Williams & Wilkins, 2005.

The compounds of Formula I and Formula I' can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. As an example, it is believed that the compound of Example 36 can be administered orally in a range of from about 0.5 to about 12 mg/kg twice per day. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to the use of the compounds of Formula I and of Formula I' in combination with one or more agents useful in the treatment of HIV infection or AIDS. For example, the compounds of Formula I and of Formula I' can be effectively administered, whether at periods of pre-exposure and/or post-exposure, in combination with effective amounts of one or more HIV antiviral agents, imunomodulators, antiinfectives, or vaccines useful for treating HIV infection or AIDS, such as those disclosed in Table 1 of WO 01/38332 or in the Table in WO 02/30930. Suitable HIV antiviral agents for use in combination with the compounds of Formula I and of Formula I' include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), non-nucleoside HIV reverse transcriptase inhibitors (e.g., efavirenz or nevirapine), and HIV integrase inhibitors such as those described in WO 02/30930, WO 03/35076, and WO 03/35077. It will be understood that the scope of combinations of compounds of Formula I and Formula I' with HIV antiviral agents, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV antiviral agents and other agents will typically be employed in these combinations in their conventional dosage ranges and regimens as reported in the art, including, for example, the dosages described in the *Physicians' Desk Reference*, 57th edition, Thomson PDR, 2003. The dosage ranges for a compound of Formula I and Formula I' in these combinations are the same as those set forth above. All agents can optionally be used in the form of pharmaceutically acceptable salts.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

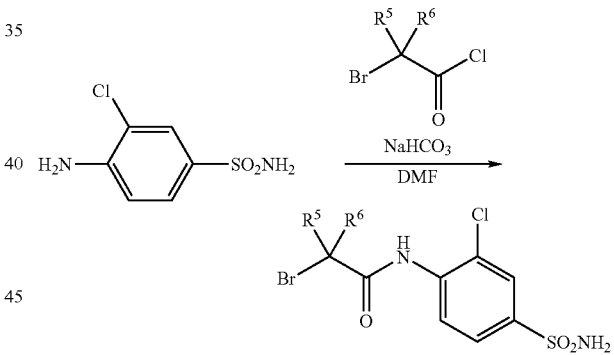

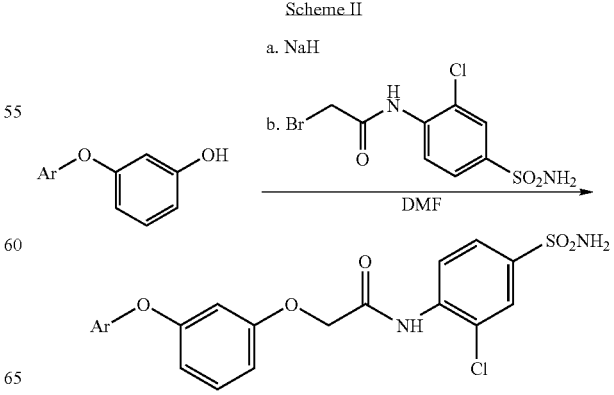

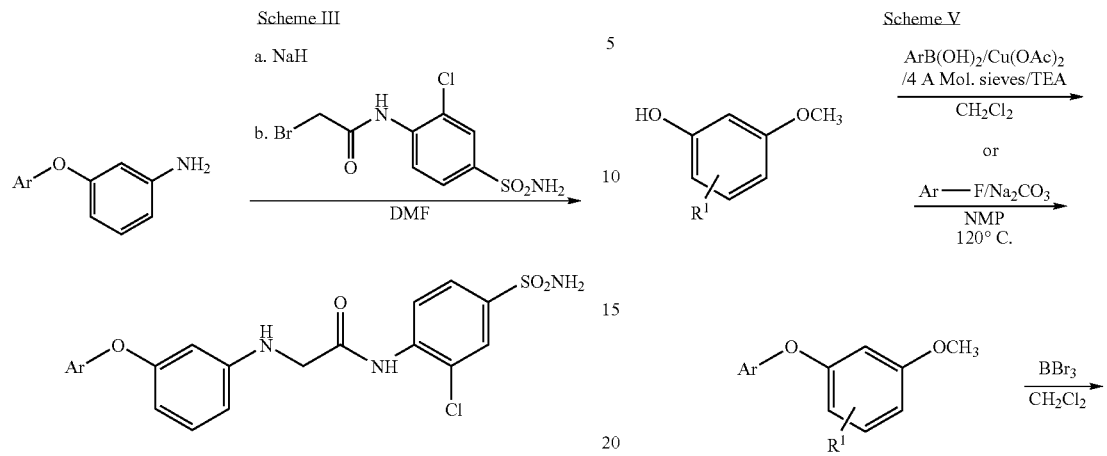
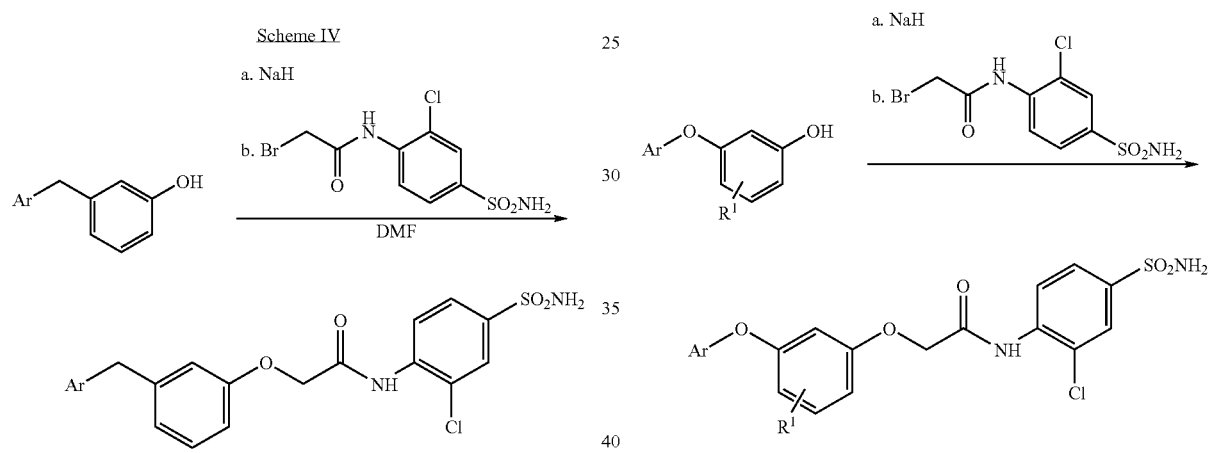
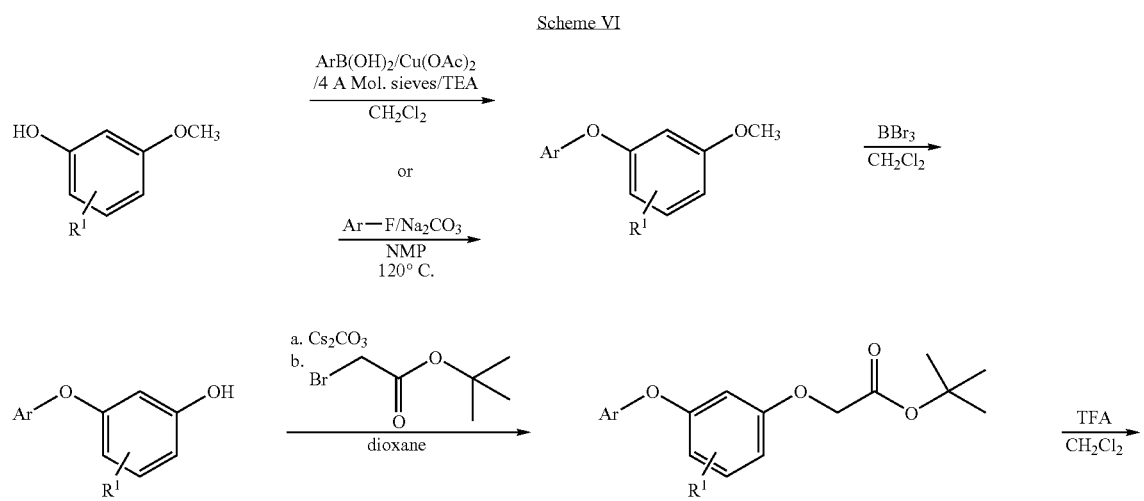

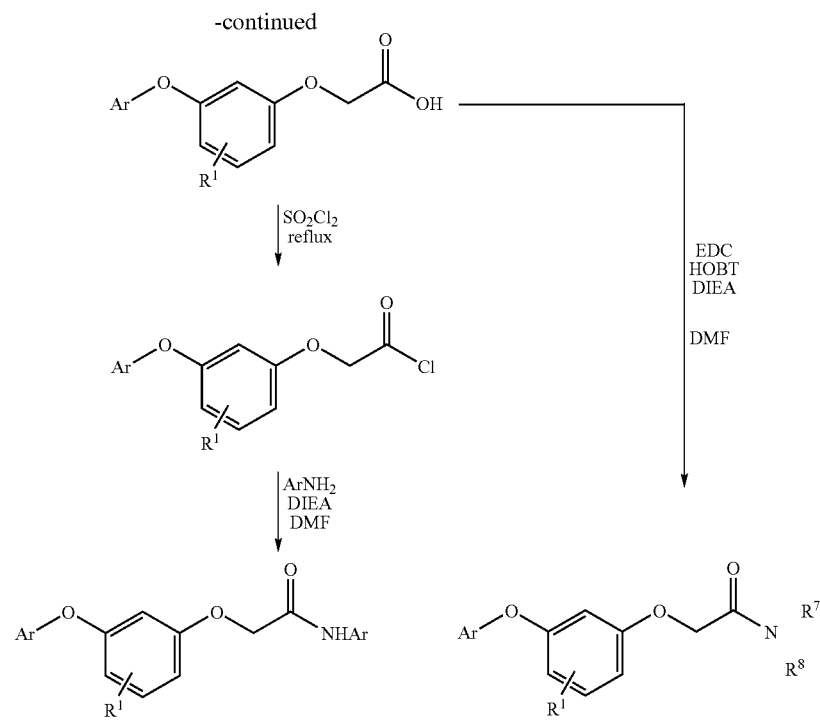

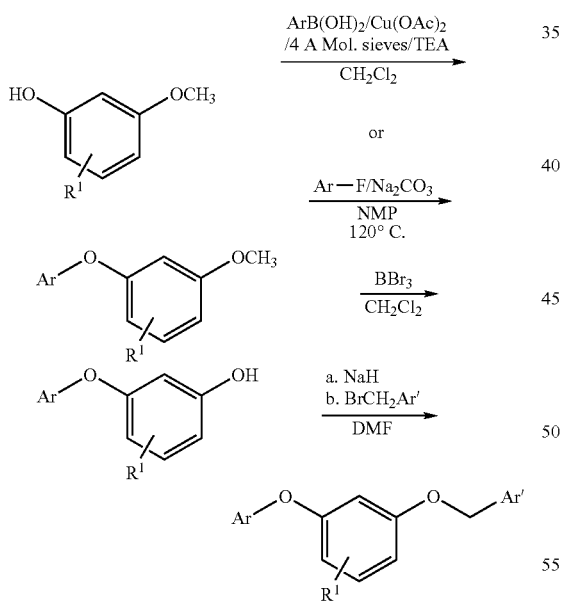

Scheme VII

In these schemes, Ar is an aryl or heteroaryl group as defined above.

Scheme VIII depicts a method for preparing compounds of Formula I (and Formula I') in which Y═O and X═V═CH₂—. In the method, the phenol VIII-1 is treated with triflic anhydride to afford phenyl triflate VIII-2. The triflate can then be coupled with TMS-acetylene using modified Sonogashira conditions (see *Tetrahedron Lett.* 1975, 16: 4467-4470) to provide protected acetylene VIII-3. Deprotection of VIII-3 (e.g., by treatment with TBAF) provides the phenylacetylene VIII-4, which can then be coupled with a suitable heterocyclyl halide (see *Tetrahedron Lett* 2002, 43: 2695-2697) to provide VIII-5 which can be hydrogenated (e.g., H₂, Pd/C) and deprotected as necessary (e.g., deprotection of chemically sensitive group(s) in Z) to afford the desired phenylethylheterocycle VIII-6.

Scheme VIII

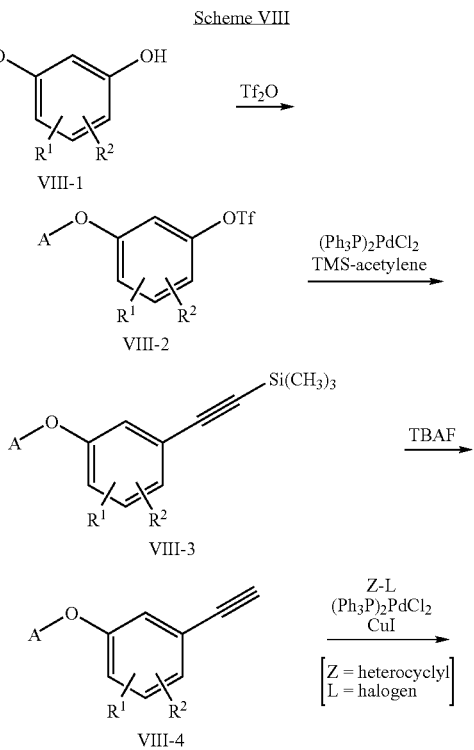

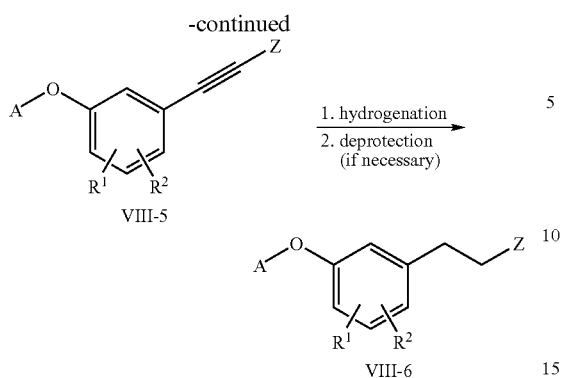

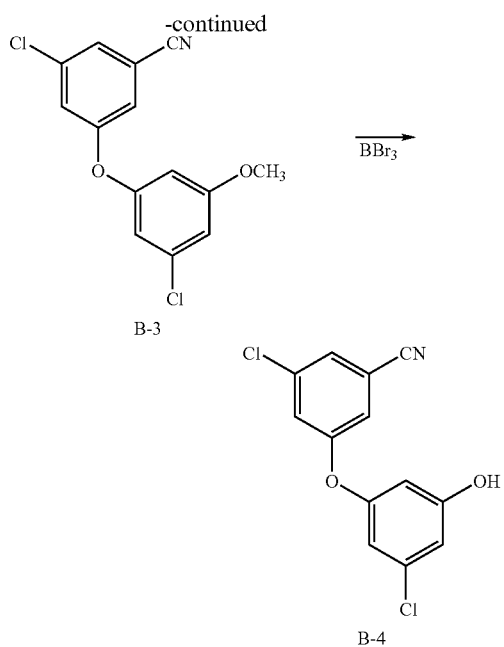

3-chloro-5-(3-chloro-5-methoxyphenoxy)benzonitrile(B-3)

A mixture of 1.00 g (6.31 mmol) of 3-chloro-5-methoxyphenol (B-1), of 1.28 g (8.20 mmol) 3-fluoro-5-chlorobenzonitrile (B-2), and 2.62 g (18.93 mmol) of potassium carbonate in 10 mL of N-methylpyrrolidinone was heated at 120° C. in a nitrogen atmosphere with vigorous stirring. After 6 hours, LC/MS analysis indicated that the reaction was complete. The reaction was cooled to room temperature and filtered, and the solid washed with EtOAc. The filtrate was diluted further with EtOAc, and was washed with 20 mL of 1N HCl, 20 mL of 1 N NaOH, 20 mL of water, and 20 mL of brine. The organic layer was dried (anhydrous MgSO$_4$), filtered, and the filtrate concentrated in vacuo to an orange oil. The oil was purified by flash column chromatography over silica gel with 3:1 cloroform/hexanes to give the desired product B-3 as a clear oil. MS: M+1=295. $^1$H NMR(CDCl$_3$): 3.81 δ(s, 3H), 6.44 m, 1H), 6.62 (m, 1H), 6.78 (m, 1H), 7.14 (m, 1H), 7.22 (m, 1H), 7.37 (m, 1H).

3-chloro-5-(3-chloro-5-hydroxyphenoxy)benzonitrile (B-4)

A stirred solution of 500 mg (1.70 mmol) of 3-chloro-5-(3-chloro-5-methoxyphenoxy)benzonitrile(B-3) in 5 mL CH$_2$Cl$_2$ was cooled to −20° C. in a nitrogen atmosphere. The reaction was treated with 5.10 mL (5.10 mmol) of a 1M solution of boron tribromide in CH$_2$Cl$_2$, and the resulting solution was stirred in the cold for 30 minutes, then at ambient temp. for 18 hours. The reaction was carefully poured into excess ice water with stirring, and the mixture extracted twice with diethyl ether. The combined ether extracts were washed with brine, dried (anhydrous MgSO$_4$), filtered and concentrated in vacuo to give the desired product B-4 as a yellow oil which slowly crystallized to a yellow solid. MS: M+=280.

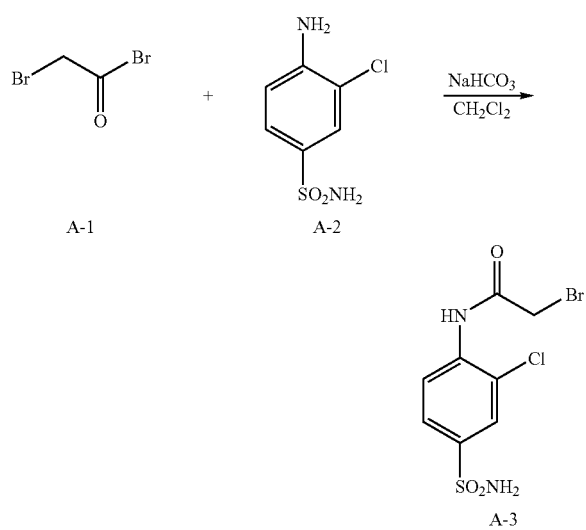

N-[4-(aminosulfonyl)-2-chlorophenyl]-2-bromoacetamide

A mixture of 750 mg (3.63 mmol) of 4-amino-3-chlorobenzenesulfonamide (A-2) and 610 mg (7.26 mmol) of sodium bicarbonate in 25 mL of CH$_2$Cl$_2$ was stirred at room temperature for 18 hours. Bromoacetyl bromide (A-1) was then added, and the mixture was stirred for an additional 12 hours. The mixture was then concentrated in vacuo to a yellow oil. The oil was washed with three 25 mL portions of diethyl ether, decanted, and concentrated in vacuo to give the desired product A-3 as a tan solid. MS: M+1=329.0.

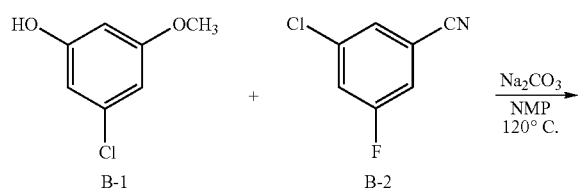

INTERMEDIATE C

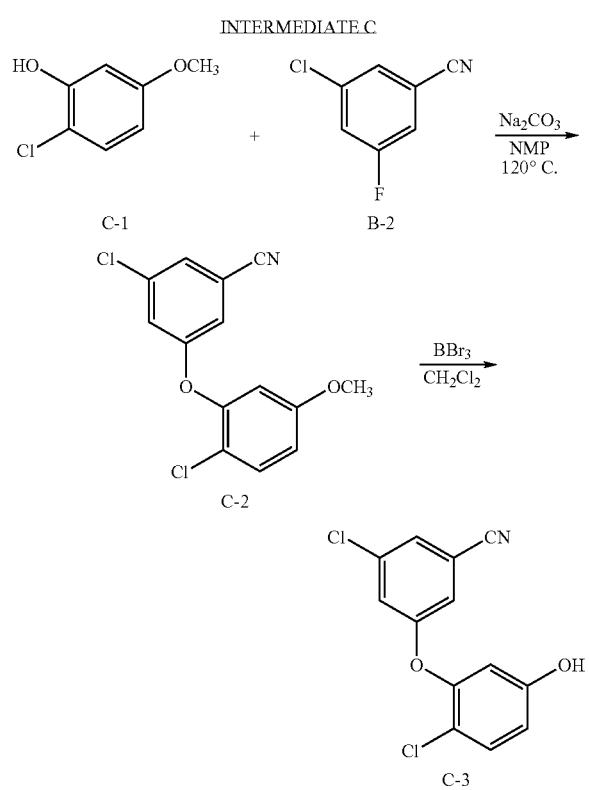

3-chloro-5-(2-chloro-5-methoxyphenoxy)benzonitrile(C-2)

In a manner identical to that described above in Intermediate B for the synthesis of B-3, from 340 mg (2.14 mmol) of 2-chloro-5-methoxyphenol (C-1) and 433 mg (2.78 mmol) of 3-fluoro-5-chlorobenzonitrile (B-2), was obtained the desired product C-2 as a white solid. MS M+=293.

3-chloro-5-(2-chloro-5-hydroxyphenoxy)benzonitrile (C-3)

In a manner identical to that described in Intermediate B above for the synthesis of B-4, from 265 mg (0.90 mmol) of 3-chloro-5-(2-chloro-5-methoxyphenoxy)benzonitrile(8-2) was obtained the desired product C-3 as a pale yellow solid. MS M+=280.

Example 1

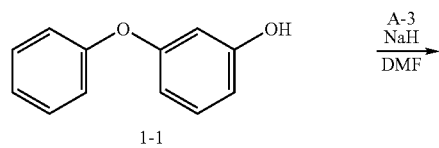

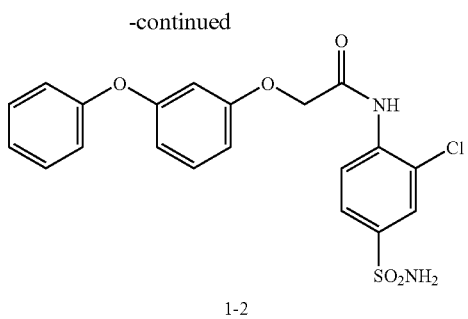

N-[4-(aminosulfonyl)-2-chlorophenyl]-2-(3-phenoxyphenoxy)acetamide (1-2)

A stirred solution of 37 mg (0.198 mmol) of 3-phenoxyphenol (1-1) in 1 mL anhydrous DMF under nitrogen was treated with 10 mg (0.397 mmol) of 60% NaH dispersion. The resulting mixture was stirred at room temperature for 4 hours and then treated with 65 mg (0.198 mmol) of N-[4-(aminosulfonyl)-2-chlorophenyl]-2-bromoacetamide (A-3). This mixture was then stirred at room temperature for an additional 4 hours. The reaction was concentrated in vacuo, and the residue was purified by reverse phase prep LC on a Gilson unit. Clean product fractions were combined and concentrated in vacuo to give the desired product 1-2 as a white solid. MS: M+1=433.2.

Example 2

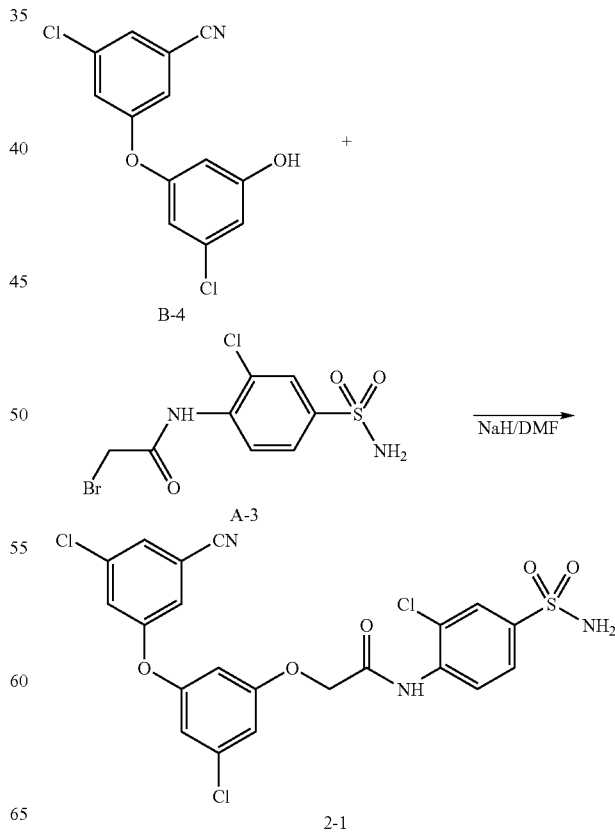

N-[4-(aminosulfonyl)-2-chlorophenyl]-2-[3-chloro-5-(3-chloro-5-cyanophenoxy)phenoxy]acetamide (2-1)

Solid sodium hydride (18 mg, 0.458 mmol) was added in portions to a DMF solution of 128 mg (0.458 mmol) of 3-chloro-5-(3-chloro-5-hydroxyphenoxy)benzonitrile (B-4). This was stirred for 30 minutes at room temperature and then 75 mg (0.229 mmol) of solid N-[4-(aminosulfonyl)-2-chlorophenyl]-2-bromoacetamide (A-3) was added. The reaction was then stirred at 50° C. for 14 hours until an LC/MS analysis indicated that the reaction was complete. The product was purified by a reverse phase hplc column on a Gilson unit. Clean fractions were combined and concentrated in vacuo to give the desired product 2-1 as an amorphous solid. HRMS: measured 525.9788; theoretical 525.9793. $^1$H NMR (DMSO-$d_6$): 4.91 (s, 2H), 6.80 (m, 1H), 6.89 (m, 1H), 7.03 (m, 1H), 7.48 (s, 2H), 7.54 (m, 1H), 7.60 (m, 1H), 7.77 (d, 1H), 7.85 (s, 1H), 7.91 (s, 1H), 8.02 (d, 1H), 9.87 (s, 1H).

Example 3

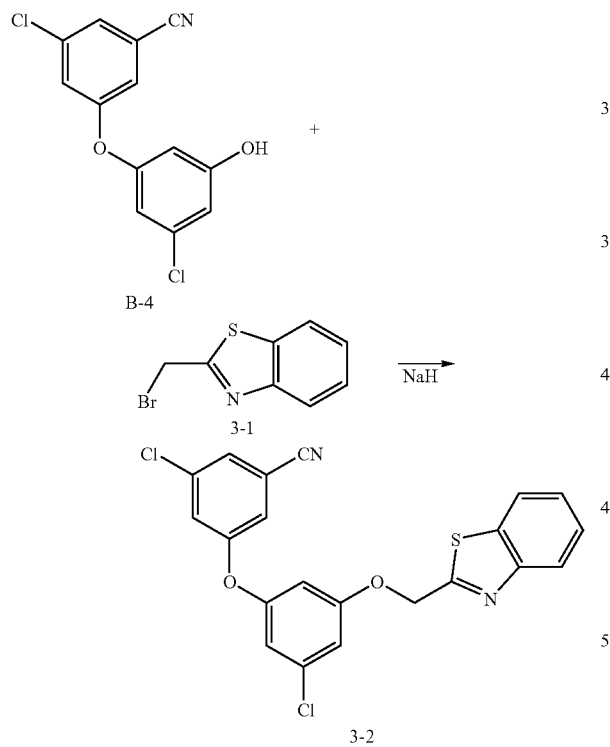

3-[3-(1,3-benzothiazol-2-ylmethoxy)-5-chlorophenoxy]-5-chlorobenzonitrile (3-2)

In a manner similar to that described in Example 1 above for the synthesis of 1-2, from 8 mg (0.196 mmol) of solid sodium hydride, 50 mg (0.179 mmol) of 3-chloro-5-(3-chloro-5-hydroxyphenoxy)benzonitrile (B-4) and 57 mg (0.250 mmol) of 2-(bromomethyl)-1,3-benzothiazole (3-1) was prepared the desired product 3-2. HRMS: measured 427.0081; theoretical 427.0069. $^1$H NMR (CDCl$_3$): 5.46 (s, 2H), 6.62 (m, 1H), 6.68 (m, 1H), 6.93 (m, 1H), 7.13 (m, 1H), 7.20 (m, 1H), 7.37 (m, 1H), 7.43 (t, 1H), 7.52 (t, 1H), 7.91 (d, 1H), 8.03 (d, 1H).

Example 4

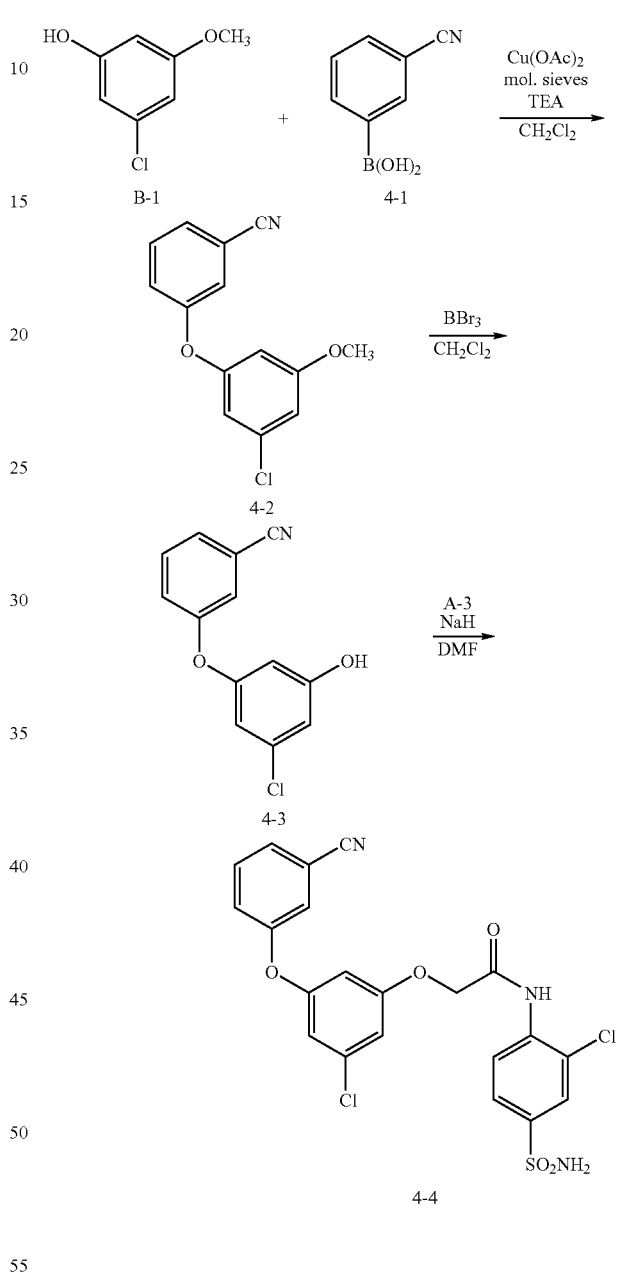

3-(3-chloro-5-methoxyphenoxy)benzonitrile(4-2)

A mixture of 0.54 g (3.40 mmol) of 3-chloro-5-methoxyphenol (B-1), 1.00 g (6.81 mmol) of 3-cyanophenyl boronic acid(4-1), 0.62 g (3.40 mmol) of copper(II) acetate, and 4.00 g of freshly activated powdered 4A molecular sieves was stirred in 17 mL CH$_2$Cl$_2$ in a screw top glass sealed tube. The reaction was treated with 2.37 mL (17.00 mmol) of triethylamine, and the vessel loosely capped. The mixture was stirred vigorously at room temp. for 48 hours. The mixture was filtered through a pad of Celite, and the filtrate concentrated in vacuo to a black residue. The crude residue was purified by flash column chromatography over silica gel with 4:1 chloroform/hexanes to give 610 mg of the desired product 4-2 as a clear oil. MS: M+=260. $^1$H NMR(CDCl$_3$): 3.79 (s, 3H), 6.47 (m, 1H), 6.59 (m, 1H), 6.73 (m, 1H), 7.39-7.45 (complex, 3H), 7.67 (dd, 1H).

3-(3-chloro-5-hydroxyphenoxy)benzonitrile(4-3)

In a manner identical to that described in Example 3 above for the synthesis of B-4, from 610 mg (2.35 mmol) of 3-(3-chloro-5-methoxyphenoxy)benzonitrile (4-2) was prepared the desired compound 4-3. MS M+=246. $^1$H NMR(CDCl$_3$): 5.18 (br s, 1H), 6.42 (m, 1H), 6.58 (m, 1H), 6.67 (m, 1H), 7.40-7.50 (complex, 3H), 7.67 (dd, 1H).

N-[4-(aminosulfonyl)-2-chlorophenyl]-2-[3-chloro-5-(3-cyanophenoxy)phenoxy]acetamide (4-4)

In a manner identical to that described above for the synthesis of 1-2, from 100 mg (0.407 mmol) of 3-(3-chloro-5-hydroxyphenoxy)benzonitrile (4-3), 32 mg (1.221 mmol) NaH 60% dispersion, and 133 mg (0.406 mmol) of N-[4-(aminosulfonyl)-2-chlorophenyl]-2-bromoacetamide (A-3) was prepared the desired product 4-4 as a white solid. HRMS: measured 492.1090 theoretical 492.1082. $^1$H NMR (DMSO-d$_6$): δ 9.83 (s, 1H), 8.01 (d, 1H), 7.90 (s, 1H), 7.76 (d, 1H), 7.61 (dd, 2H), 7.48 (s, 1H), 7.42 (d, 1H), 7.01 (s, 1H), 6.81 (s, 1H), 6.74 (s, 1H), 4.92 (s, 2H).

Example 5

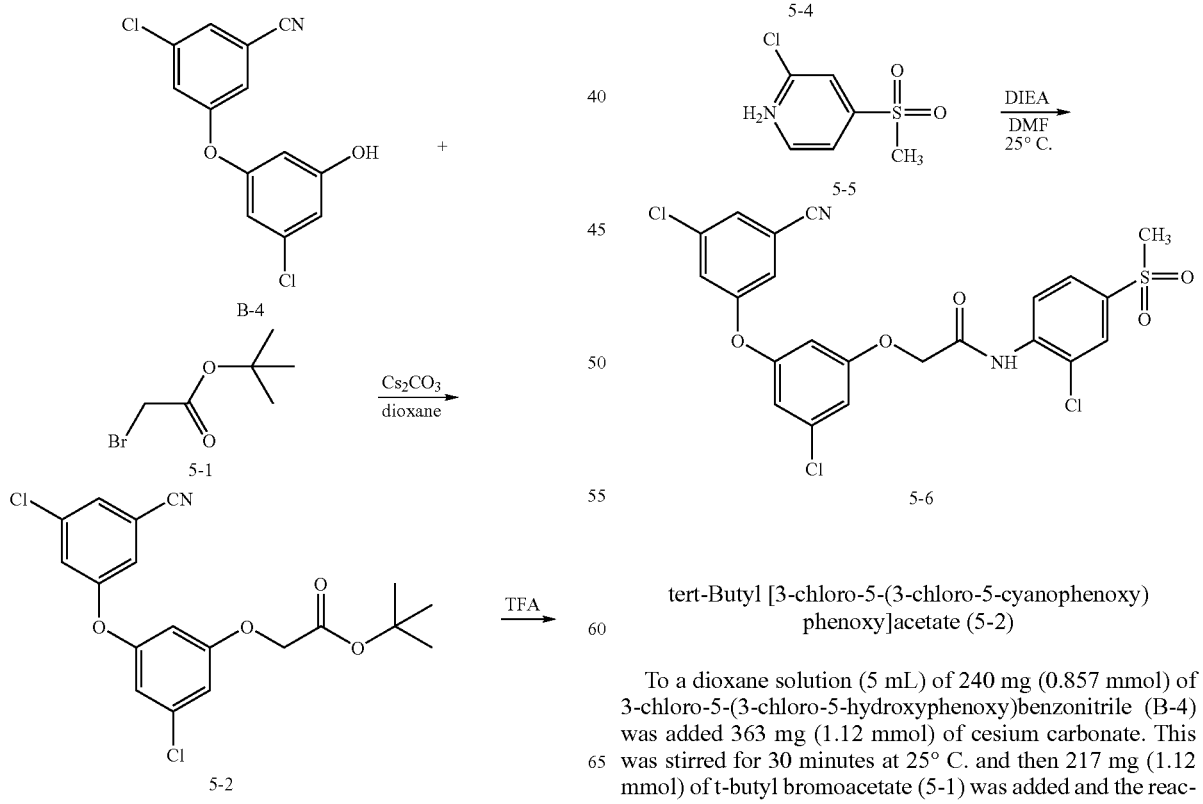

tert-Butyl [3-chloro-5-(3-chloro-5-cyanophenoxy)phenoxy]acetate (5-2)

To a dioxane solution (5 mL) of 240 mg (0.857 mmol) of 3-chloro-5-(3-chloro-5-hydroxyphenoxy)benzonitrile (B-4) was added 363 mg (1.12 mmol) of cesium carbonate. This was stirred for 30 minutes at 25° C. and then 217 mg (1.12 mmol) of t-butyl bromoacetate (5-1) was added and the reaction was stirred until the LC/MS analysis indicated that the reaction was complete. The solids were then removed by filtration and the filtrate was concentrated and purified on a CombiFlash silica column eluted with an ethyl acetate:hexanes gradient to recover desired product 5-2 as an oil. $R_f$=0.9 (EtOAc:hexanes 1:4). MS: M+1=395. $^1$H NMR(CDCl$_3$): 1.49 (s, 9H), 4.49 (s, 2H), 6.48 (t, 1H), 6.66 (t, 1H), 6.74 (t, 1H), 7.14 (m, 1H), 7.21 (m, 1H), 7.38 (m, 1H).

[3-chloro-5-(3-chloro-5-cyanophenoxy)phenoxy] acetic acid (5-3)

221 mg (0.561 mmol) of tert-butyl [3-chloro-5-(3-chloro-5-cyanophenoxy)phenoxy]acetate (5-2) was treated with neat trifluoroacetic acid until an LC/MS analysis indicated that the reaction was complete. The reaction was concentrated in vacuo and no further purification was done on the resultant desired product 5-3 which was isolated as an oil. MS: M+1=338.

[3-chloro-5-(3-chloro-5-cyanophenoxy)phenoxy] acetyl chloride (5-4)

190 mg (0.562 mmol) of [3-chloro-5-(3-chloro-5-cyanophenoxy)phenoxy]acetic acid (5-3) was refluxed in an excess of thionyl chloride for 5 hours. After this time the reaction was cooled and the thionyl chloride was removed in vacuo and the resultant oil solidified upon storage under reduced pressure to yield the desired product 5-4. $^1$H NMR (CDCl$_3$): 4.94 (s, 2H), 6.49 (m, 1H), 6.71 (m, 1H), 6.74 (m, 1H), 7.16 (m, 1H), 7.23 (m, 1H), 7.41 (m, 1H).

2-[3-chloro-5-(3-chloro-5-cyanophenoxy)phenoxy]- N-[2-chloro-4-(methylsulfonyl)phenyl]acetamide (5-6)

A DMF solution (0.5 mL) of 29 mg (0.081 mmol) of [3-chloro-5-(3-chloro-5-cyanophenoxy)phenoxy]acetyl chloride (5-4), 33 mg (0.163 mmol) of 2-chloro-4-methylsulfonylaniline (5-5) and 21 mg (0.163 mmol) of DIEA were stirred at 25° C. until the reaction would not proceed any further. This solution was loaded directly onto a CombiFlash silica gel column eluted with EtOAc:hexanes (3:97 to 100:0). Clean fractions were combined and concentrated in vacuo to give the desired product 5-6 as a white solid. $R_f$=0.8 (DCM:MeOH:NH$_4$OH 98:2:0.2). HRMS (M+Na): measured 542.0066; theoretical 542.0105. $^1$H NMR(CDCl$_3$): 3.07 (s, 3H), 4.69 (s, 2H), 6.61 (m, 1H), 6.74 (m, 1H), 6.89 (m, 1H), 7.15 (m, 1H), 7.25 (m, 1H), 7.42 (m, 1H), 6.94 (dd, 1H), 8.02 (m, 1H), 8.74 (d, 1H), 9.11 (s, 1H).

Example 6

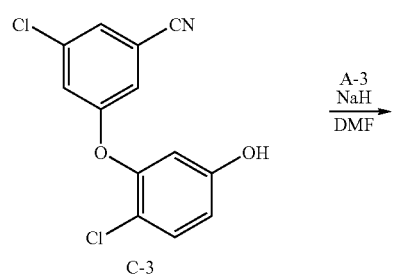

A-3
NaH
DMF

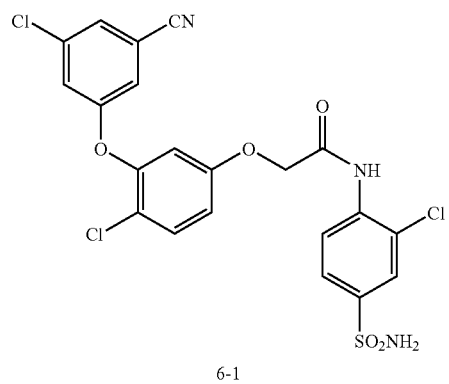

N-[4-(aminosulfonyl)-2-chlorophenyl]-2-[4-chloro-3-(3-chloro-5-cyanophenoxy)phenoxy]acetamide (6-1)

In a manner identical to that described in Example 1 above for the synthesis of 1-2, from (0.25 mmol) of 3-chloro-5-(2-chloro-5-hydroxyphenoxy)benzonitrile (C-3) and 82 mg (0.25 mmol) of N-[4-(aminosulfonyl)-2-chlorophenyl]-2-bromoacetamide(A-3) was obtained the desired product 6-1 as a white amorphous solid. HRMS: measured 525.9790; theoretical 525.9793. $^1$H NMR(DMSO-d$_6$): 4.88 (s, 2H), 7.04 (s, 2H), 7.40 (m, 1H), 7.47 (m, 3H), 7.60 (dd, 1H), 7.77 (dd, 1H), 7.82 (m, 1H), 7.91 (m, 1H), 8.04 (d, 1H), 9.75 (s, 1H).

Example 7

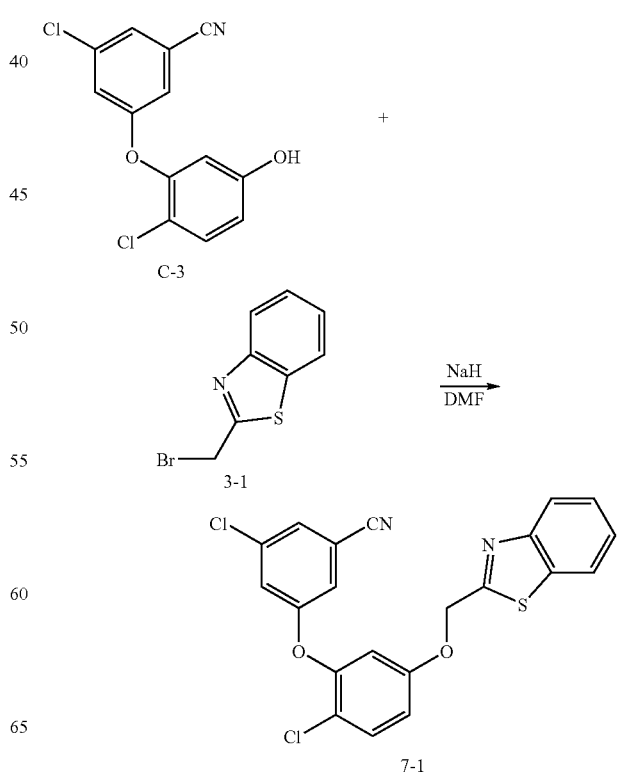

3-[5-(1,3-benzothiazol-2-ylmethoxy)-2-chlorophenoxy]-5-chlorobenzonitrile (7-1)

In a manner identical to that described above for the synthesis of 1-2, from 65 mg (0.232 mmol) of 3-chloro-5-(2-chloro-5-hydroxyphenoxy)benzonitrile (C-3), 6 mg (0.232 mmol) of NaH 60% dispersion, and 53 mg (0.232 mmol) of 2-(bromomethyl)-1,3-benzothiazole(3-1) was prepared the desired product 7-1 as a white solid. MS: M+=427.1. $^1$H NMR (CDCl$_3$): δ 8.03 (d, 1H), 7.92 (d, 1H), 7.52 (t, 1H), 7.43 (t, 1H), 7.33 (s, 1H), 7.13 (s, 1H), 7.02 (s, 1H), 6.93 (dd, 2H), 6.81 (s, 1H), 5.47 (s, 2H).

Example 8

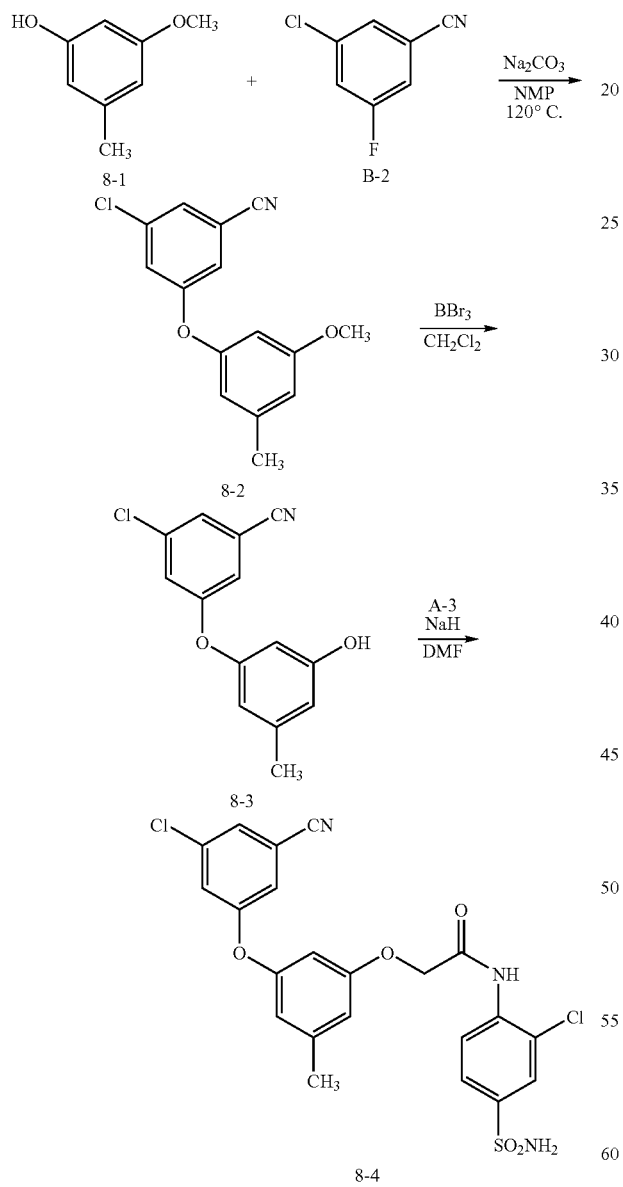

3-(3-methyl-5-methoxyphenoxy)benzonitrile(8-2)

In a manner identical to that described above for the synthesis of B-3, from 0.75 g (5.43 mmol) of 3-methyl-5-methoxyphenol(8-1) and 1.00 g (7.06 mmol) of 3-fluoro-5-chlorobenzonitrile (B-2) was obtained the desired product 8-2 as a clear oil. MS M+=274. $^1$H NMR(CDCl$_3$): 2.35 (s, 3H), 3.79 (s, 3H), 6.39 (m, 1H), 6.44 (m, 1H), 6.61 (m, 1H), 7.10 (m, 1H), 7.19 (m, 1H), 7.31 (m, 1H).

3-(3-methyl-5-hydroxyphenoxy)benzonitrile(8-3)

In a manner identical to that described in Intermediate B above for the synthesis of B-4, from 1.15 g (4.20 mmol) of 3-(3-methyl-5-methoxyphenoxy)benzonitrile(8-2) was obtained the desired product 8-3 as a pale greenish oil/solid. MS M+=260.

N-[4-(aminosulfonyl)-2-chlorophenyl]-2-[3-(3-chloro-5-cyanophenoxy)-5-methylphenoxy]acetamide (8-4)

In a manner identical to that described in Example 1 above for the synthesis of 1-2, from 80 mg (0.31 mmol) of 3-(3-methyl-5-hydroxyphenoxy)benzonitrile(8-3) and 100 mg (0.31 mmol) of N-[4-(aminosulfonyl)-2-chlorophenyl]-2-bromoacetamide(A-3) was obtained the desired product 8-4 as an amorphous white solid. HRMS: measured 506.0336, theoretical 506.0339. $^1$H NMR(DMSO-d$_6$): 2.30 (s, 3H), 4.83 (s, 2H), 6.60 (m, 2H), 6.77 (m, 1H), 7.40 (m, 1H), 7.45 (br s, 2H), 7.48 (m, 1H), 7.77 (m, 2H), 7.80 (m, 1H), 8.10 (dd, 1H), 9.78 (s, 1H).

Example 9

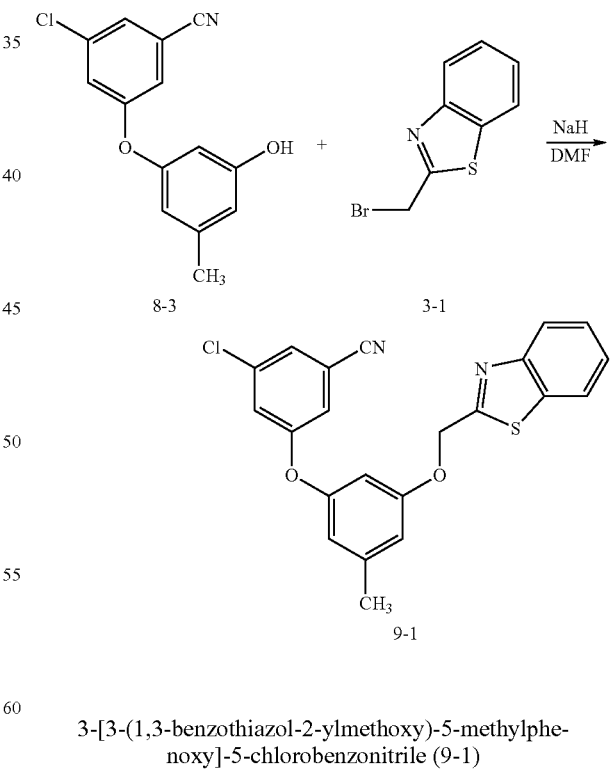

3-[3-(1,3-benzothiazol-2-ylmethoxy)-5-methylphenoxy]-5-chlorobenzonitrile (9-1)

In a manner identical to that described above for the synthesis of 1-2, from 100 mg (0.385 mmol) of 3-chloro-5-(3-hydroxy-5-methylphenoxy)benzonitrile(8-3), 22 mg (0.847 mmol) of NaH 60% dispersion, and 88 mg (0.385 mmol) of 2-(bromomethyl)-1,3-benzothiazole(3-1) was prepared the desired product 9-1 as a white solid. HRMS: measured 407.0612 theoretical 407.0616. $^1$H NMR(CDCl$_3$): δ 8.04 (d, 1H), 7.92 (d, 1 h), 7.51 (t, 1H), 7.42 (t, 1H), 7.32 (s, 1H), 7.18 (s, 1H), 7.10 (s, 1H), 6.74 (s, 1H), 6.54 (s, 1H), 6.50 (s, 1H).

Example 10

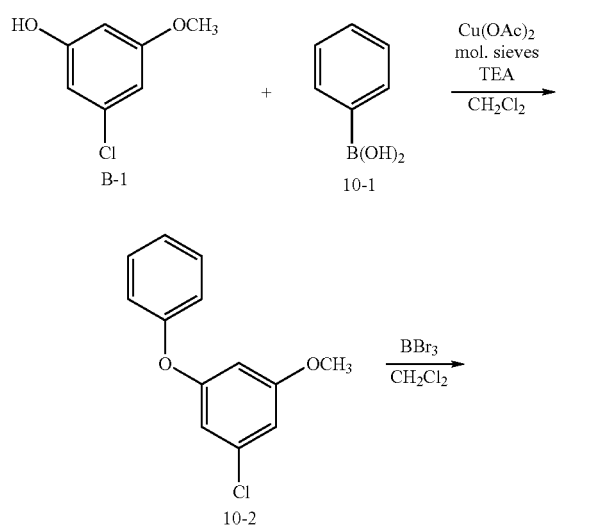

1-chloro-3-methoxy-5-phenoxybenzene(10-2)

In a manner identical to that described in Example 4 for the synthesis of 4-2, from 700 mg (4.41 mmol) of 3-chloro-5-methoxyphenol (B-1) and 1.08 g (8.82 mmol) of phenylboronic acid (10-1) was obtained the desired product 10-2 as a clear oil. MS M+=235. $^1$H NMR(CDCl$_3$): 3.76 (s, 3H), 6.42 (m, 1H), 6.55 (m, 1H), 6.62 (m, 1H), 7.02 (dd, 2H), 7.15 (t, 1H), 7.36 (t, 2H).

1-chloro-3-hydroxy-5-phenoxybenzene(10-3)

In a manner identical to that described in Intermediate B above for the synthesis of B-4, from 470 mg (1.80 mmol) of 1-chloro-3-methoxy-5-phenoxybenzene(10-2) was obtained the desired product 10-3 as a tan oil. MS M+=221.

N-[4-(aminosulfonyl)-2-chlorophenyl]-2-(3-chloro-5-phenoxyphenoxy)acetamide (10-4)

In a manner identical to that described in Example 1 above for the synthesis of 1-2, from 60 mg (0.27 mmol) of 1-chloro-3-hydroxy-5-phenoxybenzene(10-3) and 96 mg (0.29 mmol) of N-[4-(aminosulfonyl)-2-chlorophenyl]-2-bromoacetamide(A-3) was obtained desired product 10-4 as an amorphous white solid. MS M+=467. $^1$H NMR(CDCl$_3$): 4.63 (s, 2H), 6.42 (s, 2H), 6.57 (m, 1H), 6.65 (m, 1H), 6.75 (m, 1H), 7.05 (dd, 2H), 7.20 (t, 1H), 7.39 (t, 2H), 7.87 (dd, 1H), 8.03 (m, 1H), 8.60 (d, 1H), 9.09 (s, 1H).

Example 11

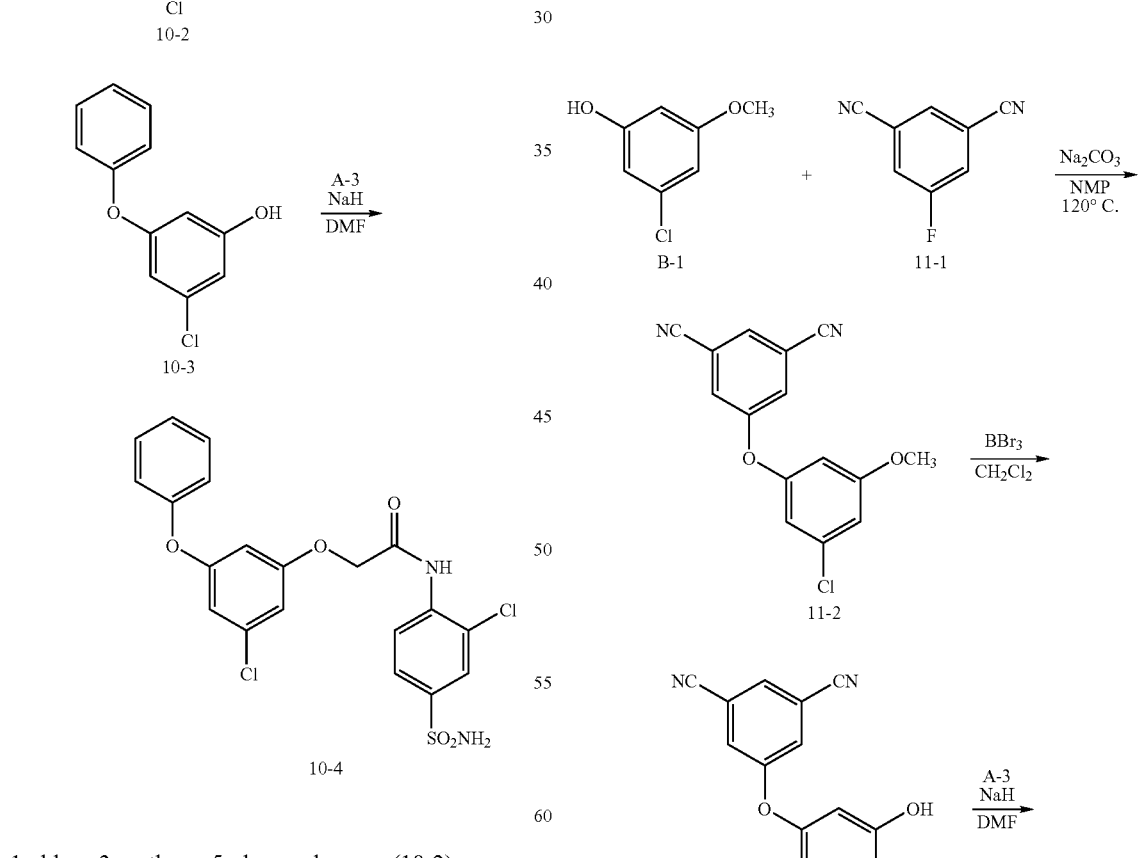

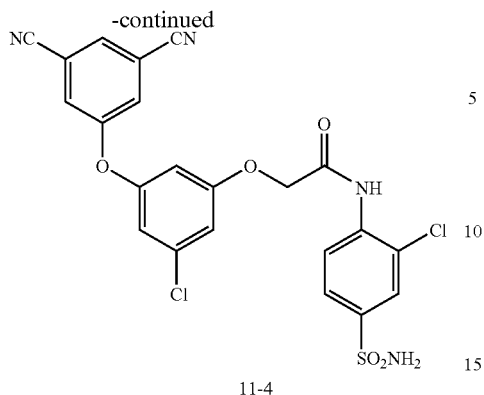

11-4

5-(3-chloro-5-methoxyphenoxy)isophthalonitrile(11-2)

In a manner identical to that described above in Intermediate B for the synthesis of B-3, from 0.56 g (3.53 mmol) of 3-chloro-5-methoxyphenol(B-1) and 0.67 g (4.59 mmol) of 5-fluoroisophthalonitrile(11-1) was obtained the desired product 11-2 as a white solid. MS M+=285. $^1$H NMR (CDCl$_3$): 6.49 (m, 1H), 6.64 (m, 1H), 6.83 (m, 1H), 7.45 (m, 2H), 7.64 (m, 1H).

5-(3-chloro-5-hydroxyphenoxy)isophthalonitrile(11-3)

In a manner identical to that described in Intermeidate B for the synthesis of B-4, from 625 mg (2.20 mmol) of 5-(3-chloro-5-methoxyphenoxy)isophthalonitrile(11-2) was obtained 130 mg of the desired product 11-3 as a white solid. MS M+1=271. $^1$H NMR(CDCl$_3$): 5.09 (s, 1H), 6.45 (m, 1H), 6.63 (m, 1H), 6.78 (m, 1H), 7.46 (m, 2H), 7.66 (m, 1H).

N-[4-(aminosulfonyl)-2-chlorophenyl]-2-[3-chloro-5-(3,5-dicyanophenoxy)phenoxy]acetamide (11-4)

In a manner identical to that described in Example 1 above for the synthesis of 1-2, from 75 mg (0.28 mmol) of 5-(3-chloro-5-hydroxyphenoxy)isophthalonitrile(11-3) and 91 mg (0.28 mmol) of N-[4-(aminosulfonyl)-2-chlorophenyl]-2-bromoacetamide(A-3) was obtained the desired product 11-4 as an amorphous white solid. MS M+=517. $^1$H NMR (DMSO-d$_6$): 4.90 (s, 2H), 6.83 (m, 1H), 6.90 (m, 1H), 7.06 (m, 1H), 7.47 (s, 2H), 7.78 (dd, 1H), 7.92 (m, 1H), 7.97 (m, 2H), 8.04 (d, 1H), 8.27 (s, 1H), 9.76 (s, 1H).

Example 12

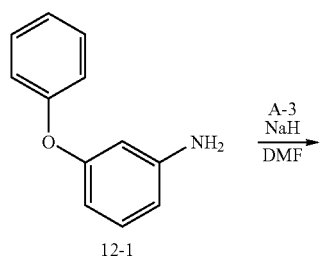

12-1

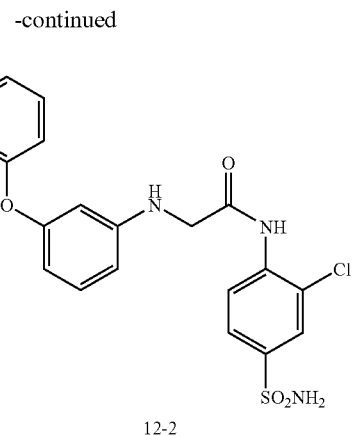

12-2

N$^1$-[4-(aminosulfonyl)-2-chlorophenyl]-N$^2$-(3-phenoxyphenyl)glycinamide (12-2)

In a manner identical to that described above for the synthesis of 1-2, from 119 mg (0.642 mmol) of (3-phenoxyphenyl)amine (12-1), 50 mg (1.927 mmol) of NaH 60% dispersion, and 210 mg (0.632 mmol) of N-[4-(aminosulfonyl)-2-chlorophenyl]-2-bromoacetamide (A-3) was prepared the desired product 12-2 as a white solid. MS: M+=433.1. $^1$H NMR (CDCl$_3$) δ 9.80 (s, 1H), 8.07 (d, 1H), 7.90 (s, 1H), 7.78 (d, 1H), 7.39 (t, 1H), 7.32 (t, 1H), 7.15 (t, 1H), 7.04 (d, 1H), 6.80 (d, 1H), 6.69 (s, 1H), 6.62 (d, 1H), 4.81 (s, 2H).

Example 13

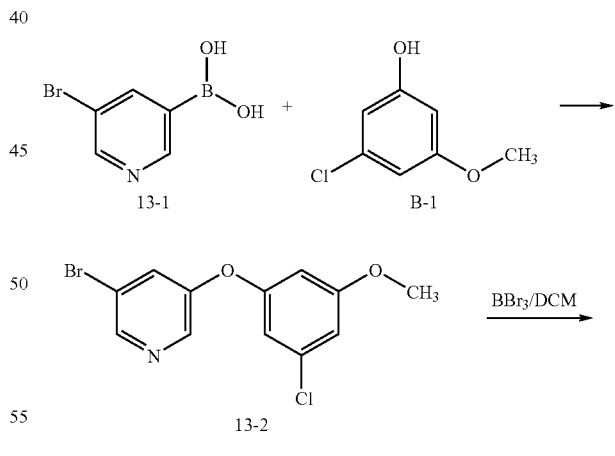

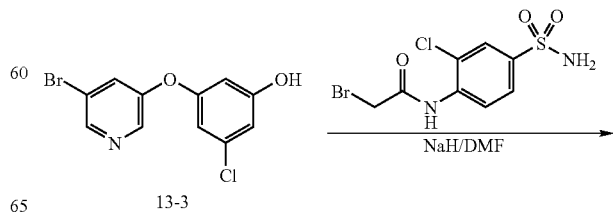

13-3

-continued

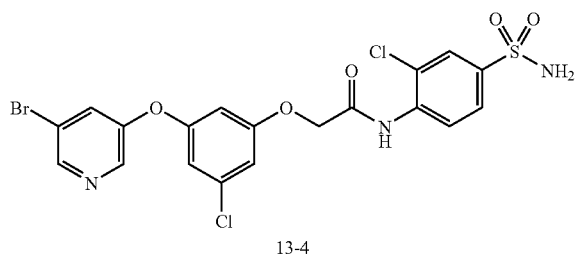

3-bromo-5-(3-chloro-5-methoxyphenoxy)pyridine (13-2)

A mixture of 372 mg (2.346 mmol) of 3-chloro-5-methoxyphenol (B-1), 947 mg (4.692 mmol) of 5-bromopyridine-3-boronic acid (13-1), 426 mg (2.346 mmol) of copper (II) acetate and 4.0 g of freshly activated powdered 4A molecular sieves was stirred in 20 mL of DCM in a screw top glass sealed tube. The reaction was then treated with 1.635 mL (11.73 mmol) of triethylamine and the vessel was loosely capped. The mixture was vigorously stirred at room temperature for 48 hours. The mixture was filtered through a pad of celite and the filtrate was concentrated in vacuo to a black residue. The residue was purified on a CombiFlash silica column eluted with an ethyl acetate:hexanes gradient to give the desired product 13-2 as an oil ($R_f$=0.7, EtOAc:hexanes 1:4). MS: M+1=314. $^1$H NMR(CDCl$_3$): 3.79 (s, 3H), 6.47 (m, 1H), 6.61 (m, 1H), 6.74 (m, 1H), 7.46 (m, 1H), 8.33 (d, 1H), 8.46 (d, 1H).

3-[(5-bromopyridin-3-yl)oxy]-5-chlorophenol (13-3)

In a manner identical to that described in Intermediate B above for the synthesis of B-4, from 170 mg (0.54 mmol) of 3-bromo-5-(3-chloro-5-methoxyphenoxy)pyridine (13-2) was prepared the desired product 13-3. MS: M+1=300. $^1$H NMR(DMSO-d$_6$): 6.41 (m, 1H), 6.62 (m, 1H), 6.65 (m, 1H), 7.86 (m, 1H), 8.42 (d, 1H), 8.55 (d, 1H), 10.24 (s, 1H).

N-[4-(aminosulfonyl)-2-chlorophenyl]-2-{3-[(5-bromopyridin-3-yl)oxy]-5-chlorophenoxy}acetamide (13-4)

In a manner identical to that described in Scheme 1 above for the synthesis of 1-2, from 36 mg (0.898 mmol) of sodium hydride, 108 mg (0.329 mmol) of N-[4-(aminosulfonyl)-2-chlorophenyl]-2-bromoacetamide (A-3) and 90 mg (0.299 mmol) of 3-[(5-bromopyridin-3-yl)oxy]-5-chlorophenol (13-3) was prepared the desired product 13-4. HRMS: measured 545.9306; theoretical 545.9287. $^1$H NMR(DMSO-d$_6$): 4.90 (s, 2H), 6.79 (t, 1H), 6.83 (t, 1H), 7.01 (t, 1H), 7.48 (s, 2H), 7.77 (dd, 1H), 7.84 (t, 1H), 7.91 (d, 1H), 8.01 (d, 1H), 8.47 (d, 1H), 8.54 (d, 1H).

Example 14

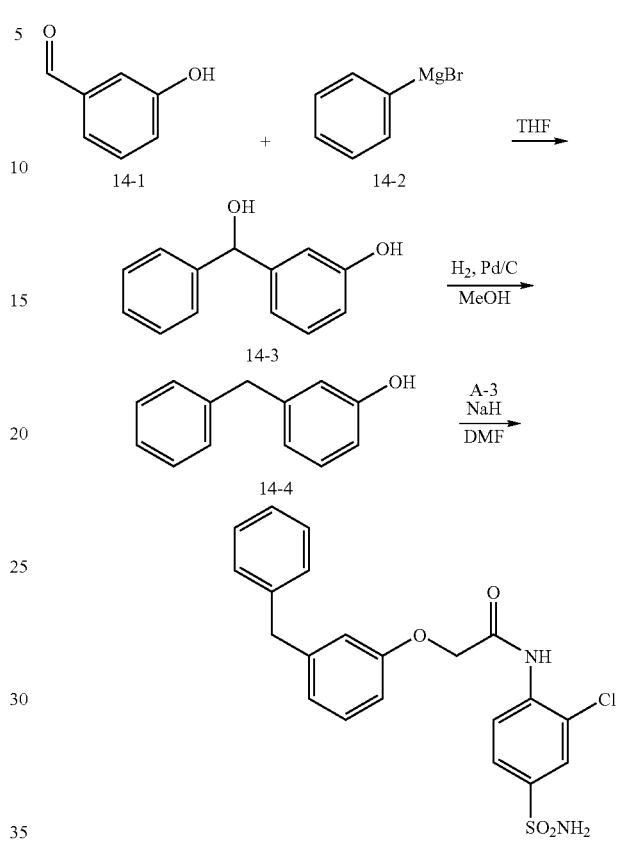

3-[hydroxy(phenyl)methyl]phenol(14-3)

A mixture of 202 mg (1.654 mmol) of 3-hydroxybenzaldehyde (14-1) in 5 mL THF was cooled to 0° C. in an ice-bath and then treated with 4.135 mL (1 M in THF) of a phenylmagnesium bromide solution (14-2) using a syringe. The mixture was stirred at 0° C. for one hour, and then refluxed an additional hour. The mixture was then concentrated in vacuo and the residue was taken up in diethyl ether, extracted with 1N HCl, washed with brine, dried (MgSO$_4$), filtered and concentrated in vacuo to give the desired crude product 14-3. MS: M+=199.3.

3-benzylphenol(14-4)

The crude 3-[hydroxy(phenyl)methyl]phenol (14-3) was taken up in 5 mL methanol and hydrogenated (1 atm, 5 mg Pd/C) for 5 hours. The mixture was then filtered through silica and concentrated in vacuo. The residue was purified by flash chromatography over silica gel with 1:2 ethyl acetate/hexanes to give the desired product 14-4 as a solid. MS: M+=184.3.

N-[4-(aminosulfonyl)-2-chlorophenyl]-2-(3-benzylphenoxy)acetamide(14-5)

In a manner identical to that described above for the synthesis of 1-2, from 31 mg (0.168 mmol) of 3-benzylphenol (14-4), 4 mg (0.168 mmol) of NaH 60% dispersion, and 55 mg (0.168 mmol) of N-[4-(aminosulfonyl)-2-chlorophenyl]-2-bromoacetamide (A-3) was prepared the desired product 14-5 as a white solid. MS: M+=431.1.

Example 15

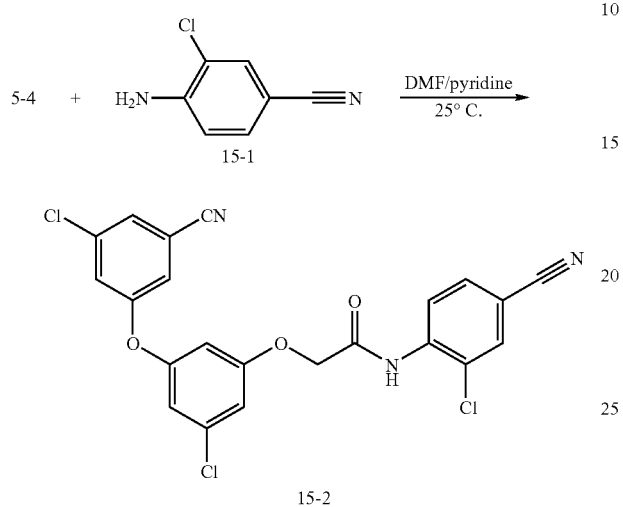

2-[3-chloro-5-(3-chloro-5-cyanophenoxy)phenoxy]-N-(2-chloro-4-cyanophenyl)acetamide (15-2)

In a manner similar to that described in Example 5 above for the synthesis of 5-6, from 27 mg (0.076 mmol) of [3-chloro-5-(3-chloro-5-cyanophenoxy)phenoxy]acetyl chloride (5-4), 23 mg (0.151 mmol) of 4-amino-3-chlorobenzonitrile (15-1) and 6 mg (0.076 mmol) of pyridine was prepared the desired product 15-2. MS (M+1): measured 472.1; theoretical 471.0. $^1$H NMR (CDCl$_3$): 4.67 (s, 2H), 6.60 (m, 1H), 6.74 (m, 1H), 6.88 (m, 1H), 7.15 (m, 1H), 7.24 (m, 1H), 7.42 (m, 1H), 7.61 (d, 1H), 7.73 (m, 1H), 8.67 (d, 1H), 9.08 (s, 1H).

Example 16

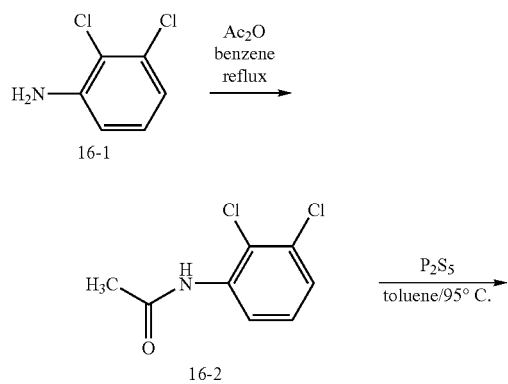

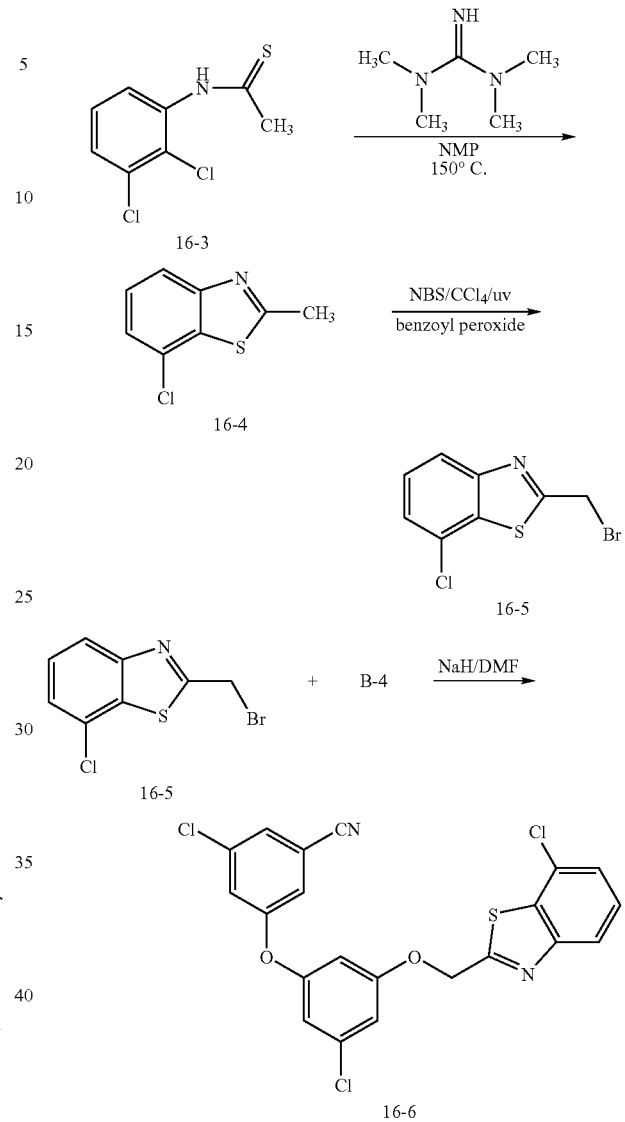

N-(2,3-dichlorophenyl)acetamide (16-2)

To a solution 2.06 g (12.71 mmol) of 2,3-dichloroaniline (16-1) in 10 mL of benzene cooled in an ice bath was added drop wise a 10 mL benzene solution of 1.95 g (19.07 mmol) of acetic anhydride. The reaction mixture was then brought to reflux for 1 hour, cooled to room temperature and filtered off the desired product 16-2. MS (M+1): theoretical 203.0; measured 204.1. $^1$H NMR (CDCl$_3$): 2.26 (s, 3H), 7.21 (m, 2H), 7.68 (m, 1H), 8.33 (m, 1H).

N-(2,3-dichlorophenyl)ethanethioamide (16-3)

As per a literature procedure (J Heterocyclic Chem., 14, 1073, (1997)), from 2.09 g (10.27 mmol) of N-(2,3-dichlorophenyl)acetamide (16-2) and 1.41 g (6.36 mmol) of phosphorus pentasulfide was obtained 1.34 g of the desired compound 16-3. MS (M+1): measured 220.1; theoretical 218.9. ¹H NMR (CDCl₃): 2.80 (s, 3H), 7.27 (m, 2H), 7.38 (m, 1H), 8.45 (d, 1H), 8.79 (s, 1H).

7-chloro-2-methyl-1,3-benzothiazole (16-4)

As per a literature procedure (J Heterocyclic Chem., 14, 1073, (1997)), from 1.31 g (5.95 mmol) of N-(2,3-dichlorophenyl)ethanethioamide (16-3) and 2.05 g (17.85 mmol) of 1,1,3,3-tetramethylguanidine was obtained the desired compound 16-4. MS (M+1): measured 184.1; theoretical 183.0. ¹H NMR (CDCl₃): 2.85 (s, 3H), 7.34 (m, 1H), 7.39 (t, 1H), 7.84 (d, 1H).

2-(bromomethyl)-7-chloro-1,3-benzothiazole (16-5)

A mixture of 900 mg (4.9 mmol) of 7-chloro-2-methyl-1,3-benzothiazole (16-4), 1.13 g (6.37 mmol) of N-bromosuccinimide and 47 mg (0.196 mmol) of benzoyl peroxide in CCl₄ (25mL) was refluxed under irradiation by a UV lamp for 4 hours. After this time the reaction was cooled to room temperature and the insolubles were filtered off. The reaction was purified on a silica column eluted with EtOAc:hexanes (3:97 to 1:1) and 80 mg of the desired product 16-5 was isolated. HRMS: measured 261.9080; theoretical 261.9087. ¹H NMR (CDCl₃): 4.80 (s, 2H), 7.43 (m, 2H), 7.92 (d, 1H).

3-chloro-5-{3-chloro-5-[(7-chloro-1,3-benzothiazol-2-yl)methoxy]phenoxy}benzonitrile (16-6)

In a manner similar to that described in Example 1 above for the synthesis of 1-2, from 47 mg (0.168 mmol) of 3-chloro-5-(3-chloro-5-hydroxyphenoxy)benzonitrile (B-4), 40 mg (0.152 mmol) of 2-(bromomethyl)-7-chloro-1,3-benzothiazole (16-5) and 7 mg (0.168 mmol) of 60% NaH dispersion was prepared the desired product 16-6. HRMS: measured 460.9687; theoretical 460.9680. ¹H NMR (CDCl₃): 5.45 (s, 2H), 6.62 (m, 1H), 6.69 (m, 1H), 6.92 (m, 1H), 7.15 (m, 1H), 7.21 (m, 1H), 7.38 (m, 1H), 7.43 (d, 1H), 7.47 (t, 1H), 7.92 (d, 1H).

Example 17

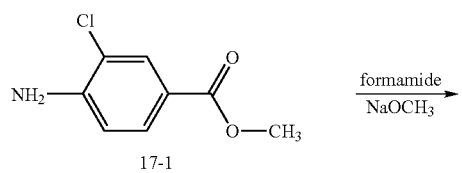
17-1

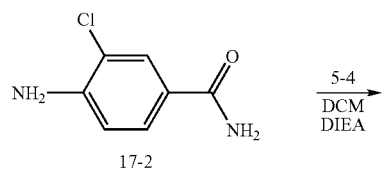
17-2

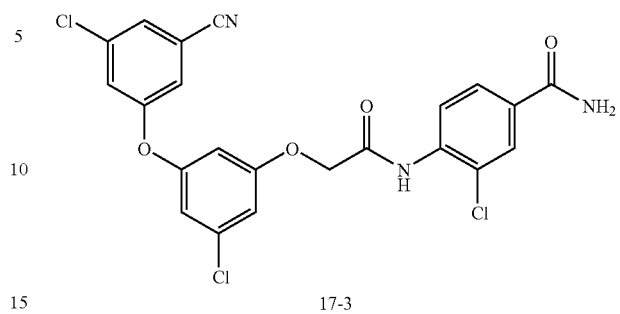
17-3

4-Amino-3-chlorobenzamide (17-2)

An anhydrous DMF solution of 1.00 g (5.39 mmol) of methyl 4-amino-3-chlorobenzoate (17-1), 728 mg (16.16 mmol) of formamide and 204 mg (3.77 mmol) of 5.5M sodium methoxide was stirred for 1 hour at 100° C. and then stirred overnight at room temperature. The reaction was poured into 2-propanol (60 mL) and then evaporated off the solvent. The resultant crude oil was purified on a silica column and eluted with DCM:MeOH:NH4OH (95:5:0.5 to 9:1: 0.1). Recovered the desired product 17-2. MS (M+1): measured 171.2; theoretical 170.0. ¹H NMR (DMSO): 5.86 (s, 2H), 6.75 (d, 1H), 7.01 (bs, 1H), 7.56 (dd, 1H), 7.66 (bs, 1H), 7.75 (m, 1H).

3-Chloro-4-({[3-chloro-5-(3-chloro-5-cyanophenoxy)phenoxy]acetyl}amino)benzamiide (17-3)

In a manner similar to that described in Example 5 above for the synthesis of 5-6, from 45 mg (0.126 mmol) of 3-chloro-5-(3-chloro-5-cyanophenoxy)phenoxy]acetyl chloride (5-4), 30 mg (0.177 mmol) of 4-amino-3-chlorobenzamide (17-2) and 65 mg (0.505 mmol) of DIEA was prepared the desired product 17-3. HRMS: measured 490.0120; theoretical 490.0123. ¹H NMR (DMSO): 4.89 (s, 2H), 6.80 (t, 1H), 6.89 (t, 1H), 7.03 (t, 1H), 7.47 (bs, 1H), 7.54 (t, 1H), 7.60 (m, 1H), 7.85 (m, 2H), 7.92 (m, 1H), 8.00 (d, 1H), 8.05 (bs, 1H), 9.75 (s, 1H).

Example 18

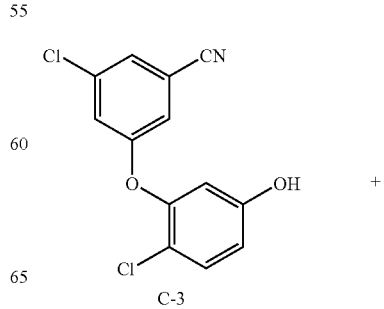
C-3

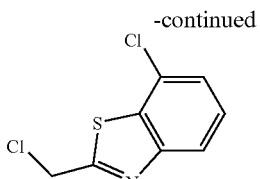

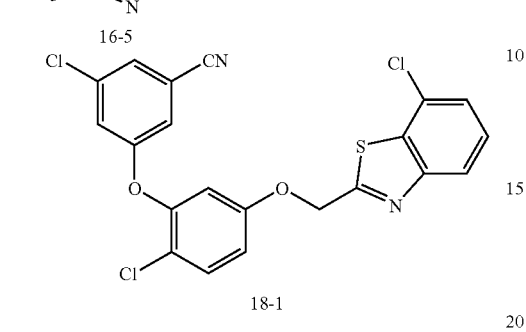

3-chloro-5-{2-chloro-5-[(7-chloro-1,3-benzothiazol-2-yl)methoxy]phenoxy}benzonitrile (18-1)

In a manner similar to that described in Example 1 above for the synthesis of 1-2, from 47 mg (0.168 mmol) of 3-chloro-5-(2-chloro-5-hydroxyphenoxy)benzonitrile (C-3), 40 mg (0.152 mmol) of 2-(bromomethyl)-7-chloro-1,3-benzothiazole (16-5) and 7 mg (0.168 mmol) of 60% NaH dispersion was prepared the desired product 18-1. HRMS: measured 460.9688; theoretical 460.9680. $^1$H NMR (CDCl$_3$): 5.46 (s, 2H), 6.81 (d, 1H), 6.93 (dd, 1H), 7.03 (m, 1H), 7.13 (m, 1H), 7.34 (m, 1H), 7.45 (m, 3H), 7.91 (d, 1H).

Example 19

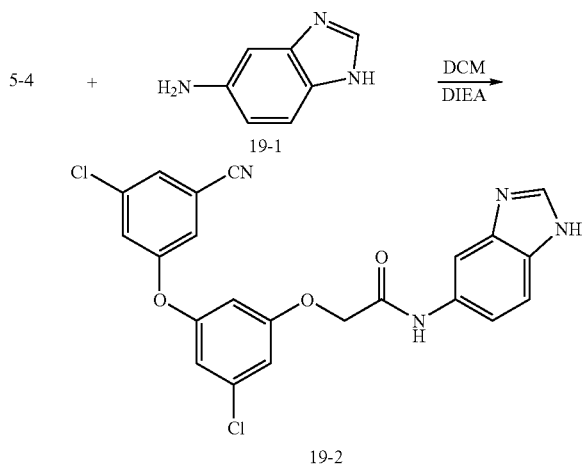

N-(1H-benzimidazol-5-yl)-2-[3-chloro-5-(3-chloro-5-cyanophenoxy)phenoxy]acetamide (19-2)

In a manner similar to that described in Example 5 above for the synthesis of 5-6, from 48 mg (0.135 mmol) of [3-chloro-5-(3-chloro-5-cyanophenoxy)phenoxy]acetyl chloride (5-4), 18 mg (0.135 mmol) of 1H-benzimidazol-5-amine (19-1) and 70 mg (0.538 mmol) of DIEA was prepared the desired product 19-2. HRMS: measured 453.0510; theoretical 453.0516. $^1$H NMR (DMSO): 4.77 (s, 2H), 6.79 (s, 1H), 6.86 (s, 1H), 7.03 (s, 1H), 7.30 (bs, 1H), 7.55 (m, 2H), 7.61 (s, 1H), 7.84 (s, 1H), 8.02 (bs, 1H), 8.16 (s, 1H), 10.04 (bs, 1H), 12.38 (bs, 1H).

Example 20

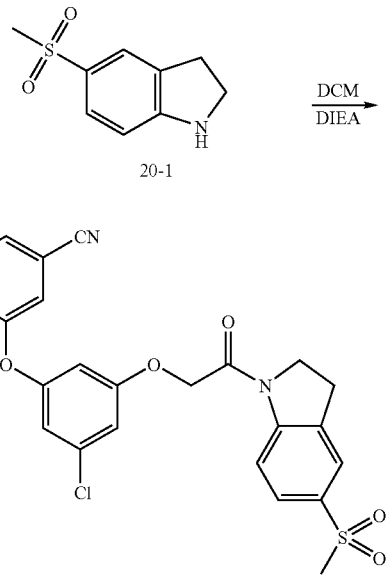

3-Chloro-5-(3-chloro-5-{2-[5-(methylsulfonyl)-2,3-dihydro-1H-indol-1H-indol-1-yl]-2-oxoethoxy}phenoxy)benzonitrile (20-2)

In a manner similar to that described in Example 5 above for the synthesis of 5-6, from 58 mg (0.163 mmol) of [3-chloro-5-(3-chloro-5-cyanophenoxy)phenoxy]acetyl chloride (5-4), 35 mg (0.179 mmol) of 5-(methylsulfonyl)indoline (20-1) and 84 mg (0.651 mmol) of DIEA was prepared the desired product 20-2. MS (M+1): measured 517.1; theoretical 516.0. $^1$H NMR (CDCl$_3$): 3.04 (s, 3H), 3.35 (t, 2H), 4.24 (t, 2H), 4.78 (s, 2H), 6.59 (t, 1H), 6.69 (t, 1H), 6.83 (t, 1H), 7.15 (m, 1H), 7.24 (t, 1H), 7.39 (m, 1H), 7.78 (bs, 1H), 7.82 (dd, 1H), 8.36 (m, 1H).

Example 21

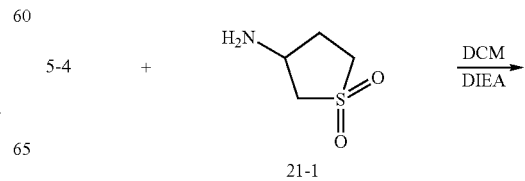

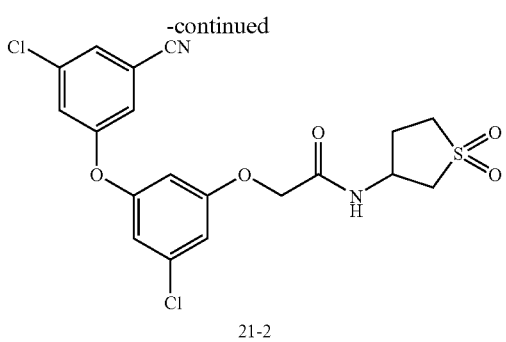

21-2

2-[3-Chloro-5-(3-chloro-5-cyanophenoxy)phenoxy]-N-(1,1-dioxidotetrahydrothien-3-yl)acetamide (21-2)

In a manner similar to that described in Example 5 above for the synthesis of 5-6, from 45 mg (0.126 mmol) of [3-chloro-5-(3-chloro-5-cyanophenoxy)phenoxy]acetyl chloride (5-4), 17 mg (0.126 mmol) of (1,1-dioxidotetrahydro-3-thienyl)amine (21-1) and 65 mg (0.505 mmol) of DIEA was prepared the desired product 21-2. HRMS: measured 455.0240; theoretical 455.0230. $^1$H NMR (CDCl$_3$): 2.33 (m, 1H), 2.56 (m, 1H), 3.02 (dd, 1H), 3.18 (m, 2H), 3.40 (m, 1H), 4.49 (s, 2H), 4.88 (m, 1H), 6.53 (t, 1H), 6.72 (t, 1H), 6.80 (t, 1H), 7.06 (bd, 1H), 7.15 (m, 1H), 7.24 (m, 1H), 7.41 (m, 1H).

Example 22

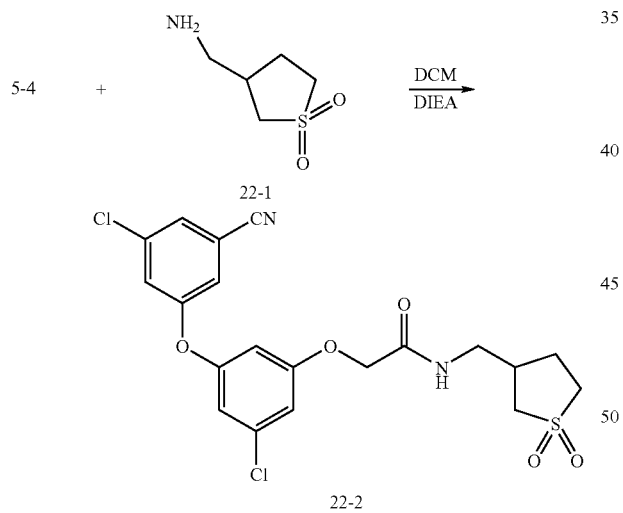

22-2

2-[3-Chloro-5-(3-chloro-5-cyanophenoxy)phenoxy]-N-[(1,1-dioxidotetrahydrothien-3-yl)methyl]acetamide (22-2)

In a manner similar to that described in Example 5 above for the synthesis of 5-6, from 48 mg (0.134 mmol) of [3-chloro-5-(3-chloro-5-cyanophenoxy)phenoxy]acetyl chloride (5-4), 20 mg (0.134 mmol) of (1,1-dioxidotetrahydro-3-thienyl)methyl]amine (22-1) and 69 mg (0.536 mmol) of DIEA was prepared the desired product 22-2. HRMS: measured 469.0386; theoretical 469.0386. $^1$H NMR (CDCl$_3$): 1.96 (m, 1H), 2.34 (m, 1H), 2.79 (m, 2H), 3.07 (m, 1H), 3.21 (m, 2H), 3.48 (m, 1H), 3.55 (m, 1H), 4.49 (s, 2H), 6.51 (t, 1H), 6.72 (m, 2H), 6.79 (t, 1H), 7.15 (m, 1H), 7.25 (m, 1H), 7.42 (m, 1H).

Example 23

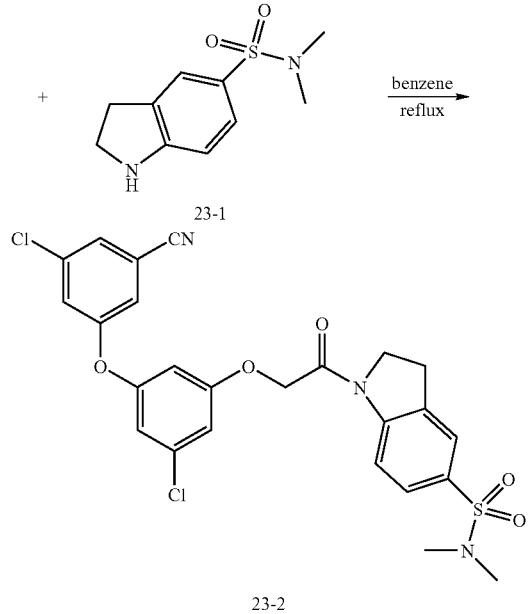

23-2

1-{[3-Chloro-5-(3-chloro-5-cyanophenoxy)phenoxy]acetyl}-N,N-dimethylindoline-5-sulfonamide (23-2)

41 mg (0.115 mmol) of [3-chloro-5-(3-chloro-5-cyanophenoxy)phenoxy]acetyl chloride (5-4) and 26 mg (0.115 mmol) of N,N-dimethylindoline-5-sulfonamide (23-1) were refluxed in benzene. When the reaction was complete the benzene was evaporated off and the residue was purified on a silica column eluted with EtOAc:hexanes (3:97 to 1:1). Recovered the desired compound 23-2. HRMS: measured 546.0665; theoretical 546.0652. $^1$H NMR (CDCl$_3$): 2.70 (s, 6H), 3.35 (t, 2H), 4.23 (t, 2H), 4.78 (bs, 2H), 6.59 (t, 1H), 6.68 (t, 1H), 6.83 (m, 1H), 7.15 (m, 1H), 7.24 (m, 1H), 7.39 (m, 1H), 7.63 (bs, 1H), 7.66 (bd, 1H), 8.34 (bd, 1H).

Example 24

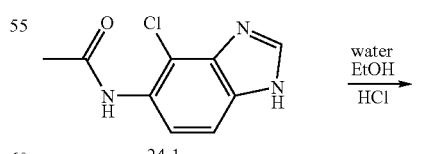

24-1

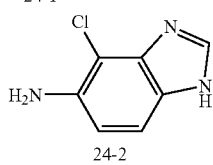 

24-2

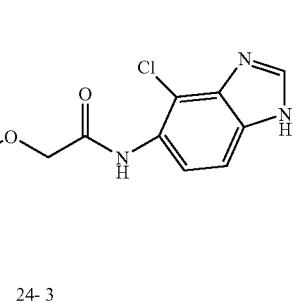

24-3

4-Chloro-1H-benzimidazol-5-amine (24-2)

58 mg (0.277 mmol) of N-(4-chloro-1H-benzimidazol-5-yl)acetamide (24-1) was suspended in a mixture of water, ethanol and concentrated HCl (0.06:1:0.4) for a total of 1 mL. The suspension was stirred and heated at 85° C. under nitrogen for 1 hour and after this time everything was soluble. The heat was turned off the solution was stirred overnight. The reaction was quenched with saturated $NaHCO_3$. The pH was adjusted to 8 by adding solid $NaHCO_3$ and $Na_2CO_3$. Extracted the reaction with ethyl acetate, dried, filtered and evaporated to recover the desired product 24-2. MS (M+1): measured 168.2; theoretical 167.0. $^1$H NMR ($CD_3OD$): 6.75 (dd, 1H), 7.37 (d, 1H), 7.93 (s, 1H).

N-(4-Chloro-1H-benzimidazol-5-yl)-2-[3-chloro-5-(3-chloro-5-cyanophenoxy)phenoxy]acetamide (24-3)

In a manner similar to that described in Example 23 above for the synthesis of 23-2, from 48 mg (0.134 mmol) of [3-chloro-5-(3-chloro-5-cyanophenoxy)phenoxy]acetyl chloride (5-4) and 27 mg (0.162 mmol) of 4-chloro-1H-benzimidazol-5-amine (24-2) was prepared the desired product 24-3. HRMS: measured 487.0145; theoretical 487.0126. $^1$H NMR (DMSO): 4.84 (s, 2H), 6.81 (s, 1H), 6.89 (s, 1H), 7.05 (s, 1H), 7.39 (d, 1H), 7.55 (m, 2H), 7.61 (s, 1H), 7.86 (s, 1H), 8.45 (s, 1H), 9.85 (s, 1H).

Example 25

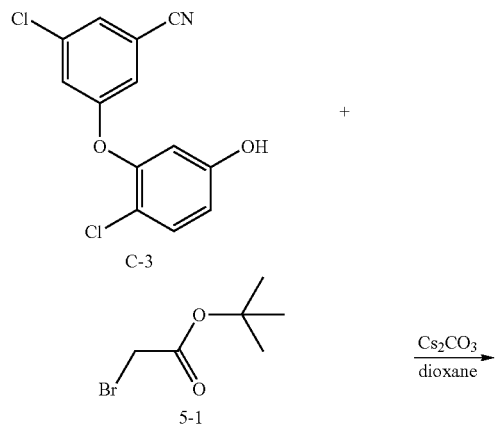

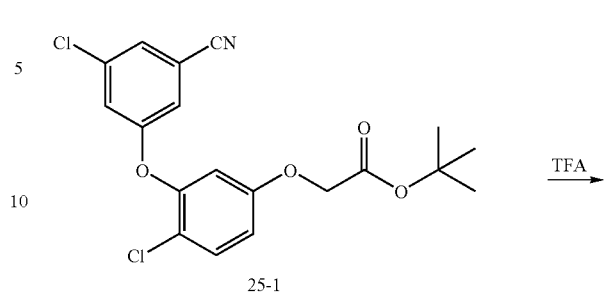

t-butyl [4-chloro-3-(3-chloro-5-cyanophenoxy)phenoxy]acetate(25-1)

In a manner identical to that described in Example 5 for the synthesis of 5-2 from 700 mg (2.50 mmol) 3-chloro-5-(2-chloro-5-hydroxyphenoxy)benzonitrile (C-3) was obtained 935 mg of the desired product 25-1 as an orange oil. The crude product was used as is without further characterization and was immediately carried on to the next step.

[4-chloro-3-(3-chloro-5-cyanophenoxy)phenoxy] acetic acid(25-2)

In a manner identical to that described above in Example 5 for the synthesis of 5-2 from 480 mg (1.22 mmol) of t-butyl [4-chloro-3-(3-chloro-5-cyanophenoxy)phenoxy]acetate (25-1) was obtained the desired product 25-2 as a tan amorphous solid. The crude acid was used is in the next step without further purification.

[4-chloro-3-(3-chloro-5-cyanophenoxy)phenoxy] acetyl chloride(25-3)

A solution of 410 mg (1.21 mmol) of [4-chloro-3-(3-chloro-5-cyanophenoxy)phenoxy]acetic acid(25-2) in 4 mL of thionyl chloride was heated at reflux for 24 hours (note—shorter reaction times lead to incomplete conversion). The reaction was cooled to room temperature and was concentrated in vacuo to give the desired product 25-3 as an oil. $^1$H NMR (CDCl$_3$): 4.94 (s, 2H), 6.68 (d, 1H), 6.79 (dd, 1H), 7.03 (m, 1H), 7.14 (m, 1H), 7.36 (t, 1H), 7.45 (d, 1H).

2-[4-chloro-3-(3-chloro-5-cyanophenoxy)phenoxy]-N-[2-chloro-4-(methylsulfonyl)phenyl]acetamide (25-4)

A solution of 64 mg (0.18 mmol) of [4-chloro-3-(3-chloro-5-cyanophenoxy)phenoxy]acetyl chloride(25-3) and 37 mg (0.18 mmol) of 2-chloro-4-methylsulfonylaniline (5-5) in 3 mL of benzene was heated at reflux in an nitrogen atmosphere for 1 hour. The reaction was cooled to room temp. and concentrated in vacuo to give a dark oil. The crude oil was purified by reversed phase prep LC to give the pure desired product 254 as a white amorphous solid. MS M+=525. $^1$H NMR (CDCl$_3$): 3.07 (s, 3H), 4.69 (s, 2H), 6.79 (d, 1H), 6.92 (dd, 1H), 7.01 (m, 1H), 7.16 (m, 1H), 7.37 (t, 1H), 7.50 (d, 1H), 7.88 (dd, 1H), 8.02 (d, 1H), 8.74 (d, 1H), 9.12 (br s, 1H).

Example 26

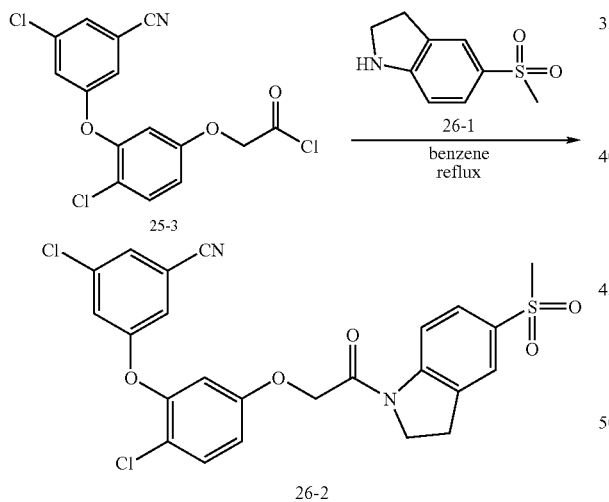

3-chloro-5-(2-chloro-5-{2-[5-(methylsulfonyl)-2,3-dihydro-1H-indol-1-yl]-2-oxoethoxy}phenoxy)benzonitrile (26-2)

In a manner identical to that described in Example 25 for the synthesis of 25-4, from 75 mg (0.21 mmol) of [4-chloro-3-(3-chloro-5-cyanophenoxy)phenoxy]acetyl chloride(25-3) and 42 mg (0.21 mmol) of 5-(methylsulfonyl)indoline (26-1) was obtained the desired product 26-2 as an amorphous white solid. MS M+=517. $^1$H NMR (CDCl$_3$): 3.03 (s, 3H), 3.34 (t, 2H), 4.25 (t, 2H), 4.79 (s, 2H), 6.76 (d, 1H), 6.88 (dd, 1H), 7.02 (m, 1H), 7.16 (m, 1H), 7.35 (m, 1H), 7.42 (d, 1H), 7.78 (m, 1H), 7.82 (dd, 1H), 8.36 (d, 2H).

Example 27

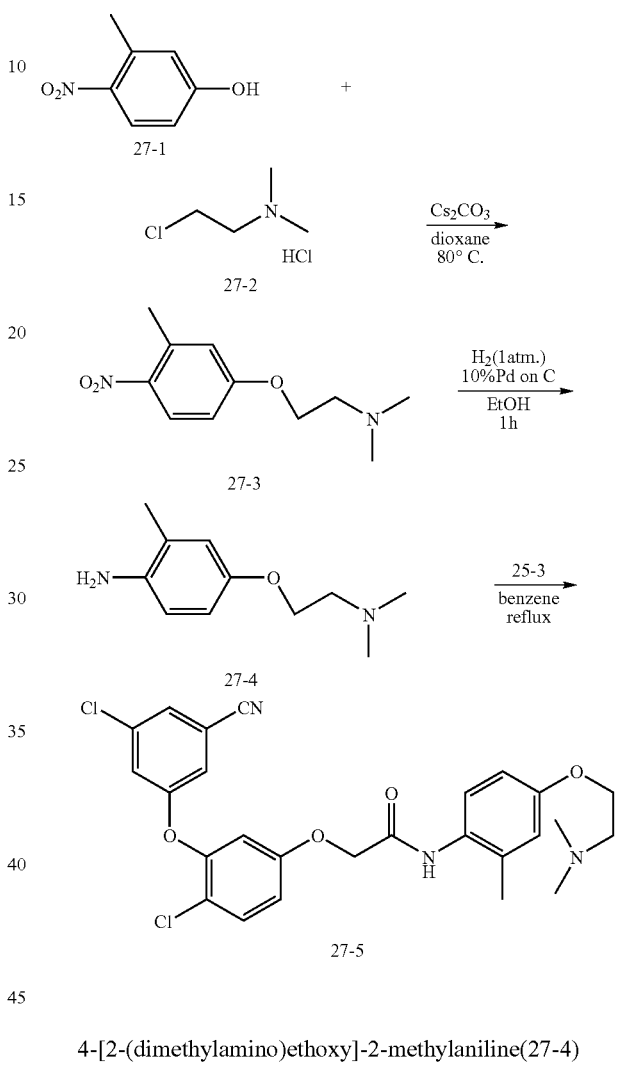

4-[2-(dimethylamino)ethoxy]-2-methylaniline(27-4)

A mixture of 1.00 g (6.53 mmol) of 3-methyl-4-nitrophenol (27-1) and 4.89 g (15.02 mmol) of cesium carbonate in 25 mL anhydrous dioxane was stirred at room temp. for approx. 45 minutes The reaction was treated with 1.23 g (8.50 mmol) of (2-chloroethyl)dimethylamine hydrochloride, and the resulting mixture was stirred at 80° C. for 18 hours. The reaction was cooled to room temperature, and was poured into 75 mL of water. The resulting mixture was extracted twice with ethyl acetate (35 mL each), and the combined extracts were washed with brine, dried (anhydrous MgSO$_4$), and concentrated in vacuo to give 1.27 g of alkylated product 27-3 as a dark oil. The oil was immediately dissolved in 20 mL of abs. ethanol, and the solution hydrogenated at 1 atm. (balloon) over 300 mg of 10% Pd on C catalyst. After 1 hour, the reaction was filtered through a pad of Celite, and the filtrate concentrated in vacuo to give the desired product 24-7 as dark brown oil. MS M+=195.

2-[4-chloro-3-(3-chloro-5-cyanophenoxy)phenoxy]-N-{4-[2-(dimethylamino)ethoxy]-2-methylphenyl}acetamide (27-5)

In a manner identical to that described in Example 25 for the synthesis of 25-4, from 58 mg (0.16 mmol) of [4-chloro-3-(3-chloro-5-cyanophenoxy)phenoxy]acetyl chloride(25-3) and 32 mg (0.16 mmol) of 4-[2-(dimethylamino)ethoxy]-2-methylaniline(27-4) was obtained the desired product 27-5 as an amorphous white solid. MS M+=514. $^1$H NMR (DMSO-$d_6$): 2.10 (s, 3H), 2.86 (d, 6H), 3.50 (t, 2H), 4.27 (t, 2H), 4.74 (s, 2H), 6.82 (dd, 1H), 6.87 (m, 1H), 6.99 (m, 1H), 7.03 (dd, 1H), 7.20 (d, 1H), 7.42 (m, 1H), 7.47 (m, 1H), 7.60 (d, 1H), 7.83 (m, 1H), 9.55 (br s, 1H).

Example 28

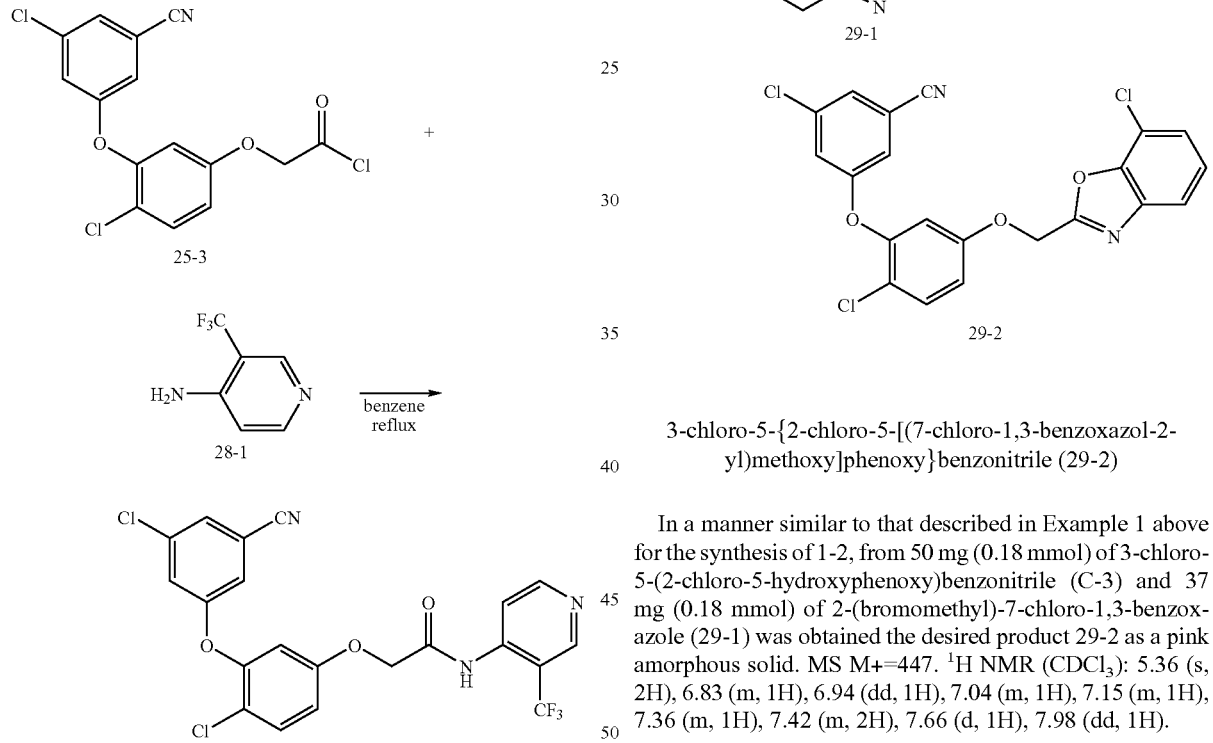

2-[4-chloro-3-(3-chloro-5-cyanophenoxy)phenoxy]-N-[3-(trifluoromethylpyridin-4-yl]acetamide (28-2)

In a manner identical to that described in Example 25 for the synthesis of 25-4, from 63 mg (0.18 mmol) of [4-chloro-3-(3-chloro-5-cyanophenoxy)phenoxy]acetyl chloride(25-3) and 29 mg (0.18 mmol) of 3-(trifluoromethyl)pyridin-4-amine was obtained the desired product 28-2 (TFA salt) as an amorphous white powder. MS M+=482. $^1$H NMR (CDCl$_3$): 4.64 (s, 2H), 6.75 (d, 1H), 6.88 (dd, 1H), 7.02 (m, 1H), 7.15 (m, 1H), 7.24 (m, 1H), 7.37 (m, 1H), 7.50 (d, 1H), 8.58 (br s, 1H), 8.80 (br s, 1H), 9.02 (s, 1H).

Example 29

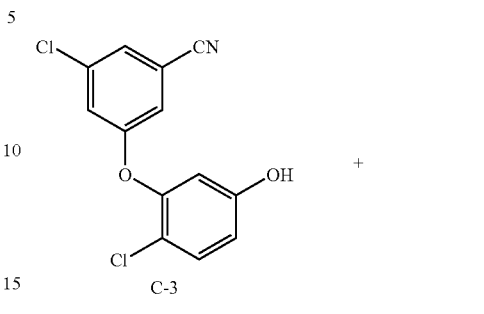

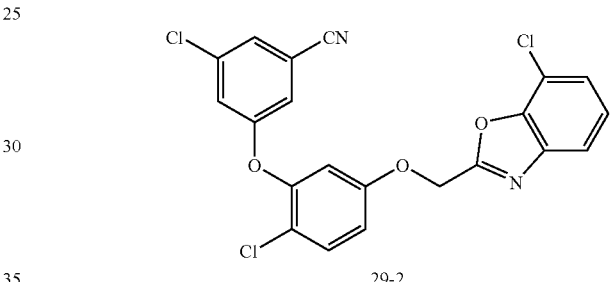

3-chloro-5-{2-chloro-5-[(7-chloro-1,3-benzoxazol-2-yl)methoxy]phenoxy}benzonitrile (29-2)

In a manner similar to that described in Example 1 above for the synthesis of 1-2, from 50 mg (0.18 mmol) of 3-chloro-5-(2-chloro-5-hydroxyphenoxy)benzonitrile (C-3) and 37 mg (0.18 mmol) of 2-(bromomethyl)-7-chloro-1,3-benzoxazole (29-1) was obtained the desired product 29-2 as a pink amorphous solid. MS M+=447. $^1$H NMR (CDCl$_3$): 5.36 (s, 2H), 6.83 (m, 1H), 6.94 (dd, 1H), 7.04 (m, 1H), 7.15 (m, 1H), 7.36 (m, 1H), 7.42 (m, 2H), 7.66 (d, 1H), 7.98 (dd, 1H).

Example 30

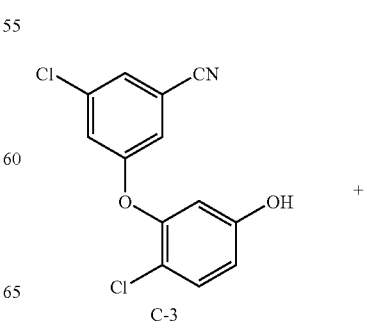

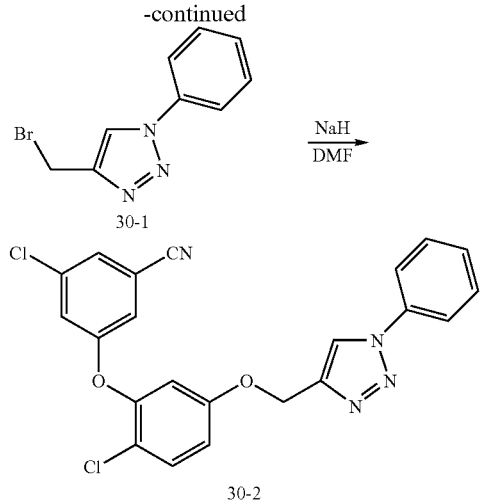

3-chloro-5-{2-chloro-5-[(1-phenyl-1H-1,2,3-triazol-4-yl)methoxy]phenoxy}benzonitrile (30-2)

In a manner similar to that described in Example 1 above for the synthesis of 1-2, from 50 mg (0.18 mmol) of 3-chloro-5-(2-chloro-5-hydroxyphenoxy)benzonitrile (C-3) and 43 mg (0.18 mmol) of 4-(bromomethyl)-1-phenyl-1H-1,2,3-triazole (30-1) was obtained the desired product 30-2 as an amorphous crusty white solid. MS M+=437. $^1$H NMR (CDCl$_3$): 5.22 (s, 2H), 6.79 (d, 1H), 6.92 (dd, 1H), 7.02 (m, 1H), 7.13 (m, 1H), 7.30 (m, 1H), 7.37 (t, 1H), 7.42 (d, 1H), 7.48 (t, 2H), 7.86 (s, 1H), 8.03 (d, 2H).

Example 31

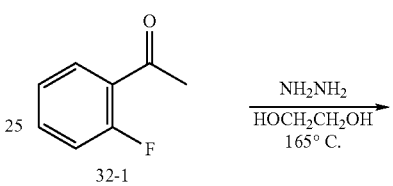

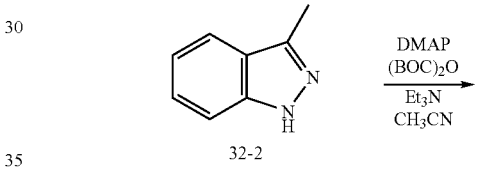

3-chloro-5-{2-chloro-5-[(1-methyl-1H-benzimidazol-2-yl)methoxy]phenoxy}benzonitrile (31-2)

In a manner similar to that described in Example 1 above for the synthesis of 1-2, from 50 mg (0.18 mmol) of 3-chloro-5-(2-chloro-5-hydroxyphenoxy)benzonitrile (C-3) and 33 mg (0.18 mmol) of 2-(chloromethyl)-1-methyl-1H-benzimidazole (31-1) was obtained the desired product 31-2 (TFA salt) as an amorphous fluffy white powder. MS M+=424. $^1$H NMR (CDCl$_3$): 4.03 (s, 3H), 5.66 (s, 2H), 6.88 (d, 1H), 6.99 (m, 1H), 7.03 (dd, 1H), 7.14 (m, 1H), 7.35 (m, 1H), 7.45 (d, 1H), 7.49 (m, 3H), 7.93 (d, 1H).

Example 32

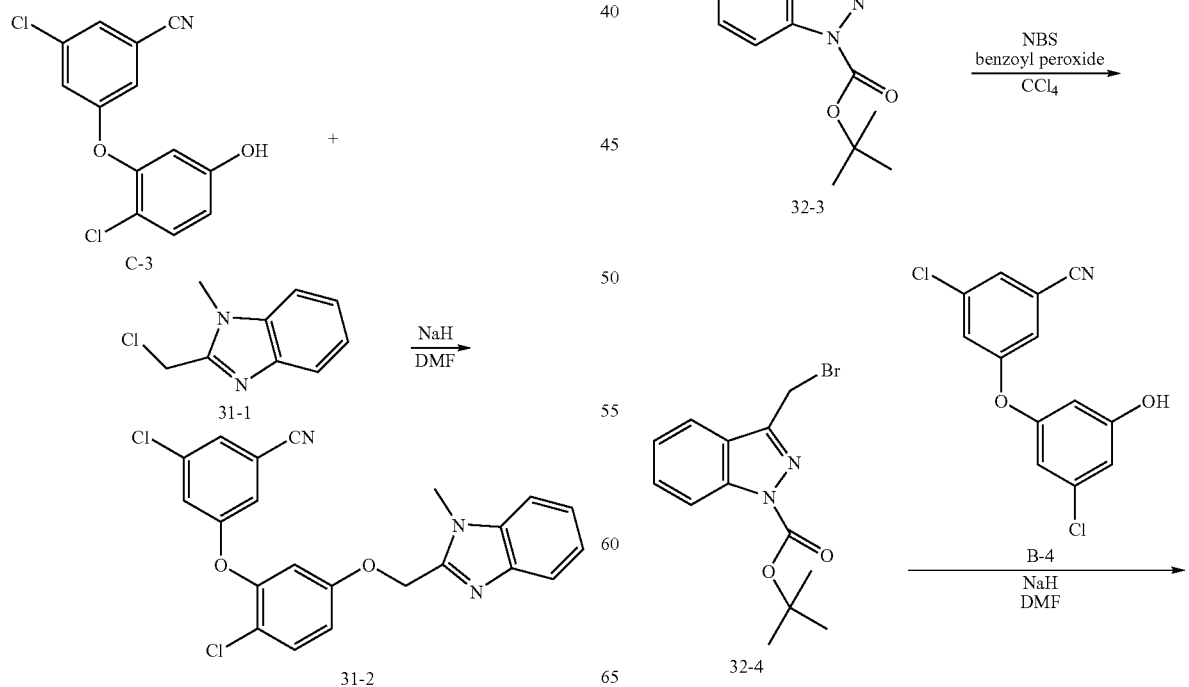

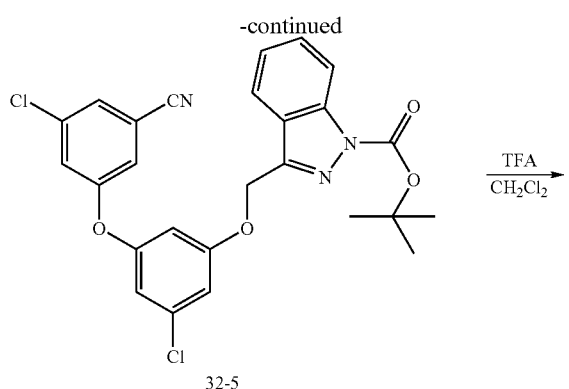

3-Methylindazole (32-2)

A stirred solution of 2.0 g (14.48 mmol) of 2-fluoroacetophenone (32-1) in 10 mL of ethylene glycol under nitrogen was treated with 473 uL (15.06 mmol) of hydrazine. This solution was stirred for 2 hours at room temperature and then heated at 165° C. for 40 hours. The solution was cooled to room temperature, poured into $CH_2Cl_2$ (25 mL), and extracted with $H_2O$ (2×50 mL). The organic portions were combined, dried ($MgSO_4$), filtered and conc. in vacuo. Purification of the crude material by recrystallization from hexanes/$CHCl_3$ gave the desired product 32-2 as a tan solid. $^1H$ NMR (DMSO-$d_6$): δ 7.70 (d, 1H), 7.42 (m, 2H), 7.17 (dd, 1H), 2.60 (s, 3H).

1-(tert-butyl)-3-methyl-1H-indazole-1-carboxylate (32-3)

A stirred solution of 610 mg (4.61 mmol) of 32-2 in 5 mL of acetonitrile under nitrogen was treated with 113 mg (0.92 mmol) of DMAP and 704 uL (5.08 mmol) of triethylamine. This mixture was cooled to 0° C. in an icebath. A solution of 1.21 g (5.54 mmol) of $(BOC)_2O$ in 10 mL acetonitrile was then added dropwise using an addition funnel. Upon completion of addition, the icebath was removed and the mixture was stirred for an additional 3 hours at room temperature. Solvent was removed in vacuo, and the residue was partitioned between ether and $H_2O$. The pH was adjusted to 2 with 1 N HCl, and the organic layer was separated, dried ($MgSO_4$), filtered and concentrated in vacuo to an orange oil. This crude material was purified by flash chromatography over silica gel with 1:4 ethyl acetate/hexanes to give 956 mg of the desired product 32-3 as a solid. MS: M+1=233.3.

1-(tert-butyl)-3-(bromomethyl)-1H-indazole-1-carboxylate(32-4)

A stirred solution of 300 mg (1.29 mmol) of 32-3 in 15 mL of $CCl_4$ was heated to reflux, and then a mixture of 253 mg (1.42 mmol) of NBS and 31 mg (0.13 mmol) of benzoyl peroxide was added portion-wise over 5 min as a solid. The resulting solution was heated at reflux for 4.5 hours and then allowed to cool to room temperature. The reaction mixture was filtered through a pad of Celite to remove precipitated succinimide, and the filtrate was concentrated in vacuo. The crude residue was purified by flash chromatography over silica gel with 1:3 ethyl acetate/hexanes to give the desired product 32-4 as a solid. MS: M+1=313.1.

1-(tert-butyl)-3-{[3-chloro-5-(3-chloro-5-cyanophenoxy)phenoxy]methyl}-1H-indazole-1-carboxylate (32-5)

In a manner identical to that described above for the synthesis of 1-2, from 75 mg (0.268 mmol) of 3-chloro-5-(3-chloro-5-hydroxyphenoxy)benzonitrile (B-4), 14 mg (0.536 mmol) of NaH 60% dispersion, and 83 mg (0.268 mmol) of 1-(tert-butyl)-3-(bromomethyl)-1H-indazole-1-carboxylate (32-4) was prepared the desired product 32-5 as a white solid. MS: M+1=510.1.

3-chloro-5-[3-chloro-5-(1H-indazol-3-ylmethoxy)phenoxy]benzonitrile (32-6)

27 mg (0.052 mmol) of 1-(tert-butyl)-3-{[3-chloro-5-(3-chloro-5-cyanophenoxy)phenoxy]methyl}-1H-indazole-1-carboxylate (32-5) was treated with a 1:1 mixture of trifluoroacetic acid and methylene chloride until an LC/MS analysis indicated that the reaction was complete. The reaction mixture was partitioned between $CH_2Cl_2$ and $H_2O$, and the organic layer was washed with a saturated sodium bicarbonate solution (3×10 mL). The organic layers were combined, dried ($MgSO_4$), filtered and concentrated in vacuo to give the desired product 32-6. MS: M+1=410.0. $^1H$ NMR ($CDCl_3$): δ 10.18 (s, 1H), 7.84 (d, 1H), 7.50 (d, 1H), 7.42 (t, 1H), 7.37 (s, 1H), 7.26 (s, 1H), 7.22 (t, 1H), 7.10 (s, 1H), 6.94 (s, 1H), 6.68 (s, 1H), 6.62 (s, 1H), 5.40 (s, 2H).

Example 33

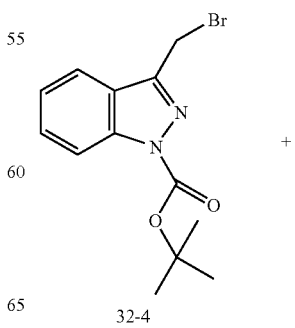

-continued

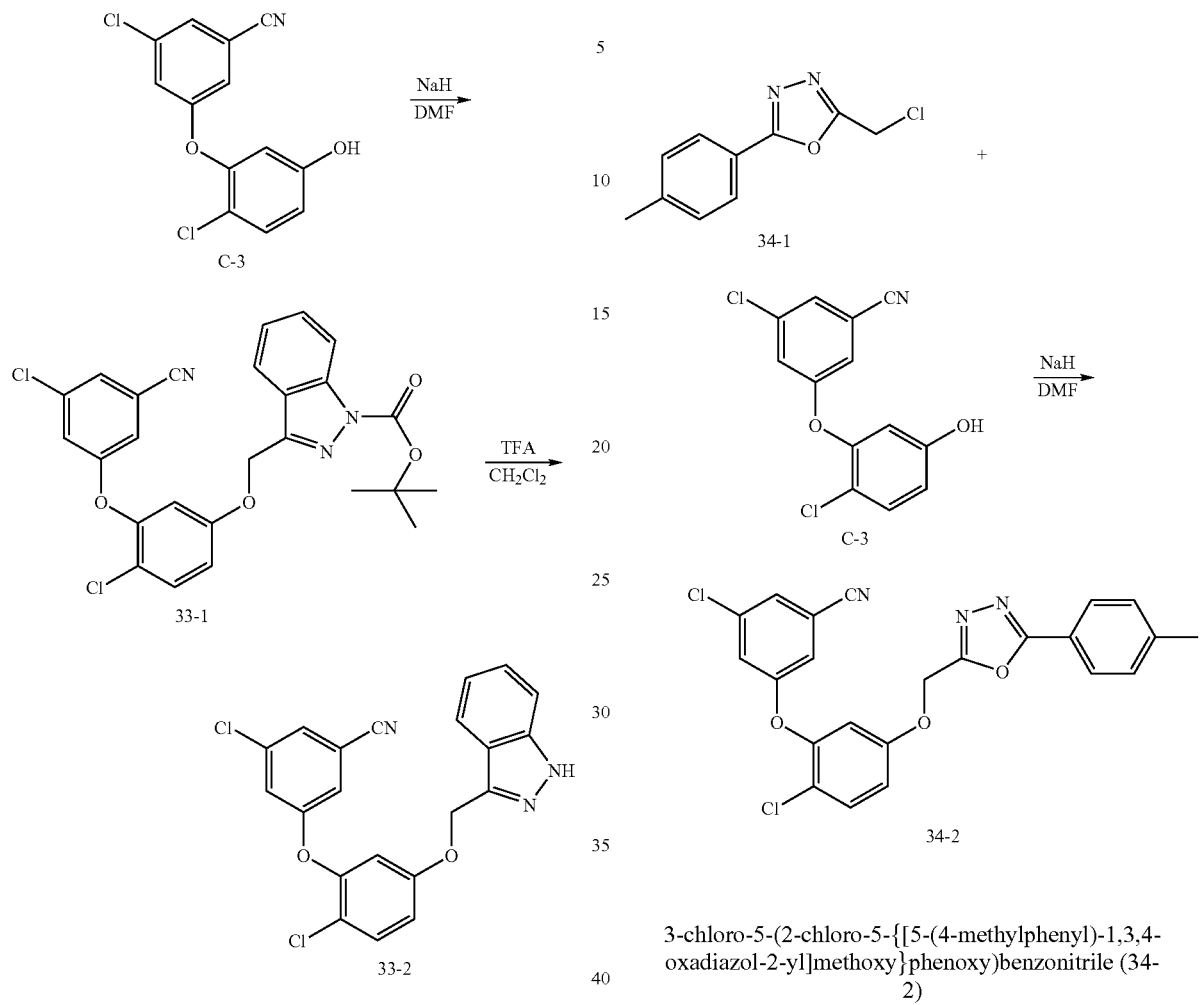

1-(tert-butyl)-3-{[4-chloro-3-(3-chloro-5-cyanophenoxy)phenoxy]methyl}-1H-indazole-1-carboxylate (33-1)

In a manner identical to that described above for the synthesis of 1-2, from 75 mg (0.268 mmol) of 3-chloro-5-(2-chloro-5-hydroxyphenoxy)benzonitrile (C-3), 14 mg (0.536 mmol) of NaH 60% dispersion, and 83 mg (0.268 mmol) of 1-(tert-butyl)-3-(bromomethyl)-1H-indazole-1-carboxylate (32-4) was prepared the desired product 33-1 as a white solid. MS: M+1=510.1.

3-chloro-5-[2-chloro-5-(1H-indazol-3-ylmethoxy)phenoxy]benzonitrile (33-2)

In a manner identical to that described above for the synthesis of 32-6, from 46 mg (0.090 mmol) of 1-(tert-butyl)-3-{[4-chloro-3-(3-chloro-5-cyanophenoxy)phenoxy]methyl}-1H-indazole-1-carboxylate was prepared the desired product 33-2 as a white solid. MS: M+1=410.1. $^1$H NMR (CDCl$_3$): δ 10.14 (s, 1H), 7.84 (d, 1H), 7.49 (d, 1H), 7.42 (t, 1H), 7.34 (s, 1H), 7.21 (t, 1H), 7.14 (s, 1H), 6.98 (s, 1H), 6.93 (dd, 2H), 6.84 (s, 1H), 5.42 (s, 2H).

Example 34

3-chloro-5-(2-chloro-5-{[5-(4-methylphenyl)-1,3,4-oxadiazol-2-yl]methoxy}phenoxy)benzonitrile (34-2)

In a manner identical to that described above for the synthesis of 1-2, from 50 mg (0.179 mmol) of 3-chloro-5-(2-chloro-5-hydroxyphenoxy)benzonitrile (C-3), 9 mg (0.357 mmol) of NaH 60% dispersion, and 37 mg (0.179 mmol) of 2-(chloromethyl)-5-(4-methylphenyl)-1,3,4-oxadiazole (34-1) was prepared the desired product 34-2 as a solid. MS: M+1=452.1. $^1$H NMR (CDCl$_3$): δ 7.60 (d, 2H), 7.44 (d, 1H), 7.34 (s, 1H), 7.32 (d, 1H), 7.14 (s, 1H), 7.04 (s, 1H), 6.97 (dd, 2H), 6.82 (s, 1H), 5.25 (s, 2H), 2.41 (s, 3H).

Example 35

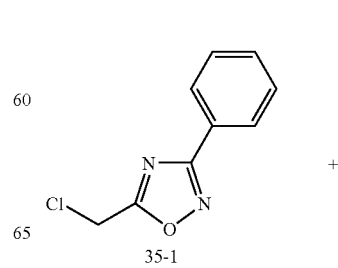

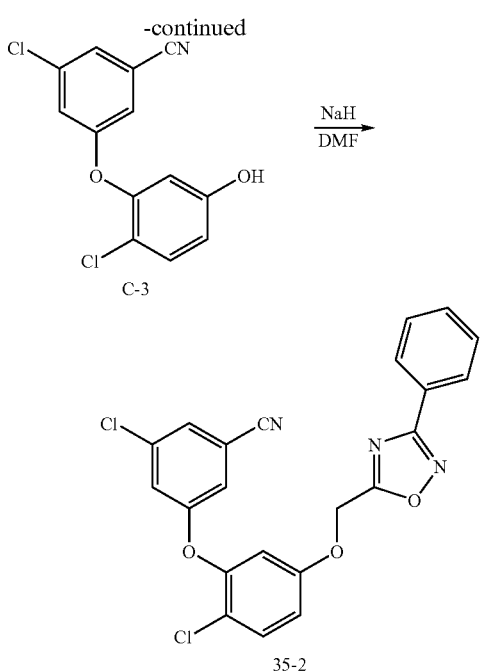

3-chloro-5-{2-chloro-5-[(3-phenyl-1,2,4-oxadiazol-5-yl)methoxy]phenoxy}benzonitrile (35-2)

In a manner identical to that described above for the synthesis of 1-2, from 50 mg (0.179 mmol) of 3-chloro-5-(2-chloro-5-hydroxyphenoxy)benzonitrile (C-3), 9 mg (0.357 mmol) of NaH 60% dispersion, and 35 mg (0.179 mmol) of 3-[5-(chloromethyl)-1,2,4-oxadiazol-3-yl]pyridine (35-1) was prepared the desired product 35-2 as a solid. MS: M+1=439.0. $^1$H NMR (CDCl$_3$): δ 8.40 (d, 2H), 7.52 (m, 2H), 7.46 (d, 1H), 7.34 (s, 1H), 7.14 (s, 1H), 7.03 (s, 1H), 6.94 (dd, 2H), 6.81 (s, 1H), 5.40 (s, 2H).

Example 36

3-chloro-5-[2-chloro-5-(1H-pyrazolo[3,4-b]pyridin-3-ylmethoxy)phenoxy]benzonitrile (36-5)

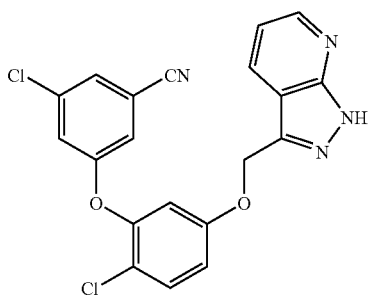

Step 1: 1-(2-fluoropyridine-3-yl)ethanone (36-1)

A solution of 3.13 mL (30.90 mmol) of freshly distilled diisopropylamine in 10 mL of anhydrous THF under nitrogen cooled to −78° C. was treated dropwise with 19.31 mL (30.90 mmol) of a 1.6 M solution of n-BuLi in hexanes. The resulting solution was stirred at −78° C. for approximately 20 minutes, and was briefly (5-10 minutes) warmed to −40° C., then recooled to −78° C. At 30 minutes post addition, 3.00 g (30.90 mmol) of 2-fluoropyridine was added dropwise to the reaction. The resulting solution was stirred at −78° C. for 30 minutes. The reaction was treated dropwise with a solution of 3.16 mL (30.90 mmol) of the Weinreb amide in 30 mL of THF. The resulting solution was stirred 18 hours, allowing the bath to slowly evaporate and the reaction temperature to rise to room temperature. The reaction was treated with 5 mL of 1N HCl, and was concentrated to remove most of the THF. The residue was extracted twice with EtOAc, and the combined extracts were washed with 1N HCl, saturated aqueous NaHCO$_3$ solution, and brine, and were dried over anhydrous MgSO$_4$. Filtration and concentration of the filtrate provided a crude orange oil, which was purified by flash chromatography over silica gel with 3:1 Hexanes/EtOAc to provide 1.10 g of the title product as an orange oil. $^1$H NMR (CDCl$_3$): 2.72 (s, 3H), 7.33 (m, 1H), 8.34 (m, 1H), 8.41 (m, 1H).

Step 2: 3-methyl-1H-pyrazolo[3,4-b]pyridine (36-2)

A stirred solution of 1.10 g (7.91 mmol) of 1-(2-fluoropyridin-3-yl)ethanone in 5 mL of ethylene glycol under nitrogen was treated with 265 μL (8.31 mmol) of hydrazine. This solution was stirred for 2 hours at room temperature and then heated at 165° C. for 1.5 hours. The solution was cooled to room temperature, poured into CH$_2$Cl$_2$ (25 mL), and extracted with H$_2$O (2×50 mL). The organic portions were combined, dried (MgSO$_4$), filtered and concentrated in vacuo to give the title product as a fluffy off-white solid. $^1$H NMR (CDCl$_3$): 2.61 (s, 3H), 7.14 (m, 1H), 8.06 (dd, 1H), 8.58 (dd, 1H), 11.18 (br s, 1H).

3-Methyl-1H-pyrazolo[3,4-b]pyridine can also be prepared by heating a solution of 1-(2-chloropyridin-3-yl)ethanone and aqueous hydrazine in 1-propanol at reflux and with stirring for a time sufficient to achieve complete or nearly complete conversion of the starting substrate (e.g., about 48 hours). Cooling water can then be added to the reaction mixture to precipitate the desired product which can be isolated by filtration.

Step 3: tert-butyl 3-methyl-1H-pyrazolo[3,4-b]pyridine-1-carboxylate (36-3)

A stirred solution of 692 mg (5.20 mmol) of 3-methyl-1H-pyrazolo[3,4-b]pyridine in 25 mL of acetonitrile under nitrogen was cooled to 0° C. in an ice bath, and was treated with 635 mg (5.20 mmol) of DMAP and 761 μL (5.46 mmol) of triethylamine. A solution of 1.36 g (6.24 mmol) of (BOC)$_2$O in 5 mL acetonitrile was then added dropwise using an addition funnel. Upon completion of addition, the ice bath was removed and the mixture was stirred for an additional 18 hours at room temperature. Solvent was removed in vacuo, and the residue was partitioned between EtOAc and H$_2$O. The organic layer was separated, dried (MgSO$_4$), filtered and concentrated in vacuo to an orange oil. This crude material was purified by flash chromatography over silica gel with 1:1 ethyl acetate/hexanes to give the title product as a clear oil. $^1$H NMR (CDCl$_3$): 1.74 (s, 9H), 2.60 (s, 3H), 7.29 (m, 1H), 8.02 (dd, 1H), 8.74 (dd, 1H).

Step 4: 1-(tert-butyl)-3-(bromomethyl)-1H-pyrazolo[3,4-b]pyridine-1-carboxylate (36-4)

A stirred solution of 934 mg (4.00 mmol) of tert-butyl 3-methyl-1H-pyrazolo[3,4-b]pyridine-1-carboxylate in 10 mL of CCl$_4$ was heated to reflux, and then a mixture of 783 mg (4.40 mmol) of NBS and 97 mg (0.40 mmol) of benzoyl peroxide was added portion-wise over 5 minutes as a solid. The resulting solution was heated at reflux for 5 hours and then allowed to cool to room temperature. The reaction mixture was filtered through a pad of Celite to remove precipitated succinimide, and the filtrate was concentrated in vacuo. The crude residue was purified by flash chromatography over silica gel with 1:2 ethyl acetate/hexanes to the title product as a solid. $^1$H NMR (CDCl$_3$): 1.76 (s, 9H), 4.78 (s, 2H), 7.35 (q, 1H), 8.24 (dd, 1H), 8.77 (dd, 1H).

Step 5: 3-chloro-5-[2-chloro-5-(1H-pyrazolo[3,4-b]pyridin-3-ylmethoxy)phenoxy]benzonitrile (36-5)

In a manner identical to that described above for the synthesis of N-[4-(aminosulfonyl)-2-chlorophenyl]-2-(3-phenoxyphenoxy)acetamide (Compound 1-2 in Example 1), from 80 mg (0.29 mmol) of 3-chloro-5-(2-chloro-5-hydroxyphenoxy)benzonitrile (C-3), 12 mg (0.30 mmol) of NaH 60% dispersion, and 91 mg (0.29 mmol) of 1-(tert-butyl)-3-(bromomethyl)-1H-pyrazolo[3,4-b]pyridine-1-carboxylate was prepared the crude Boc-protected derivative of the title product as an oil. This material was immediately dissolved in 1 mL methylene chloride/1 mL TFA, and the resulting solution stirred at room temperature overnight. The reaction was concentrated in vacuo, and the crude oil purified by reversed phase preparative LC on a Gilson apparatus to provide the title product 36-5 as an amorphous white powder after lyophilization. MS M+1=411. $^1$H NMR (DMSO-d$_6$):

5.47 (s, 2H), 7.08 (dd, 1H), 7.12 (d, 1H), 7.21 (q, 1H), 7.37 (dd, 1H), 7.45 (m, 1H), 7.56 (d, 1H), 7.80 (m, 1H), 8.30 (dd, 1H), 8.54 (dd, 1H), 13.70 (s, 1H).

Alternative Step 5

3-chloro-5-[2-chloro-5-(1H-pyrazolo[3,4-b]pyridin-3-ylmethoxy)phenoxy]benzonitrile (36-5) has also been prepared as follows:

3-chloro-5-(2-chloro-5-hydroxyphenoxy)benzonitrile (20.24 g), cesium fluoride (30.8 g), and 1-(tert-butyl)-3-(bromomethyl)-1H-pyrazolo[3,4-b]pyridine-1-carboxylate (22.5 g) were charged to a round bottom flask equipped with an overhead stirrer and a nitrogen inlet (the reaction was conducted under nitrogen), followed by addition of dimethylacetamide (60 mL) as solvent. The mixture was stirred at room temperature overnight, after which MTBE (500 mL) was added and the mixture transferred to an extractor containing K$_2$CO$_3$ (13 g) in water (300 mL). The organic phase was collected and washed with water (3×150 mL), and then collected and dried over sodium sulfate (20 g) overnight. The solvent was then switched from MTBE to THF (400 mL final volume), and sulfuric acid (10 mL) was added. After 18 hours, water (300 mL) was added and the solvent volume was reduced by concentration to 350 mL. The resulting solids were filtered and washed with water (100 mL) and the slurry washed with methanol (200 mL). The solids were placed in a round bottom flask, acetonitrile (150 mL) was added, the mixture heated to 80° C. and then cooled to room temperature overnight. The solids were filtered and washed with acetonitrile to afford the title product.

Example 37

3-{5-[(6-amino-1H-pyrazolo[3,4-b]pyridin-3-yl)methoxy]-2-chlorophenoxy}-5-chlorobenzonitrile (37-9)

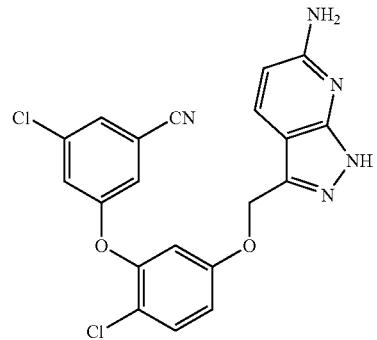

Step 1: 1-(2,6-difluoropyridin-3-yl)ethanone (37-2)

A solution of freshly distilled diisopropylamine (14.7 mL, 104.3 mmol) in 10 mL of anhydrous THF was cooled to −78° and treated with 1.6 M solution of n-BuLi in hexanes (64.0 mL, 102.5 mmol). The resulting solution naturally warmed to −20° and was maintained at −20° for 1.5 hours. The solution was cooled to −78° and 2,6 difluoro pyridine (37-1) was added dropwise. The reaction was continued with stirring for 2 hours at −78° C. before a solution of 9.7 mL (86.9 mmol) of the Weinryb amide was added in 20 mL of THF. The resulting solution was warmed to ambient temperature overnight before quenching with a brine solution. The mixture was extracted with EtOAc (3×), and the combined organic layers were washed with H$_2$O (1×), brine (2×), dried over MgSO$_4$, and concentrated in vacuo. The crude product was purified via flash silica gel chromatography (0-40% EtOAc/Hexane) to yield the desired product 37-2. $^1$H NMR (CDCl$_3$): 2.68 (s, 3H), 6.95 (d, 1H), 8.50 (q, 1H).

Step 2: 6-fluoro-3-methyl-1H-pyrazolo[3,4-b]pyridine (37-3)

To a stirred solution of 7.46 g (47.51 mmol) of 1-(2,6-difluoropyridin-3-yl)ethanone (37-2) in 50 mL of CH$_2$Cl$_2$ under nitrogen was added dropwise titanium (IV) isopropoxide. The resulting solution was stirred vigorously for 15 minutes before hydrazine hydrate (4.62 g, 95.0 mmol) was added slowly to form a thick slurry. The reaction mixture was stirred for 1 hour before the addition of 11 mL of H$_2$O, and the resulting mixture stirred for 1.5 hours until completion as determined by LC/MS analysis. The solid matter was filtered off and the filterate was condensed to yield a white solid. EtOH (100 mL) was added to the crude intermediate and the mixture was heated to reflux for 6 hours. After the reaction was complete as determined by LC/MS analysis the solvent was removed to yield the desired product. No further purification was necessary. $^1$H NMR (CDCl$_3$): 2.56 (s, 3H), 6.78 (d, 1H), 8.08 (t, 1H).

Step 3: tert-butyl 6-fluoro-3-methyl-1H-pyrazolo[3,4-b]pyridine-1-carboxylate (37-4)

A stirred solution of 6.67 g (44.2 mmol) of 6-fluoro-3-methyl-1H-pyrazolo[3,4-b]pyridine in 100 mL of acetonitrile under nitrogen was treated with 5.40 g (44.2 mmol) of DMAP and 6.46 mL (46.4 mmol) of triethylamine. A solution of 11.56 g (53.0 mmol) of (BOC)₂O in 20 mL acetonitrile was added dropwise via a cannula and the resulting reaction mixture stirred for 1 hour until completion as determined by LC/MS analysis. The reaction was quenched with brine and extracted with EtOAc (3×). The combined organic layers were washed with H₂O, brine, dried over MgSO₄, and concentrated in vacuo. The crude material was purified via silica gel chromatography (0-70% EtOAc/hexane) to yield the title compound. ¹H NMR (CDCl₃): 1.74 (s, 9H), 2.60 (s, 3H), 6.95 (d, 1H), 8.08 (t, 1H).

Step 4: tert-butyl 3-(bromomethyl)-6-fluoro-1H-pyrazolo[3,4-b]pyridine-1-carboxylate (37-5)

A stirring solution of 8.88 g (35.2 mmol) of 37-4, 6.88 g (38.7 mmol) of NBS and 851 mg (3.52 mmol) of benzoyl peroxide in 250 mL of CCl₄ was heated to reflux for 6 hours. The reaction was stopped after a 66% conversion of starting material as determined by LC/MS. The reaction mixture was cooled to room temperature, filtered through a pad of Celite to remove precipitated succinimide, and the filtrate concentrated in vacuo. The crude residue was purified by silica gel chromatography (0-70% ethyl acetate/hexanes) to afford the title product as a solid. ¹H NMR (CDCl₃): 1.75 (s, 9H), 4.75 (s, 2H), 7.00 (d, 1H), 8.30 (t, 1H).

Step 5: 3-chloro-5-{2-chloro-5-[(6-fluoro-1H-pyrazolo[3,4-b]pyridin-3-yl)methoxy]phenoxy}benzonitrile (37-7)

In a manner identical to that described above for the synthesis of 1-2, from 2.97 g (10.68 mmol) of 3-chloro-5-(2-chloro-5-hydroxyphenoxy)benzonitrile (C-3), 3.29 g (10.15 mmol) of Cs₂CO₃, and 3.34 g (10.15 mmol) of tert-butyl 3-(bromomethyl)-6-fluoro-1H-pyrazolo[3,4-b]pyridine-1-carboxylate (37-5) was prepared crude 3-chloro-5-{2-chloro-5-[(1-t-butyloxycarbonyl-6-fluoro-1H-pyrazolo[3,4-b]pyridin-3-yl)methoxy]phenoxy}benzonitrile (37-6) as an oil. This BOC-protected material (3.66 g) was immediately dissolved in 10 mL TFA, and the resulting solution stirred for 20 minutes at room temperature. The crude reaction mixture was concentrated in vacuo and purified via silica gel chromatography (10-70% EtOAc/hexane) to yield the title compound. H¹ NMR (CDCl₃): 5.47 (s, 2H), 6.85 (d, 1H), 6.95 (d, 1H), 7.02 (s, 1H), 7.10 (s, 1H), 7.30 (s, 1H), 7.40 (d, 1H), 8.38 (t, 1H), 11.38 (bs, 1H).

Step 6: 3-chloro-5-[2-chloro-5-({6-[(4-methoxybenzyl)amino]-1H-pyrazolo[3,4-b]pyridin-3-yl}methoxy)phenoxy]benzonitrile (37-8)

To a solution of 3-chloro-5-{2-chloro-5-[(6-fluoro-1H-pyrazolo[3,4-b]pyridin-3-yl)methoxy]phenoxy}benzonitrile (37-7, 200 mg, 0.467 mmol) in NMP (5 mL) was added 0.61 mL of 1-(4-methoxyphenyl)methenamine. The resulting solution was heated to 95° C. for 18 hours until completion as determined by LC/MS analysis. The reaction was cooled to room temperature and diluted with (1/1) brine/H₂O solution and extracted with EtOAc (3×). The combined organic layers were washed with H₂O (4×), brine (2×), dried over MgSO₄, and concentrated in vacuo. The crude material was purified via silica gel chromatograpy (20-100% EtOAc/hexane) to yield the title compound. ¹H NMR (CDCl₃): 3.80 (s, 3H), 4.58 (d, 2H), 4.98 (t, 1H), 5.30 (s, 2H), 6.30 (d, 1H), 6.82 (m, 1H), 6.85 (d, 1H), 6.92 (d, 1H), 7.00 (s, 1H), 7.10 (s, 1H), 7.12 (m, 1H), 7.25-7.35 (m, 3H), 7.38 (d, 1H), 7.80 (d, 1H).

Step 7: 3-{5-[(6-amino-1H-pyrazolo[3,4-b]pyridin-3-yl)methoxy]-2-chlorophenoxy}-5-chlorobenzonitrile (37-9)

3-chloro-5-[2-chloro-5-({6-[(4-methoxybenzyl)amino]-1H-pyrazolo[3,4-b]pyridin-3-yl}methoxy)phenoxy]benzonitrile (37-8) was dissolved in 6 mL of TFA and heated to 60° C. for 7 hours until reaction was complete as determined by LC/MS analysis. After removal of all volatile material the crude residue was purified via prep HPLC (20%-70% acetonitrile in H₂O: C18 Phenomenex Gemini) and lyophilzed from dioxane to yield the title compound in the form of a TFA salt. H¹ NMR (CD₃OD): 5.40 (s 2H), 6.58 (d, 1H), 6.96 (d, 1H), 7.04 (d, 1H), 7.16 (s, 1H), 7.18 (s, 1H), 7.58 (d, 1H), 7.52 (s, 1H), 8.10 (bs, 1H).

Examples 38-44

The compounds in the following table and having the following general formula:

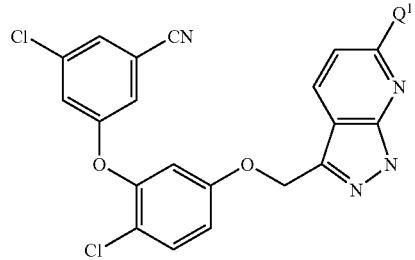

were prepared in accordance with the following procedure: To a solution of 3-chloro-5-{2-chloro-5-[(6-fluoro-1H-pyrazolo[3,4-b]pyridin-3-yl)methoxy]phenoxy}benzonitrile (1 eq) in NMP was added the appropriate amine (10 eq) and the resulting solution was heated to 95° C. until the reaction was complete as determined by LC/MS analysis. The reaction mixture was cooled to room temperature and diluted with (1/1) brine/H₂O solution and extracted with EtOAc (3×). The combined organic layers were washed with H₂O (4×), brine (2×), dried over MgSO₄, and concentrated in vacuo. The crude material was purified by column chromatography to afford the desired product.

| Ex. | Compound Name | Q¹ | M + 1 |
|---|---|---|---|
| 38 | 3-chloro-5-(2-chloro-5-{[6-methylamino)-1H-pyrazolo[3,4-b]-pyridin-3-yl]methoxy}phenoxy)benzonitrile | —NHMe | 440.3 |
| 39 | 3-chloro-5-(2-chloro-5-{[6-dimethylamino)-1H-pyrazolo[3,4-b]-pyridin-3-yl]methoxy}phenoxy)benzonitrile | —NMe₂ | 454.3 |

-continued

| Ex. | Compound Name | Q$^1$ | M + 1 |
|---|---|---|---|
| 40 | 3-chloro-5-[2-chloro-5-({6-[(2-methoxyethyl)(methyl)amino]-1H-pyrazolo[3,4-b]-pyridin-3-yl}methoxy)phenoxy)benzonitrile | —NMe(CH$_2$CH$_2$OMe) | 498.3 |
| 41 | 3-chloro-5-(2-chloro-5-[(6-morpholin-4-yl-1H-pyrazolo[3,4-b]-pyridin-3-yl)methoxy]phenoxy)benzonitrile | 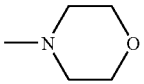 | 496.3 |
| 42 | N2-(3-{[4-chloro-3-(3-chloro-5-cyanophenoxy)phenoxy]methyl}-1H-pyrazolo[3,4-b]pyridin-6-yl)-N2-methylglycinamide | —NMe(CH$_2$C(O)NH$_2$) | 439.8 |
| 43 | 3-chloro-5-(2-chloro-5-{[6-(3-methoxyazetidin-1-yl)-1H-pyrazolo[3,4-b]-pyridin-3-yl]methoxy}phenoxy)benzonitrile |  | 495.6 |
| 44 | 3-chloro-5-(2-chloro-5-{[6-(azetidin-1-yl)-1H-pyrazolo[3,4-b]-pyridin-3-yl]methoxy}phenoxy)benzonitrile | 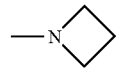 | 465.7 |

Examples 45-48

The compounds in the following table were prepared in accordance with the procedures set forth in Steps 6 and 7 of Example 37 using the appropriate amine in place of 1-(4-methoxyphenyl)methenamine. All of the compounds in the table were prepared as TFA salts after reversed phase LC purification. The compound name shown in the table is the name of the free base.

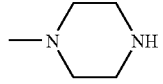

| Ex. | Compound Name | Q$^2$ | M + 1 |
|---|---|---|---|
| 45 | 3-chloro-5-{2-chloro-5-[(6-piperazin-1-yl-1H-pyrazolo[3,4-b]-pyridin-3-yl)methoxy]phenoxy}benzonitrile | 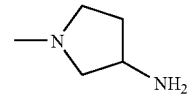 | 494.7 |
| 46 | (RS) 3-(5-{[6-(3-aminopyrrolidin-1-yl)-1H-pyrazolo[3,4-b]-pyridin-3-yl]methoxy}-2-chlorophenoxy)-5-chlorobenzonitrile | 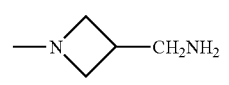 | 494.7 |
| 47 | 3-[5-({6-[3-(aminomethyl)azetidin-1-yl]-1H-pyrazolo[3,4-b]-pyridin-3-yl}methoxy)-2-chlorophenoxy]-5-chlorobenzonitrile | 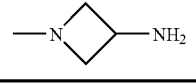 | 494.6 |
| 48 | 3-(5-{[6-(3-aminoazetidin-1-yl)-1H-pyrazolo[3,4-b]-pyridin-3-yl]methoxy}-2-chlorophenoxy)-5-chlorobenzonitrile | | 480.7 |

Example 49

3-Chloro-5-{2-chloro-5-[2-(1H-pyrazolo[3,4-b]pyridin-3-yl)ethyl]phenoxy}benzonitrile (49-9)

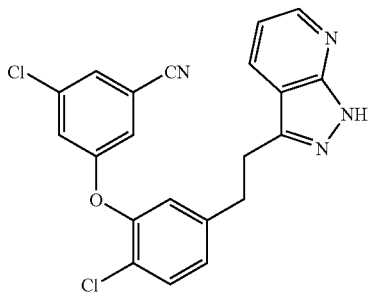

Step 1: 1H-pyrazolo[3,4-b]pyridine (49-2)

A mixture of 10.00 g (70.65 mmol) of 2-chloro-3-formylpyridine(49-1) in 225 mL of absolute ethanol/100 mL of hydrazine hydrate was heated at reflux for 24 hours. The reaction mixture was then cooled to room temperature and concentrated in vacuo to a brown oil-solid. The crude product was chromatographed over silica gel with 2.5% methanol/chloroform to give the desired product as a yellow oil that slowly crystallized to a yellow solid. $^1$H NMR (CDCl$_3$): 7.20 (m, 1H), 8.15 (m, 2H), 8.66 (dd, 1H), 12.49 (br s, 1H).

Step 2: 3-iodo-1H-pyrazolo[3,4-b]pyridine (49-3)

A solution of 1.00 g (8.40 mmol) of 1H-pyrazolo[3,4-b]pyridine in 15 mL of DMF was treated with 4.26 g (16.80 mmol) of iodine, followed by 1.77 g (31.50 mmol) of solid KOH. The resulting reddish-brown mixture was stirred at ambient temperature for 1 hour. The reaction was diluted with 5× its volume with a solution of aq. 10% NaHSO$_3$, and the mixture stirred. The yellow solid precipitate was filtered off, washed with water, and dried in vacuo to give the desired product. The crude product was used as is in the next reaction. MS M+1=246.

Step 3: tert-butyl 3-iodo-1H-pyrazolo[3,4-b]pyridine-1-carboxylate (49-4)

A magnetically stirred suspension of 1.20 g (4.90 mmol) of 3-iodo-1H-pyrazolo[3,4-b]pyridine (49-3) in 35 mL of anhydrous acetonitrile under a nitrogen atmosphere was treated with 720 µL (5.15 mmol) of triethylamine, followed by 599 mg (4.90 mmol) of 4-dimethylaminopyridine. The resulting solution was treated approximately 2 minutes later with a solution of 1.29 g (5.88 mmol) of BOC anhydride in 5 mL of anhydrous acetonitrile, and the resulting solution stirred at room temperature for 72 hours. The crude reaction mixture was partitioned between ethyl acetate and water, and the organic layer was separated, washed with brine, and dried in vacuo (anhydrous MgSO$_4$). The dried extract was filtered, and the filtrate concentrated in vacuo to give 2 g of the crude solid product. The product was purified by flash chromatography over silica gel with 20:1 hexanes/EtOAc (crude material dissolved in chloroform, impregnated on silica, and the silica applied to the top of the column) to give the desired product as a white solid. M+=245 (M−100, loss of BOC). $^1$H NMR (CDCl$_3$): 1.73 (s, 9H), 7.36 (dq, 1H), 7.84 (dd, 1H), 7.78 (dd, 1H).

Step 4: 4-chloro-3-(3-chloro-5-cyanophenoxy)phenyl trifluoromethanesulfonate (49-5)

A solution of 1.00 g (3.57 mmol) of 3-chloro-5-(2-chloro-5-hydroxyphenoxy)benzonitrile (C-3) in 10 mL of methylene chloride was cooled to −15° C. in a nitrogen atmosphere, and was treated with 747 µL (4.29 mmol) of diisopropylethylamine followed by 722 µL (4.29 mmol) of trifluoromethanesulfonic anhydride. The resulting solution was allowed to warm to room temperature, and was stirred overnight. The reaction was diluted with water, and the mixture extracted with ether. The ether layer was washed with $^1$N HCl, water, and brine, and was dried (anhydrous MgSO$_4$). The dried extract was filtered, and the filtrate concentrated in vacuo to give the desired product as a brown oil that slowly crystallized to a tan solid. $^1$H NMR (CDCl$_3$): 7.06 (d, 1H), 7.07 (m, 1H), 7.18 (m, 1H), 7.20 (dd, 1H), 7.43 (m, 1H), 7.62 (d, 1H).

Step 5: 3-chloro-5-{2-chloro-5-[(trimethylsilyl)ethynyl]phenoxy}benzonitrile(49-6)

A solution of 500 mg (1.21 mmol) of 4-chloro-3-(3-chloro-5-cyanophenoxy)phenyl trifluoromethanesulfonate (49-5), 240 mL (1.70 mmol) of trimethylsilyl-acetylene, and 43 mg (0.06 mmol) of bis(triphenylphosphino) palladium(II) chloride in 3 mL anhydrous DMF/0.75 mL triethylamine was stirred at 90° C. in a glass sealed vessel for approximately 1.5 hours. The resulting solution was concentrated to a dark oil. The crude oil was purified by flash chromatography over silica gel with 20:1 hexanes/EtOAc to give the desired product as a yellow solid. $^1$H NMR (CDCl$_3$): 0.26 (m, 9H), 7.03 (m, 1H), 7.13 (t, 1H), 7.19 (d, 1H), 7.33 (dd, 1H), 7.36 (t, 1H), 7.44 (d, 1H).

Step 6: 3-chloro-5-(2-chloro-5-ethynylphenoxy)benzonitrile (49-7)

A stirred solution of 310 mg (0.92 mmol) of 3-chloro-5-{2-chloro-5-[(trimethylsilyl)ethynyl]phenoxy}benzonitrile (49-6) in 3 mL anhydrous THF under a nitrogen atmosphere was cooled to 0° C., and was treated dropwise with 1.01 mL (1.01 mmol) of a 1M solution of tetrabutylammonium fluoride in THF. The dark solution was stirred for 1 hour, and the reaction partitioned between EtOAc and water. The EtOAc layer was washed with water and brine, was dried (anhydrous MgSO$_4$), filtered, and concentrated to give a dark oil. The crude oil was purified by flash chromatography over silica gel with 9:1 hexanes/EtOAc to provide the desired product as an off white solid. $^1$H NMR (CDCl$_3$): 3.17 (s, 1H), 7.03 (m, 1H), 7.14 (m, 1H), 7.21 (m, 1H), 7.36 (m, 2H), 7.47 (dd, 1H).

Step 7: tert-butyl-3-{[4-chloro-3-(3-chloro-5-cyanophenoxy)phenyl]ethynyl}-1H-pyrazolo[3,4-]pyridine-1-carboxylate (49-8)

A solution of 147 mg (0.51 mmol) of 3-chloro-5-(2-chloro-5-ethynylphenoxy)benzonitrile, 166 mg (0.48 mmol) of tert-butyl 3-iodo-1H-pyrazolo[3,4-b]pyridine-1-carboxylate, 17 mg (0.03 mmol) of bis(triphenylphosphino)palladium (II) chloride, and 9.00 mg (0.05 mmol) of CuI in 2.5 mL DMF/5 mL triethylamine under nitrogen was stirred at room temperature for one hour. The reaction mixture was concentrated in vacuo to a dark oil. The crude oil was purified by flash chromatography over silica gel with 2.5:1 hexanes/EtOAc to provide the desired product as a yellow oil/foam. M+=405 (M−100, loss of Boc). ¹H NMR (CDCl₃): 1.75 (s, 9H), 7.10 (m, 1H), 7.19 (m, 1H), 7.36 (m, 1H), 7.39 (m, 2H), 7.50 (dd, 1H), 7.56 (dd, 1H), 8.21 (dd, 1H), 8.82 (dd, 1H).

Step 8: 3-chloro-5-{2-chloro-5-[2-(1H-pyrazolo[3,4-b]pyridin-3-yl)ethyl]phenoxy}benzonitrile (49-9)

A solution of 250 mg (0.50 mmol) of tert-butyl-3-{[4-chloro-3-(3-chloro-5-cyanophenoxy)phenyl]ethynyl}-1H-pyrazolo[3,4-]pyridine-1-carboxylate in 10 mL of absolute EtOH was hydrogenated at 1 atm pressure (balloon) over 250 mg of 10% Pd on carbon catalyst. After approximately 24 hours, the reaction mixture was filtered through a pad of Celite, and the filtrate concentrated in vacuo to a yellow oil. The crude intermediate oil was dissolved in 1 mL TFA, and the solution stirred at room temperature for 1 hour. The reaction mixture was concentrated in vacuo to provide the crude product as a dark oil. The dark oil was purified by reversed phase preparative LC on a Gilson apparatus to give the desired product as a fluffy off-white solid. MS M+=409. ¹H NMR (CDCl₃): 3.17 (t, 2H), 3.31 (t, 2H), 6.94 (m, 2H), 7.09 (m, 2H), 7.15 (q, 1H), 7.32 (t, 1H), 7.39 (d, 1H), 7.80 (dd, 1H), 8.54 (dd, 1H), 10.5-11.5 (very br, 1H).

Example 50

3-{5-[(6-amino-1H-pyrazolo[3,4-b]pyridin-3-yl)methoxy]-2-chloro-3-fluorophenoxy}-5-chlorobenzonitrile

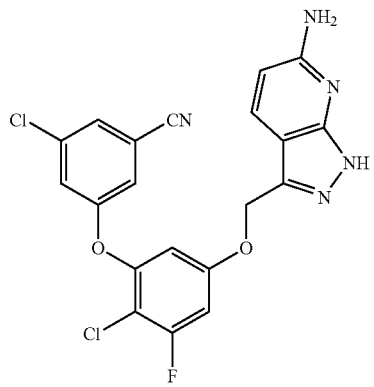

Step 1: 3-fluoro-5-methoxyphenol (50-1)

Under nitrogen atmosphere, 1-fluoro-3,5-dimethoxybenzene (25 g, 160 mmol) was diluted in CH₂Cl₂ (200 mL, 0.8M) and then cooled to −15° C. Next, BBr₃ (176 mL, 176 mmol, 1M in CH₂Cl₂) was slowly added to the reaction mixture. The reaction mixture was stirred at −15° C. for one and a half hours and at room temperature for 10 minutes. The reaction mixture was then cooled to 0° C. and slowly quenched with water (150 mL). The aqueous layer was then extracted with methylene chloride (3×100 mL). The organic extracts were dried over sodium sulfate and concentrated. Silica gel chromatography (1%-30% EtOAc/Hexanes) gave the mono demethylated product (50-1) (15 g, 67%).

Step 2: 2-chloro-3-fluoro-5-methoxyphenol (50-2)

Under a nitrogen atmosphere, 3-fluoro-5-methoxyphenol (50-1) (15 g, 106 mmol) was diluted in DCE (150 mL, 0.7 M). To this solution NCS (15.5 g, 116 mmol) was added, and the reaction mixture was heated to reflux for 4 hours. The reaction was then cooled to room temperature and quenched with water (100 mL). The aqueous layer was then extracted with methylene chloride (3×50 mL). The organic extracts were dried over sodium sulfate and concentrated. Silica gel chromatography (1%-30% EtOAc/Hexanes) gave 2-chloro-3-fluoro-5-methoxyphenol (50-2) (6.7 g, 36%) and 4-chloro-3-fluoro-5-methoxyphenol (50-3) (2.8 g, 15%). LCMS (ES) m/z 177.2 (M)⁺. The starting material, 3-fluoro-5-methoxyphenol (50-1), was also recovered (4.3 g).

Step 3: 3-chloro-5-(2-chloro-3-fluoro-5-methoxyphenoxy)benzonitrile (50-4)

Under a nitrogen atmosphere, 2-chloro-3-fluoro-5-methoxyphenol (50-2) (6.7 g, 37.9 mmol) was diluted in NMP (40 mL, 0.95 M). To this solution Cs₂CO₃ (24.73 g, 76 mmol) was added and the reaction was allowed to stir at room temperature for 5 minutes. Then, 3-chloro-5-fluorobenzonitrile (11.81 g, 76 mmol) was added to the reaction and it was then heated to 120° C. After 2 hours the reaction was cooled to room temperature and then diluted with EtOAc (40 mL). It was partitioned with water (20 mL) and then extracted with EtOAc (3×30 mL). The organic extracts were then washed with water (3×20 mL) and brine (1×20 mL), dried over sodium sulfate and concentrated. Silica gel chromatography (1%-15% EtOAc/Hexanes) gave 3-chloro-5-(2-chloro-3-fluoro-5-methoxyphenoxy)-benzonitrile (50-4) (10.4 g, 88%).

Step 4: 3-chloro-5-(2-chloro-3-fluoro-5-hydroxyphenoxy)benzonitrile (50-5)

Under nitrogen atmosphere, 3-chloro-5-(2-chloro-3-fluoro-5-methoxyphenoxy)-benzonitrile (50-4) (9.6 g, 30.8 mmol) was diluted in CH₂Cl₂ (60 mL, 0.5M) and then cooled to 0° C. To this solution BBr₃ (61.5 mL, 61.5 mmol, 1M in CH₂Cl₂) was slowly added to the reaction. The reaction mixture was allowed to slowly warm to room temperature and stir for 12 hours. It was then cooled to 0° C. and slowly quenched with water (60 mL). The aqueous layer was then extracted with methylene chloride (3×30 mL). The organic extracts were dried over sodium sulfate and concentrated. Silica gel chromatography (1%-20% EtOAc/Hexanes) gave 3-chloro-5-(2-chloro-3-fluoro-5-hydroxyphenoxy)benzonitrile (50-5) (3.2 g, 35%). LCMS (ES) m/z 298.2 (M)⁺.

Step 5: tert-butyl3-{[4-chloro-3-(3-chloro-5-cyanophenoxy)-5-fluorophenoxy]methyl}-6-fluoro-1H-pyrazolo[3,4-b]pyridine-1-carboxylate (50-6)

Under a nitrogen atmosphere, 3-chloro-5-(2-chloro-3-fluoro-5-hydroxyphenoxy)benzonitrile (50-5) (150 mg, 0.503 mmol) was dissolved in NMP (4 mL, 0.1 M). Next, Cs₂CO₃ (164 mg, 0.503 mmol) was added and the reaction was allowed to stir at room temperature for 15 minutes. Then, tert-butyl-3-(bromomethyl)-6-fluoro-1H-pyrazolo[3,4-b]pyridine-1-carboxylate (37-5) (166 mg, 0.503 mmol, prepared using the procedure set forth in Example 37) was added to the reaction. The reaction was stirred at room temperature for 2 hours. It was then diluted with EtOAc (4 mL). It was partitioned with water (3 mL) and then extracted with EtOAc (3×4 mL). The organic extracts were then washed with water (3×4 mL) and brine (1×4 mL), dried over sodium sulfate and concentrated. Silica gel chromatography (1%-20% EtOAc/Hexanes) gave tert-butyl3-{[4-chloro-3-(3-chloro-5-cyanophenoxy)-5-fluorophenoxy]-methyl}-6-fluoro-1H-pyrazolo[3,4-b]pyridine-1-carboxylate (50-6) (230 mg, 85%). LCMS (ES) m/z 446.9 (M-BOC)$^+$.

Step 6: 3-{5-[(6-amino-1H-pyrazolo[3,4-b]pyridin-3-yl)methoxy]-2-chloro-3-fluorophenoxy}-5-chlorobenzonitrile (50-7)

Under a nitrogen atmosphere, tert-butyl3-{[4-chloro-3-(3-chloro-5-cyanophenoxy)-5-fluorophenoxy]methyl}-6-fluoro-1H-pyrazolo[3,4-b]pyridine-1-carboxylate (50-6) (230 mg, 0.420 mmol) was dissolved in NMP (4 mL, 0.1 M). Next, 4-methoxybenzylamine (288 mg, 2.101 mmol) was added and the reaction was heated to 95° C. for 2 hours. It was then diluted with EtOAc (4 mL). It was partitioned with water (3 mL) and then extracted with EtOAc (3×4 mL). The organic extracts were then washed with water (3×4 mL) and brine (1×4 mL), dried over sodium sulfate and concentrated. The crude reaction material was then diluted with TFA (3 mL) and heated to 65° C. for 2 hours. It was then concentrated and purified on a reverse phase system (5%-95% AcCN/H$_2$O with 0.5% TFA) to give 3-{5-[(6-amino-1H-pyrazolo[3,4-b]pyridin-3-yl)methoxy]-2-chloro-3-fluorophenoxy}-5-chlorobenzonitrile (50-7) (8 mg, 4%). LCMS (ES) m/z 445.9 (M$^+$).

Examples 51-55

The compounds in the following table were prepared in accordance with the procedures set forth in Example 50.

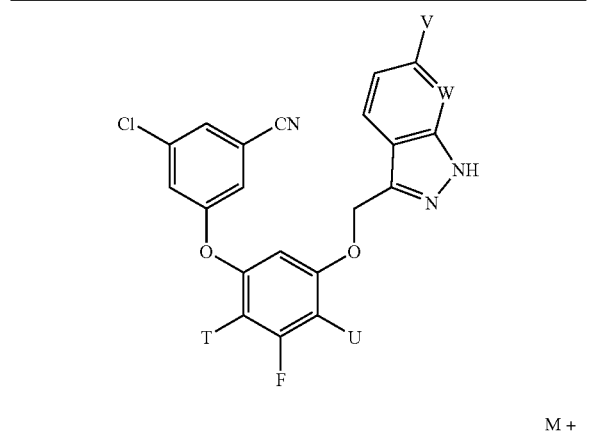

| Ex. | Compound Name | T | U | V | W | M+1 |
|---|---|---|---|---|---|---|
| 51 | 3-{5-[(1H-pyrazolo[3,4-b]pyridin-3-yl)methoxy]-3-fluorophenoxy}-5-chlorobenzonitrile | H | H | H | N | 395.1 |
| 52 | 3-{5-[(1H-pyrazolo[3,4-b]pyridin-3-yl)methoxy]-2-chloro-3-fluorophenoxy}-5-chlorobenzonitrile | Cl | H | H | N | 429.6 |
| 53 | 3-{5-[(1H-pyrazolo[3,4-b]pyridin-3-yl)methoxy]-4-chloro-3-fluorophenoxy}-5-chlorobenzonitrile | H | Cl | H | N | 429.0 |

-continued

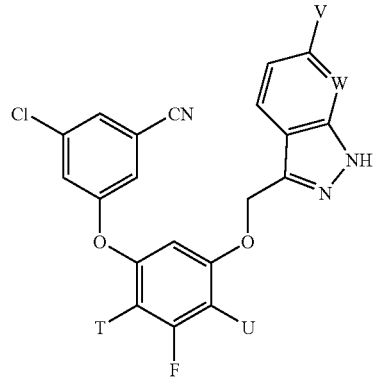

| Ex. | Compound Name | T | U | V | W | M+1 |
|---|---|---|---|---|---|---|
| 54 | 3-{5-[(7-oxo-1H-pyrazolo[3,4-b]pyridin-3-yl)methoxy]-4-chloro-3-fluorophenoxy}-5-chlorobenzonitrile | H | Cl | H | N$^+$—O$^-$ | 445.5 |
| 55 | 3-{5-[(6-amino-1H-pyrazolo[3,4-b]pyridin-3-yl)methoxy]-3-fluorophenoxy}-5-chlorobenzonitrile | H | H | NH$_2$ | N | 410.0 |

Example 56

Assay for Inhibition of HIV Reverse Transcriptase

Assays to determine the in vitro inhibition of HIV reverse transcriptase by compounds of the present invention were conducted as follows: HIV-1 RT enzyme (1 nM) was combined with inhibitor or DMSO (5%) in assay buffer (50 mM Tris-HCl, pH 7.8, 1 mM dithiothreitol, 6 mM MgCl$_2$, 80 mM KCl, 0.2% polyethylene glycol 8000, 0.1 mM EGTA), and the mixture preincubated for 30 minutes at room temperature in microtiter Optiplates (Packard). 100 μL reaction mixtures were initiated with a combination of primer-template substrate (10 nM final concentration) and dNTPs (0.6 μM dNTPs, 0.75 μM [$^3$H]-dGTP). The heterodimeric nucleic acid substrate was generated by annealing the DNA primer pD500 (described in Shaw-Reid et al., *J. Biol. Chem.*, 278: 2777-2780; obtained from Integrated DNA Technologies) to t500, a 500 nucleotide RNA template created by in vitro transcription (see Shaw-Reid et al., *J. Biol. Chem.*, 278: 2777-2780). After 1 hour incubation at 37° C., reactions were quenched by 10 μL streptavidin scintillation proximity assay beads (10 mg/mL, from Amersham Biosciences) in 0.5 M EDTA, pH 8. Microtiter plates were incubated an additional 10 minutes at 37° C. prior to quantification via Topcount (Packard). Representative compounds of the present invention exhibit inhibition of the reverse transcriptase enzyme in this assay. For example, the title compounds set forth above in Examples 1 to 55 were tested in the assay and all were found to have IC$_{50}$'s less than 20 micromolar.

Example 57

Assay for Inhibition of HIV Replication

Assays for the inhibition of acute HIV infection of T-lymphoid cells (also referred to as the "spread assay") were conducted in accordance with Vacca, J. P. et al., *Proc. Natl.*

Acad. Sci. USA 1994, 91: 4096. Representative compounds of the present invention exhibit inhibition of HIV replication in this assay. For example, the compounds set forth in Examples 1 to 55 were found to have $IC_{95}$'s of less than 20 micromolar in the assay.

Example 58

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention that were tested in the spread assay (see Example 57) were examined for cytotoxicity. For those compounds for which an $IC_{95}$ value was determined in the spread assay, no cytotoxicity was exhibited at the $IC_{95}$ concentration; i.e., their toxicity value is greater than their $IC_{95}$ value. In particular, the compounds set forth in Examples 1-55 exhibited no cytotoxicity at their $IC_{95}$ concentrations.

Example 59

2-[[(3-{[4-chloro-3-(3-chloro-5-cyanophenoxy)phenoxy]methyl}-1H-pyrazolo[3,4-b]pyridin-1-yl)carbonyl](methyl)amino]-N-methylethanaminium chloride

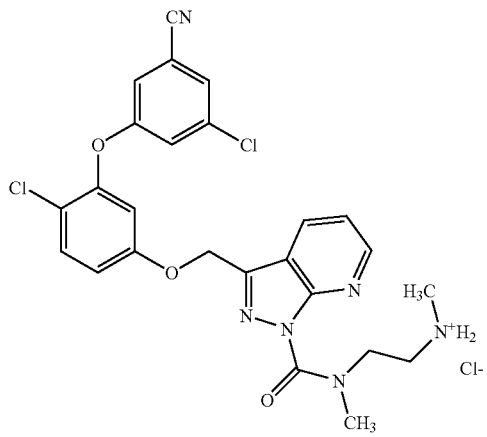

Step A: tert-Butyl 2-[[(3-{[4-chloro-3-(3-chloro-5-cyanophenoxy)phenoxy]methyl}-1H-pyrazolo[3,4-b]pyridin-1-yl)carbonyl](methyl)amino]ethyl(methyl)carbamate To a solution of triphosgene (63 mg, 0.212 mmol) in $CH_2Cl_2$ (3 mL) at 0° C. was added a mixture of Hunig's base (0.305 mL, 1.75 mmol) and tert-butyl methyl[2-(methylamino)ethyl]carbamate (100 mg, 0.531 mmol) in $CH_2Cl_2$ (2 mL) was added over 2 mins. Five minutes after the addition was complete, the reaction was allowed to warn to room temperature. The 3-chloro-5-[2-chloro-5-(1H-pyrazolo[3,4-b]pyridin-3-ylmethoxy)phenoxy]benzonitrile ((218 mg, 0.531 mmol) and then pyridine (0.141 mL 1.75 mmol) were added at room temperature and the resulting slurry heated at 70° C. in a sealed tube. A pale yellow solution was obtained which was heated at 70° C. for 16 hours. The reaction mixture was cooled to room temperature and the solvents evaporated in vacuo. The residue was dissolved in DMF (4 mL) and purified by reverse phase HPLC using a gradient elution 5 to 95% acetonitrile in water containing 0.1% trifluoroacetic acid. The pure fractions were lyophilized to afford the title compound as a cream solid. MH+-BOC 524. $^1$H NMR (400 MHz) $CDCl_3$ 8.70 (1H, dd, j-4.7 and 1.5 Hz), 8.25 (1H, dd, J=1.4, 8.1 Hz), 7.42 (1H, d, J=8.9 Hz), 7.34 (1H, t, J=1.5 Hz), 7.3291H, dd, J=8.0 and 4.7 Hz), 7.14 (1H, t, J=2 Hz), 7.01 (1H, m), 6.95 (1H, dd, J=8.9 and 2.9 Hz), 6.80 (1H, d, J=2.9 Hz), 3.80-2.60 (10H, m), 1.60-1.30 (9H, m).

Step B: 2-[[(3-{[4-chloro-3-(3-chloro-5-cyanophenoxy)phenoxy]methyl}-1H-pyrazolo[3,4-b]pyridin-1-yl)carbonyl](methyl)amino]-N-methylethanaminium chloride To a solution of the Boc derivative (see Step A; 39 mg, 0.062 mmol) in $CDCl_3$ (0.8 mL) at 0° C. was added 4M HCl in dioxane (3.1 mL 0.124 mmol). The reaction mixture was stirred for 2 hours at room temperature and the solvent evaporated in vacuo. The residue was dissolved in acetonitrile (5 mL) and lyophilized to afford the title compound as a white solid. MH+525. $^1$H NMR (400 MHz) d6 DMSO 8.67 (1H d, J=4.5 and 1.0 Hz), 8.57 (2H, brs), 8.42 (1H, dd, J=1.2 and 8.0 Hz), 7.79 (1H, s), 7.56 (1H, d, J=8.9 Hz), 7.43 (1H, s), 7.41 (1H, m), 7.37 (1H, t, J=1.8 Hz), 7.15-7.05 (2H, m), 5.52 (2H, s), 3.80-3.20 (4H, m), 3.03 (3H, brs), 2.60 (3H, brs) ppm.

Oral dosing of the title compound of Example 59 to rats has been found to provide substantially higher bioavailability as compared to that obtained via analogous dosing of the compound of Example 36.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or a pharmaceutically acceptable salt thereof:

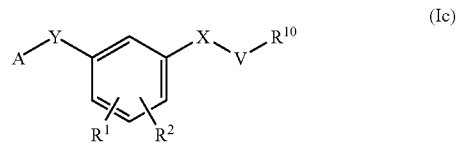

(Ic)

wherein:
$R^1$ and $R^2$ are independently selected from the group consisting of
a) H,
b) $C_{1-6}$ alkyl,
c) $C_{3-6}$ cycloalkyl,
d) $C_{1-3}$ fluoroalkyl,
e) $NO_2$,
f) halogen,
g) $OR^3$,
h) $O(CH_2)_SOR^3$,
i) $CO_2R^3$,
j) $(CO)NR^3R^4$, k) $O(CO)NR^3R^4$,
l) $N(R^3)(CO)NR^3R^4$,
m) $N(R^3)(CO)R^4$,
n) $N(R^3)(CO)OR^3$,
o) $SO_2NR^3R^4$,
p) $N(R^3)SO_2R^4$,
q) $S(O)_mR^3$,
r) CN,
s) $NR^3R^4$,
t) $N(R^3)(CO)NR^3R^4$, and
u) $O(CO)R^3$;

A is phenyl;
V is —$C(R^5R^6)$—;
X is —O—;
Y is —O—;
$R^5$ and $R^6$ are independently selected from the group consisting of hydrogen, $C_{1-6}$ alkyl, $C_{1-3}$ fluoroalkyl, and $OR^3$;
$R^{10}$ is a heterocyclyl selected from the group consisting of:

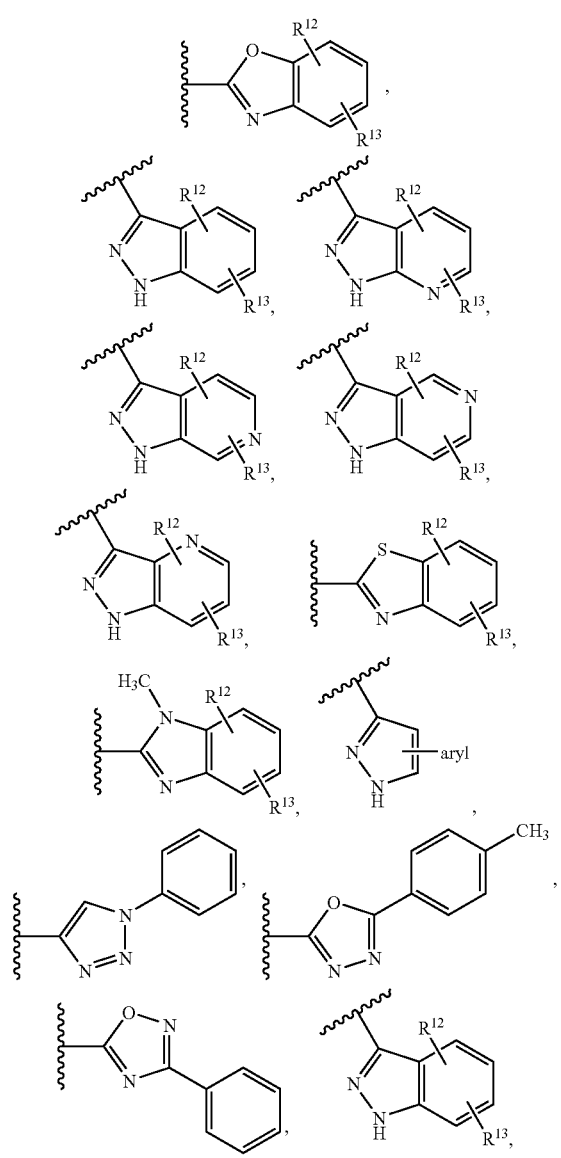

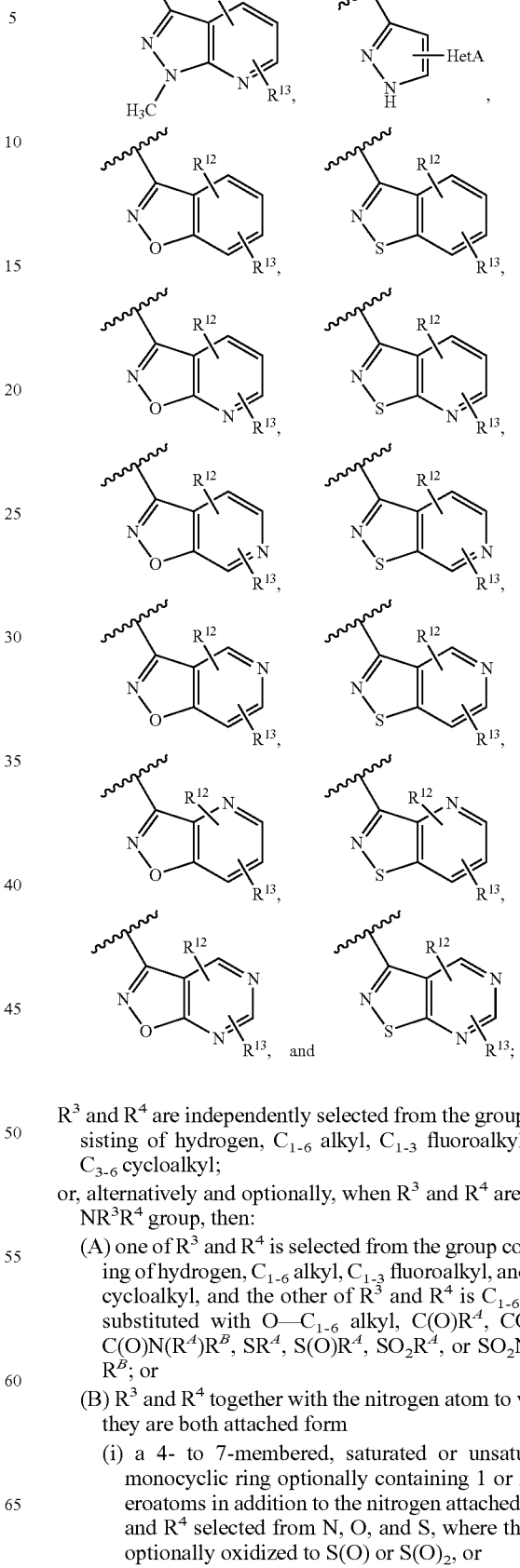

$R^3$ and $R^4$ are independently selected from the group consisting of hydrogen, $C_{1-6}$ alkyl, $C_{1-3}$ fluoroalkyl, and $C_{3-6}$ cycloalkyl;
or, alternatively and optionally, when $R^3$ and $R^4$ are in an $NR^3R^4$ group, then:
(A) one of $R^3$ and $R^4$ is selected from the group consisting of hydrogen, $C_{1-6}$ alkyl, $C_{1-3}$ fluoroalkyl, and $C_{3-6}$ cycloalkyl, and the other of $R^3$ and $R^4$ is $C_{1-6}$ alkyl substituted with O—$C_{1-6}$ alkyl, $C(O)R^A$, $CO_2R^A$, $C(O)N(R^A)R^B$, $SR^A$, $S(O)R^A$, $SO_2R^A$, or $SO_2N(R^A)R^B$; or
(B) $R^3$ and $R^4$ together with the nitrogen atom to which they are both attached form
(i) a 4- to 7-membered, saturated or unsaturated monocyclic ring optionally containing 1 or 2 heteroatoms in addition to the nitrogen attached to $R^3$ and $R^4$ selected from N, O, and S, where the S is optionally oxidized to S(O) or $S(O)_2$, or (ii) a 7- to 12-membered bicyclic ring system wherein each ring in (ii) is independent of, fused to, or bridged with the other ring and each ring is saturated or unsaturated, and wherein the bicyclic ring system optionally contains from 1 to 3 heteroatoms in addition to the nitrogen attached to $R^3$ and $R^4$ selected from N, O, and S, where the S is optionally oxidized to S(O) or S(O)$_2$, and wherein the monocyclic ring or the bicyclic ring system is optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, SO$_2$R$^A$, or SO$_2$N(R$^A$)R$^B$, (4) O—$C_{1-6}$ alkyl, (5) O—$C_{1-6}$ haloalkyl, (6) OH, (7) oxo, (8) halogen, (9) CN, (10) NO$_2$, (11) N(R$^A$)R$^B$, (12) C(O)N(R$^A$)R$^B$, (13) C(O)R$^A$, (14) C(O)—$C_{1-6}$ haloalkyl, (15) C(O)OR$^A$, (16) OC(O)N(R$^A$)R$^B$, (17) SR$^A$, (18) S(O)R$^A$, (19) S(O)$_2$R$^A$, (20) S(O)$_2$N(R$^A$)R$^B$, (21) N(R$^A$)COR$^B$, or (22) N(R$^A$)SO$_2$R$^B$ and wherein each $R^A$ is independently H or $C_{1-6}$ alkyl, and each $R^B$ is independently H or $C_{1-6}$ alkyl;

$R^{12}$ and $R^{13}$ are independently selected from the group consisting of hydrogen, halogen, oxo, NO$_2$, CN, OR$^3$, O(CH$_2$)$_t$CF$_3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, $C_{1-6}$ alkyl, $C_{1-3}$ fluoroalkyl, $C_{3-6}$ cycloalkyl, and NR$^3$R$^4$;

HetA is heteroaryl selected from the group consisting of pyridinyl, pyrimidinyl, and pyrazinyl;

s is 1-5;

t is 2-3;

v is 1-2; and m, in each instance in which it appears, is independently selected from 0-2.

2. A compound of claim 1, or a pharmaceutically acceptable salt thereof, which is a compound of Formula Ic-1:

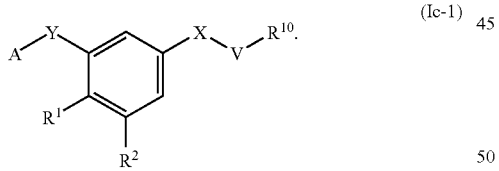
(Ic-1)

3. A compound of claim 2, or a pharmaceutically acceptable salt thereof, wherein:

$R^1$ and $R^2$ are independently selected from the group consisting of hydrogen, halogen, and $C_{1-6}$ alkyl;

$R^5$ and $R^6$ are independently selected from the group consisting of hydrogen and $C_{1-6}$ alkyl;

$R^{10}$ is selected from the group consisting of:

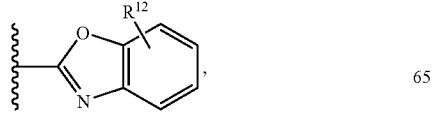

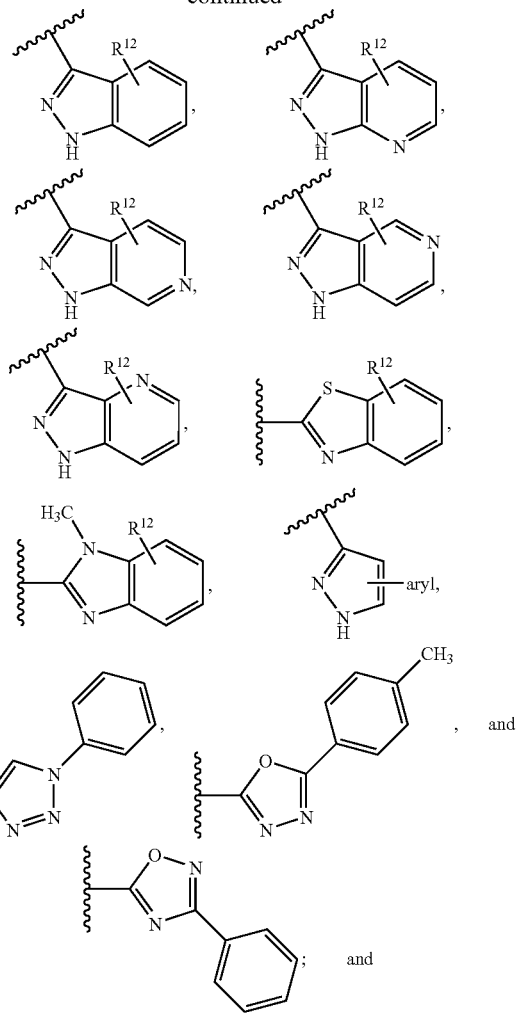

$R^{12}$ and $R^{13}$ are independently selected from the group consisting of hydrogen, halogen, oxo, NO$_2$, CN, OR$^3$, O(CH$_2$)$_t$CF$_3$, CO$_2$R$^3$, CONR$^3$R$^4$, O(CH$_2$)$_t$NR$^3$R$^4$, O(CH$_2$)$_v$COR$^3$, S(O)$_m$R$^3$, SO$_2$NR$^3$R$^4$, $C_{1-6}$ alkyl and $C_{1-3}$ fluoroalkyl.

4. A compound of claim 2, or a pharmaceutically acceptable salt thereof, wherein:

V is —CH$_2$—; and $R^{10}$ is selected from the group consisting of

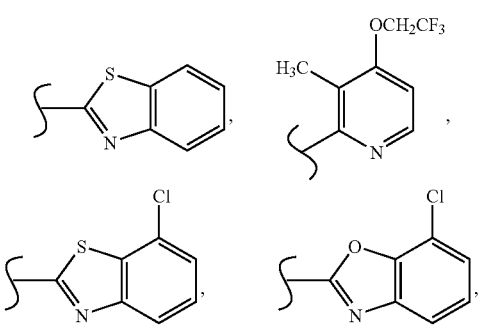

-continued

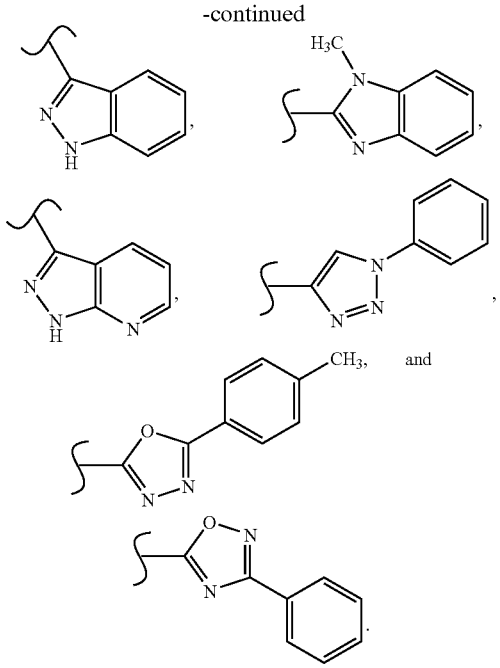

5. A compound of claim 1, or a pharmaceutically acceptable salt thereof, which is a compound of Formula Ic-2;

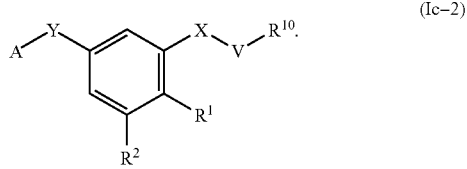

(Ic-2)

6. A compound of claim 1, or a pharmaceutically acceptable salt thereof, selected from the group consisting of:

3-[3-(1,3-benzothiazol-2-ylmethoxy)-5-chlorophenoxy]-5-chlorobenzonitrile,

3-[3-(1,3-benzothiazol-2-ylmethoxy)-5-methylphenoxy]-5-chlorobenzonitrile,

3-[5-(1,3-benzothiazol-2-ylmethoxy)-2-chlorophenoxy]-5-chlorobenzonitrile, 3-chloro-5-{3-chloro-5-[(7-chloro-1,3-benzothiazol-2-yl)methoxy]phenoxy}benzonitrile, 3-chloro-5-{2-chloro-5-[(7-chloro-1,3-benzothiazol-2-yl)methoxy]phenoxy}benzonitrile, 3-chloro-5-{2-chloro-5-[(7-chloro-1,3-benzoxazol-2-yl)methoxy]phenoxy}benzonitrile, 3-chloro-5-[3-chloro-5-(1H-indazol-3-ylmethoxy)phenoxy]benzonitrile, 3-chloro-5-{2-chloro-5-[(1-methyl-1H-benzimidazol-2-yl)methoxy]phenoxy}benzonitrile, 3-chloro-5-{2-chloro-5-[(1-phenyl-1H-1,2,3-triazol-4-yl)methoxy]phenoxy}benzonitrile, 3-chloro-5-[2-chloro-5-(1H-indazol-3-ylmethoxy)phenoxy]benzonitrile, 3-chloro-5-{2-chloro-5-[(3-phenyl-1,2,4-oxadiazol-5-yl)methoxy]phenoxy}benzonitrile, 3-chloro-5-(3-chloro-5-{([3-methyl-4-(2,2,2-trifluoroethoxy)pyridin-2-yl]methoxy}phenoxy)-benzonitrile, 3-chloro-5-(2-chloro-5-{[5-(4-methylphenyl)-1,3,4-oxadiazol-2-yl]methoxy}phenoxy)-benzonitrile, and 3-chloro-5-[2-chloro-5-(1H-pyrazolo[3,4-b]pyridin-3-ylmethoxy)phenoxy]benzonitrile, 3-{5-[(1H-pyrazolo[3,4-b]pyridin-3-yl)methoxy]-3-fluorophenoxy}-5-chlorobenzonitrile, 3-{5-[(1H-pyrazolo[3,4-b]pyridin-3-yl)methoxy]-2-chloro-3-fluorophenoxy}-5-chlorobenzonitrile, 3-{5-[(1H-pyrazolo[3,4-b]pyridin-3-yl)methoxy]-4-chloro-3-fluorophenoxy}-5-chlorobenzonitrile, and 3-{5-[(7-oxo-1H-pyrazolo[3,4-b]pyridin-3-yl)methoxy]-4-chloro-3-fluorophenoxy}-5-chlorobenzonitrile.

7. A compound of claim 1, or a pharmaceutically acceptable salt thereof, wherein:

$R^1$ and $R^2$ are each independently selected from the group consisting of hydrogen, halogen, and $C_{1-4}$ alkyl;

A is phenyl optionally substituted with from 1 to 3 substituents each of which is independently halogen, $C_{1-4}$ alkyl, or CN;

V is —CH$_2$—;

$R^{10}$ is one of $R^3$ and $R^4$ is H, $C_{1-4}$ alkyl, or $C_{3-6}$ cycloalkyl, and the other of $R^3$ and $R^4$ is H, $C_{1-4}$ alkyl, or $C_{1-4}$ alkyl substituted with O—$C_{1-4}$ alkyl, C(O)$R^A$, CO$_2R^A$, C(O)N($R^A$)$R^B$, or SO$_2R^A$;

or alternatively $R^3$ and $R^4$ together with the nitrogen atom to which they are both attached form a 4- to 7-membered, saturated monocyclic ring optionally containing 1 heteroatom in addition to the nitrogen attached to $R^3$ and $R^4$ selected from N, O, and S, where the S is optionally oxidized to S(O) or S(O)$_2$, wherein the monocyclic ring is optionally substituted with 1 or 2 substituents each of which is independently: (1) $C_{1-4}$ alkyl, (2) CF$_3$, (3) (CH$_2$)$_{1-2}$T wherein T is OH, O—$C_{1-4}$ alkyl, OCF$_3$, N($R^A$)$R^B$, C(O)N($R^A$)$R^B$, C(O)$R^A$, CO$_2R^A$, or SO$_2R^A$, (4) O—$C_{1-4}$ alkyl, (5) OCF$_3$, (6) OH, (7) oxo, (8) halogen, (9) C(O)N($R^A$)$R^B$, (10) C(O)$R^A$, (11) C(O)—CF$_3$, (12) C(O)O$R^A$, or (13) S(O)$_2R^A$;

each $R^A$ is independently H or $C_{1-4}$ alkyl, and each $R^B$ is independently H or $C_{1-4}$ alkyl.

8. A compound of claim 7, or a pharmaceutically acceptable salt thereof, which is a compound of Formula Ic-1.

9. A compound of claim 7, or a pharmaceutically acceptable salt thereof, selected from the group consisting of:

3-{5-[(6-amino-1H-pyrazolo[3,4-b]pyridin-3-yl)methoxy]-2-chlorophenoxy}-5-chlorobenzonitrile, 3-chloro-5-(2-chloro-5-{[6-methylamino)-1H-pyrazolo[3,4-b]-pyridin-3-yl]methoxy}phenoxy)-benzonitrile, 3-chloro-5-(2-chloro-5-{[6-dimethylamino)-1H-pyrazolo[3,4-b]-pyridin-3-yl]methoxy}phenoxy)-benzonitrile, 3-chloro-5-[2-chloro-5-({6-[(2-methoxyethyl)(methyl)amino]-1H-pyrazolo[3,4-b]-pyridin-3-yl}methoxy)phenoxy)benzonitrile, 3-chloro-5-(2-chloro-5-[(6-morpholin-4-yl-1H-pyrazolo[3,4-b]-pyridin-3-yl)methoxy]phenoxy)-benzonitrile, N2-(3-{[4-chloro-3-(3-chloro-5-cyanophenoxy)phenoxy]methyl}-1H-pyrazolo[3,4-b]pyridin-6-yl)-N2-methylglycinamide, 3-chloro-5-(2-chloro-5-{[6-(3-methoxyazetidin-1-yl)-1H-pyrazolo[3,4-b]-pyridin-3-yl]methoxy}phenoxy)-benzonitrile,
3-chloro-5-(2-chloro-5-{[6-(azetidin-1-yl)-1H-pyrazolo[3,4-b]-pyridin-3-yl]methoxy}phenoxy)-benzonitrile,
3-chloro-5-{2-chloro-5-[(6-piperazin-1-yl-1H-pyrazolo[3,4-b]-pyridin-3-yl)methoxy]phenoxy}-benzonitrile,
3-(5-{[6-(3-aminopyrrolidin-1-yl)-1H-pyrazolo[3,4-b]-pyridin-3-yl]methoxy}-2-chlorophenoxy)-5-chlorobenzonitrile,
3-[5-({6-[3-(aminomethyl)azetidin-1-yl]-1H-pyrazolo[3,4-b]-pyridin-3-yl}methoxy)-2-chlorophenoxy]-5-chlorobenzonitrile, and
3-(5-{[6-(3-aminoazetidin-1-yl)-1H-pyrazolo[3,4-b]-pyridin-3-yl]methoxy}-2-chlorophenoxy)-5-chlorobenzonitrile,
3-{5-[(6-amino-1H-pyrazolo[3,4-b]pyridin-3-yl)methoxy]-2-chloro-3-fluorophenoxy}-5-chlorobenzonitrile,
3-{5-[(6-amino-1H-pyrazolo[3,4-b]pyridin-3-yl)methoxy]-3-fluorophenoxy}-5-chlorobenzonitrile, and
3-{5-[(6-amino-1H-pyrazolo[3,4-b]pyridin-3-yl)methoxy]-4-chloro-3-fluorophenoxy}-5-chlorobenzonitrile.

10. A compound of Formula I-P:

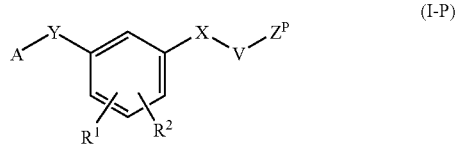

wherein:
$R^1$ and $R^2$ are independently selected from the group consisting of
a) H,
b) $C_{1-6}$ alkyl,
c) $C_{3-6}$ cycloalkyl,
d) $C_{1-3}$ fluoroalkyl,
e) $NO_2$,
f) halogen,
g) $OR^3$,
h) $O(CH_2)_s OR^3$,
i) $CO_2 R^3$,
j) $(CO)NR^3 R^4$,
k) $O(CO)NR^3 R^4$,
l) $N(R^3)(CO)NR^3 R^4$,
m) $N(R^3)(CO)R^4$,
n) $N(R^3)(CO)OR^3$,
o) $SO_2 NR^3 R^4$,
p) $N(R^3)SO_2 R^4$,
q) $S(O)_m R^3$,
r) CN,
s) $NR^3 R^4$,
t) $N(R^3)(CO)NR^3 R^4$, and
u) $O(CO)R^3$;
A is phenyl;
V is —$C(R^5 R^6)$—;
X is —O—;
Y is —O—;
$Z^P$ is $R^{10}*$;
$R^5$ and $R^6$ are independently selected from the group consisting of hydrogen, $C_{1-6}$ alkyl, $C_{1-3}$ fluoroalkyl, and $OR^3$;

$R^{10}*$ is a heterocycle selected from the group consisting of:

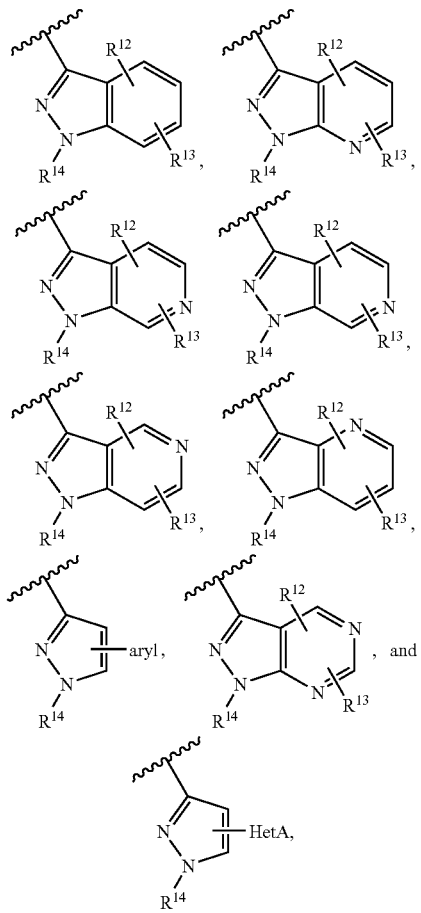

$R^{12}$ and $R^{13}$ are independently selected from the group consisting of hydrogen, halogen, oxo, $NO_2$, CN, $OR^3$, $O(CH_2)_t CF_3$, $CO_2 R^3$, $CONR^3 R^4$, $O(CH_2)_t NR^3 R^4$, $O(CH_2)_v COR^3$, $S(O)_m R^3$, $SO_2 NR^3 R^4$, $C_{1-6}$ alkyl, $C_{1-3}$ fluoroalkyl, $C_{3-6}$ cycloalkyl, and $NR^3 R^4$;
$R^3$ and $R^4$ are independently selected from the group consisting of hydrogen, $C_{1-6}$ alkyl, $C_{1-3}$ fluoroalkyl, and $C_{3-6}$ cycloalkyl;
or, alternatively and optionally, when $R^3$ and $R^4$ are in an $NR^3 R^4$ group, then:
(A) one of $R^3$ and $R^4$ is selected from the group consisting of hydrogen, $C_{1-6}$ alkyl, $C_{1-3}$ fluoroalkyl, and $C_{3-6}$ cycloalkyl, and the other of $R^3$ and $R^4$ is $C_{1-6}$ alkyl substituted with O—$C_{1-6}$ alkyl, $C(O)R^A$, $CO_2 R^A$, $C(O)N(R^A)R^B$, $SR^A$, $S(O)R^A$, $SO_2 R^A$, or $SO_2 N(R^A)R^B$; or
(B) $R^3$ and $R^4$ together with the nitrogen atom to which they are both attached form
(i) a 4- to 7-membered, saturated or unsaturated monocyclic ring optionally containing 1 or 2 heteroatoms in addition to the nitrogen attached to $R^3$ and $R^4$ selected from N, O, and S, where the S is optionally oxidized to S(O) or $S(O)_2$, or
(ii) a 7- to 12-membered bicyclic ring system wherein each ring in (ii) is independent of, fused to, or bridged with the other ring and each ring is saturated or unsaturated, and wherein the bicyclic ring system optionally contains from 1 to 3 heteroatoms in addition to the nitrogen attached to $R^3$ and $R^4$ selected from N, O, and S, where the S is optionally oxidized to S(O) or S(O)$_2$, and wherein the monocyclic ring or the bicyclic ring system is optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, NO$_2$, N($R^A$)$R^B$, C(O)N($R^A$)$R^B$, C(O)$R^A$, CO$_2R^A$, $SR^A$, S(O)$R^A$, SO$_2R^A$, or SO$_2$N($R^A$)$R^B$, (4) O—$C_{1-6}$ alkyl, (5) O—$C_{1-6}$ haloalkyl, (6) OH, (7) oxo, (8) halogen, (9) CN, (10) NO$_2$, (11) N($R^A$)$R^B$, (12) C(O)N($R^A$)$R^B$, (13) C(O)$R^A$, (14) C(O)—$C_{1-6}$ haloalkyl, (15) C(O)O$R^A$, (16) OC(O)N($R^A$)$R^B$, (17) $SR^A$, (18) S(O)$R^A$, (19) S(O)$_2R^A$, (20) S(O)$_2$N($R^A$)$R^B$, (21) N($R^A$)CO$R^B$, or (22) N($R^A$)SO$_2R^B$ and wherein each $R^A$ is independently H or $C_{1-6}$ alkyl, and each $R^B$ is independently H or $C_{1-6}$ alkyl;

HetA is heteroaryl selected from the group consisting of pyridinyl, pyrimidinyl, and pyrazinyl;

$R^{14}$ is PO(OH)O$^-$.M$^+$; PO(O$^-$)$_2$.2M$^+$; PO(O$^-$)$_2$.M$^{+2}$; or an acid salt of:

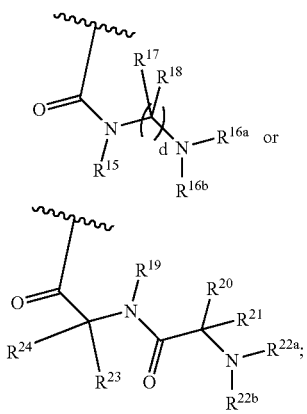

M$^+$ is a pharmaceutically acceptable monovalent counterion;

M$^{+2}$ is a pharmaceutically acceptable divalent counterion;

$R^{15}$ is H, $C_{1-6}$ alkyl, (CH$_2$)$_{2-3}$CF$_3$, AryA, or HetB;

$R^{16a}$ and $R^{16b}$ are each independently H, $C_{1-6}$ alkyl, (CH$_2$)$_{2-3}$CF$_3$, AryA, or HetB;

each $R^{17}$ is independently H or $C_{1-6}$ alkyl;

each $R^{18}$ is independently H or $C_{1-6}$ alkyl;

alternatively, $R^{15}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{15}$ is attached, wherein the optional heteroatom is selected from N, O and S, where the S is optionally oxidized to S(O) or S(O)$_2$;

alternatively, $R^{16a}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{16a}$ is attached, wherein the optional heteroatom is selected from N, O and S, where the S is optionally oxidized to S(O) or S(O)$_2$;

alternatively, an $R^{17}$ together with the $R^{18}$ attached to the same carbon atom form a 5- or 6-membered, saturated monocyclic ring optionally containing a heteroatom, wherein the optional heteroatom is selected from N, O and S, where the S is optionally oxidized to S(O) or S(O)$_2$;

$R^{19}$ is H or $C_{1-6}$ alkyl;

$R^{20}$ is H or $C_{1-6}$ alkyl;

$R^{21}$ is H or $C_{1-6}$ alkyl;

$R^{22a}$ and $R^{22b}$ are each independently H, $C_{1-6}$ alkyl, (CH$_2$)$_{2-3}$CF$_3$, AryA, or HetB;

$R^{23}$ is H or $C_{1-6}$ alkyl;

$R^{24}$ is H or $C_{1-6}$ alkyl;

alternatively, $R^{19}$ together with $R^{23}$ or $R^{24}$ and the atoms to which each is attached form a 5- to 7-membered, saturated or unsaturated monocyclic ring optionally containing a heteroatom in addition to the N atom to which $R^{19}$ is attached, wherein the optional heteroatom is selected from N, O and S, where the S is optionally oxidized to S(O) or S(O)2;

alternatively, $R^{20}$ and $R^{21}$ together with the carbon atom to which both are attached form a 5- or 6-membered, saturated monocyclic ring optionally containing a heteroatom, wherein the optional heteroatom is selected from N, O and S, where the S is optionally oxidized to S(O) or S(O)$_2$;

alternatively, $R^{22a}$ together with an $R^{20}$ or $R^{21}$ and the atoms to which each is attached form a 5- to 7-membered, saturated or unsaturated monocyclic ring optionally containing a heteroatom in addition to the N atom to which $R^{22a}$ is attached, wherein the optional heteroatom is selected from N, O and 5, where the S is optionally oxidized to S(O) or S(O)2;

alternatively, $R^{23}$ and $R^{24}$ together with the carbon atom to which both are attached form a 5- or 6-membered, saturated monocyclic ring optionally containing a heteroatom, wherein the optional heteroatom is selected from N, O and S, where the S is optionally oxidized to S(O) or S(O)$_2$;

wherein the monocyclic ring formed by combining $R^{15}$ together with an $R^{17}$ or $R^{18}$, the monocyclic ring formed by combining $R^{16a}$ together with an $R^{17}$ or $R^{18}$, the monocyclic ring formed by combining $R^{17}$ together with an $R^{18}$, the monocyclic ring formed by combining $R^{19}$ together with an $R^{23}$ or $R^{24}$, the monocyclic ring formed by combining $R^{20}$ together with an $R^{21}$, the monocyclic ring formed by combining $R^{22a}$ together with an $R^{20}$ or $R^{21}$, and the monocyclic ring formed by combining $R^{23}$ together with an $R^{24}$, are each independently and optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, NO$_2$, N($R^A$)$R^B$, C(O)N($R^A$)$R^B$, C(O)$R^A$, CO$_2R^A$, $SR^A$, S(O)$R^A$, SO$_2R^A$, or SO$_2$N($R^A$)$R^B$, (4) O—$C_{1-6}$ alkyl, (5) O—$C_{1-6}$ haloalkyl, (6) OH, (7) oxo, (8) halogen, (9) CN, (10) NO$_2$, (11) N($R^A$)$R^B$, (12) C(O)N($R^A$)$R^B$, (13) C(O)$R^A$, (14) C(O)—$C_{1-6}$ haloalkyl, (15) C(O)O$R^A$, (16) OC(O)N($R^A$)$R^B$, (17) $SR^A$, (18) S(O)$R^A$, (19) S(O)$_2R^A$, (20) S(O)$_2$N($R^A$)$R^B$, (21) N($R^A$)CO$R^B$, or (22) N($R^A$)SO$_2R^B$;

AryA is aryl;

HetB is heteroaryl;

d is 2-4;

s is 1-5;

t is 2-3;

v is 1-2; and m, in each instance in which it appears, is independently selected from 0-2.

11. A compound according to claim 9, or a pharmaceutically acceptable salt thereof, which is 3-{5-[(6-amino-1H-pyrazolo[3,4-b]pyridin-3-yl)methoxy]-2-chlorophenoxy}-5-chlorobenzonitrile and which has the following structure:

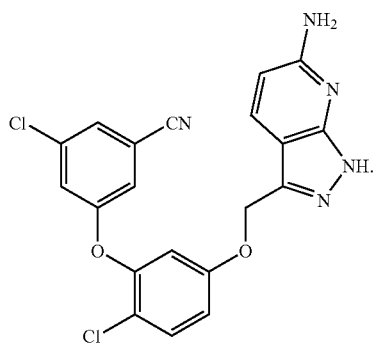

12. A pharmaceutical composition comprising an effective amount of a compound according to claim 1, or a pharmaceutically acceptable salt thereof, and a pharmaceutically acceptable carrier.

13. A pharmaceutical composition comprising an effective amount of a compound according claim 11, or a pharmaceutically acceptable salt thereof, and a pharmaceutically acceptable carrier.

14. A method of inhibiting HIV reverse transcriptase, for treating HIV infection, or for treating or delaying the onset of AIDS, which comprises administering to a subject in need thereof an effective amount of a compound according to claim 1, or a pharmaceutically acceptable salt thereof.

15. A method of inhibiting HIV reverse transcriptase, for treating HIV infection, or for treating or delaying the onset of AIDS, which comprises administering to a subject in need thereof an effective amount of a compound according to claim 11, or a pharmaceutically acceptable salt thereof.

* * * * *